(12) United States Patent
Jasti et al.

(10) Patent No.: US 10,654,780 B2
(45) Date of Patent: May 19, 2020

(54) HALOGENATED NANOHOOP COMPOUNDS AND METHODS OF MAKING AND USING THE SAME

(71) Applicant: University of Oregon, Eugene, OR (US)

(72) Inventors: Ramesh Jasti, Eugene, OR (US); Jeff Van Raden, Eugene, OR (US); Erik Leonhardt, Eugene, OR (US)

(73) Assignee: University of Oregon, Eugene, OR (US)

( * ) Notice: Subject to any disclaimer, the term of this patent is extended or adjusted under 35 U.S.C. 154(b) by 0 days.

(21) Appl. No.: 15/900,529

(22) Filed: Feb. 20, 2018

(65) Prior Publication Data

US 2018/0290952 A1   Oct. 11, 2018

Related U.S. Application Data

(60) Provisional application No. 62/484,264, filed on Apr. 11, 2017.

(51) Int. Cl.
| | | |
|---|---|---|
| *C07C 25/18* | (2006.01) | |
| *B01J 31/02* | (2006.01) | |
| *B01J 35/00* | (2006.01) | |
| *B01J 37/22* | (2006.01) | |
| *B01J 20/22* | (2006.01) | |
| *B01J 20/30* | (2006.01) | |
| *B01J 20/28* | (2006.01) | |
| *H01L 51/00* | (2006.01) | |
| *C07C 17/263* | (2006.01) | |
| *H01L 51/05* | (2006.01) | |
| *B82Y 30/00* | (2011.01) | |
| *B82Y 40/00* | (2011.01) | |
| *H01M 4/60* | (2006.01) | |
| *H01M 4/90* | (2006.01) | |
| *H01L 51/42* | (2006.01) | |
| *H01M 4/62* | (2006.01) | |

(52) U.S. Cl.
CPC .............. *C07C 25/18* (2013.01); *B01J 20/22* (2013.01); *B01J 20/28007* (2013.01); *B01J 20/3085* (2013.01); *B01J 31/0231* (2013.01); *B01J 35/0006* (2013.01); *B01J 37/22* (2013.01); *C07C 17/263* (2013.01); *H01L 51/005* (2013.01); *H01L 51/0071* (2013.01); *H01L 51/0093* (2013.01); *B82Y 30/00* (2013.01); *B82Y 40/00* (2013.01); *C07C 2603/92* (2017.05); *H01L 51/0558* (2013.01); *H01L 51/0575* (2013.01); *H01L 51/424* (2013.01); *H01M 4/60* (2013.01); *H01M 4/62* (2013.01); *H01M 4/9008* (2013.01); *Y10S 977/734* (2013.01); *Y10S 977/842* (2013.01)

(58) Field of Classification Search
CPC .. B01J 20/22; B01J 20/28007; B01J 20/3085; B01J 31/0231; B01J 35/0006; B01J 37/22; C07C 17/263; C07C 2603/92; H01L 51/005; H01L 51/0071; H01L 51/0093; H01L 51/0558; H01L 51/0575; H01L 51/424; B82Y 30/00; B82Y 40/00; H01M 4/60; H01M 4/62; H01M 4/9008; Y10S 977/734; Y10S 977/842

See application file for complete search history.

(56) References Cited

U.S. PATENT DOCUMENTS

| | | | | |
|---|---|---|---|---|
| 8,461,403 | B2 * | 6/2013 | Jasti ........................... | C07C 1/22 568/626 |
| 8,895,768 | B2 * | 11/2014 | Yamago .................. | C07C 1/325 556/136 |
| 8,987,538 | B2 * | 3/2015 | Jasti ........................... | C07C 1/22 568/3 |
| 9,029,551 | B2 * | 5/2015 | Itami ....................... | C07C 15/20 546/259 |
| 9,090,473 | B2 * | 7/2015 | Jasti ........................ | C07C 43/21 |
| 9,162,939 | B2 * | 10/2015 | Jasti ........................... | C07C 1/22 |
| 9,266,909 | B2 * | 2/2016 | Itami ....................... | C07C 1/20 |
| 9,481,618 | B2 * | 11/2016 | Itami ....................... | C07C 1/28 |
| 9,527,737 | B2 * | 12/2016 | Itami ..................... | B82Y 40/00 |
| 2011/0166390 | A1 * | 7/2011 | Jasti ........................... | C07C 1/22 568/3 |
| 2012/0220790 | A1 | 8/2012 | Yamago | |
| 2013/0245327 | A1 * | 9/2013 | Jasti ........................... | C07C 1/22 568/633 |
| 2015/0152022 | A1 * | 6/2015 | Jasti ........................... | C07C 1/22 585/320 |
| 2016/0372684 | A1 * | 12/2016 | Jasti ..................... | C07D 471/08 |
| 2018/0290952 | A1 * | 10/2018 | Jasti ....................... | C07C 25/18 |
| 2019/0025315 | A1 * | 1/2019 | Jasti ....................... | C07C 63/331 |

OTHER PUBLICATIONS

CAS Abstract of J. Rio, Physical Chemistry Chemical Physics (2016) (Year: 2016).*
EMail Communication to CAS (2019) (Year: 2019).*
Takase et al., 15 Organic Letters (2013) (Year: 2013).*
A. Kikuchi et al., 126 Journal of the American Chemical Society (2004) (Year: 2004).*
K. Oki et al., 46 Chemistry Letters, (2017) (Year: 2017).*
K. Mutoh et al., 17 Physical Chemistry Chemical Physics (2015) (Year: 2015).*
J. Rio et al., 18 Physical Chemistry Chemical Physics (2016) (Year: 2016).*
Y. Ishii et al., Organic Letters (2014) (Year: 2014).*

(Continued)

*Primary Examiner* — Alexander R Pagano
(74) *Attorney, Agent, or Firm* — Klarquist Sparkman, LLP

(57) ABSTRACT

Disclosed herein are embodiments of halogenated nanohoop compounds and assemblies thereof that can be used to for a variety of biological and chemical applications. The halogenated nanohoop compounds described herein exhibit non-covalent interactions that promote their ability to stack and form column-like assemblies having uniform pore size and that do not exhibit structural defects typically associated with other column-like structures, such as carbon nanotubes. Assemblies described herein also are capable of non-covalent interactions with other assemblies and thus can be used to form networks of the assemblies described herein.

9 Claims, 25 Drawing Sheets

(56) References Cited

OTHER PUBLICATIONS

J. M. Van Raden et al., 85 Journal of Organic Chemistry, 129-141 (2020) (Year: 2020).*
E. Kayahara et al., 56 Angewandte Chemie, International Edition, 10428-10432 (2017) (Year: 2017).*
S. Hashimoto et al., 16 Organic Letters, 5973-5976 (2018) (Year: 2018).*
E. J. Leonhardt et al., ChemRxiv (2018) 1-26, 2018 (Year: 2018).*
Ball et al., "Stepping into the Light: Conjugated Macrocycles with Donor-Acceptor Motifs," ACS Cent. Sci., 1, 416-417, Oct. 27, 2015.
Darzi, Research Presentation/Slides, Sep. 24, 2014.
Havinga et al., "A new class of small band gap organic polymer conductors," *Polymer Bulletin*, 29(119): 119-126, Aug. 1992.
Hirst "Synthesis of Nitrogen-Substituted Cycloparaphenylenes," Dissertation, May 2014.
Hirst "Synthesis of Nitrogen-Substituted Cycloparaphenylenes," Thesis Defense Presentation, May 13, 2014.
Iwamoto et al., "Selective and Random Syntheses of [n]Cycloparaphenylenes (n=8-13) and Size Dependence of Their Electronic Properties," *Journal of the American Chemical Society*, 133(21): 8354-8361, May 4, 2011.
Zhang et al., "Giant Cyclo[n]thiophenes with Extended π Conjugation," *Angewandte Chemie Int. Ed.*, 48(36): 6632-6635, Jun. 27, 2009.
Kubota et al., "$\eta^6$-Cycloparaphenylene Transition Metal Complexes: Synthesis, Structure, Photophysical Properties, and Application to the Selective Monofunctionalization of Cyclopharaphenylenes," *J. Am. Chem. Soc.*,137, 1356-1361; Jan. 12, 2015.
Final Office action issued in U.S. Appl. No. 15/187,644 dated Aug. 19, 2019.

* cited by examiner

212

3.79 Å

2.53-2.85 Å

504

3.69 Å, 3.94 Å

2.48-2.84 Å

402

3.68 Å

2.53-2.62 Å

ΔE = -23.08 kcal/mol

ΔE = -21.30 kcal/mol

ΔE = -19.48 kcal/mol

ΔE = -17.64 kcal/mol

ΔE = -15.96 kcal/mol

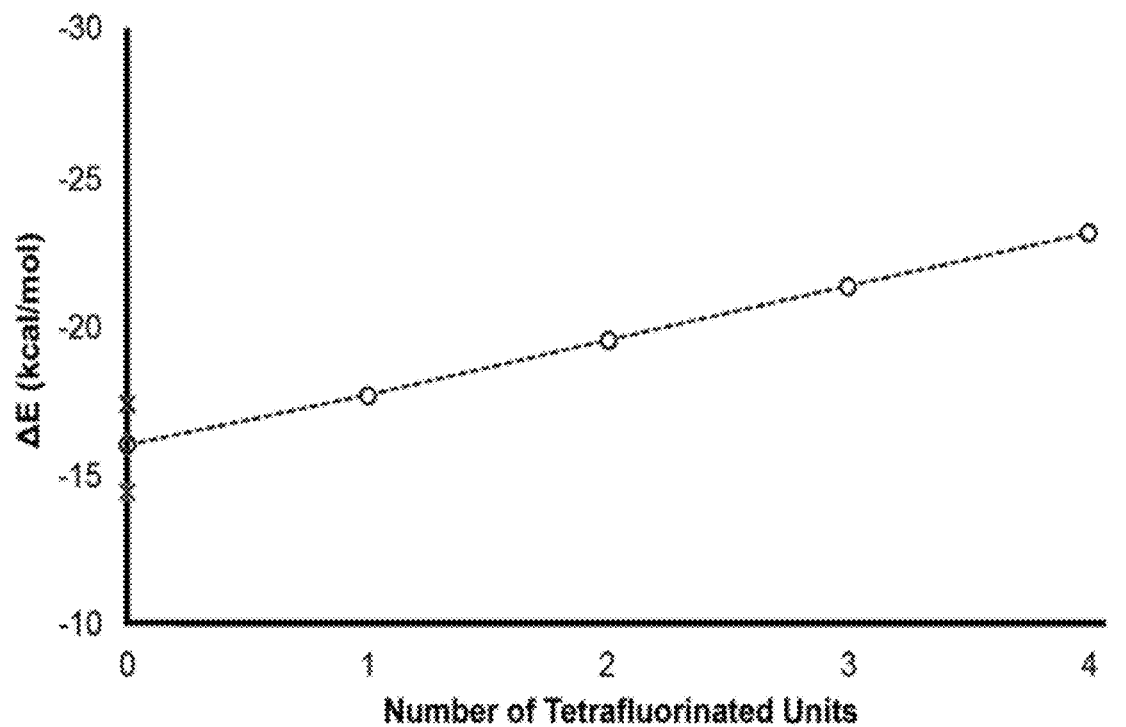
FIG. 34
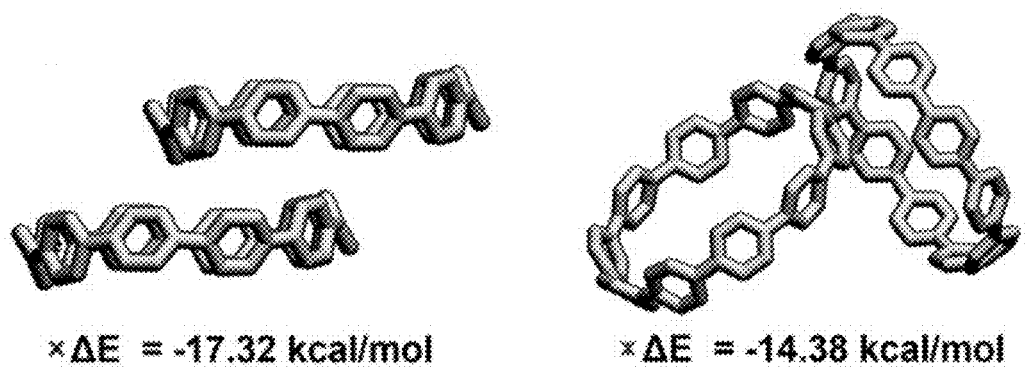
×ΔE = -17.32 kcal/mol    ×ΔE = -14.38 kcal/mol
FIG. 35A                  FIG. 35B

HALOGENATED NANOHOOP COMPOUNDS AND METHODS OF MAKING AND USING THE SAME

CROSS-REFERENCED TO RELATED APPLICATIONS

This application claims the benefit of the earlier filing date of U.S. Provisional Application No. 62/484,264, filed on Apr. 11, 2017, which prior application is incorporated by reference herein in its entirety.

ACKNOWLEDGMENT OF GOVERNMENT SUPPORT

This invention was made with government support under Contract No. CHE-1255219 awarded by the National Science Foundation. The government has certain rights in the invention.

FIELD

The present disclosure concerns halogenated nanohoop compounds and assemblies thereof, as well as methods of making and using the same.

BACKGROUND

The emergence of functional, porous materials has had a profound impact on the development of numerous fields within the disciplines of chemistry, physics, and biology. As such, one important focus of synthetic chemistry is to develop new materials with well-defined and increasingly diverse functional pores. Significant research on metal-organic frameworks (MOFs) and covalent-organic frameworks (COFs) has provided a solid roadmap for the design of new porous materials, ultimately highlighting important design elements, such as self-assembly, that lead to well-defined structure and thus, functionality. Likewise, investigations with materials, such as carbon nanotubes (CNTs), have illustrated the importance of pore shape, size, and composition. CNTs, due to their inherently porous, smooth, π-rich cylindrical channels, have shown remarkable properties, such as mass transport and molecular encapsulation—an increasingly important property of CNTs, which has enabled synthetic access to uniform materials such as graphene nanoribbons as well as various other linear polymeric materials. While CNTs are poised to act as robust tools, drawbacks such as insolubility, inhomogeneity, and ill-defined structure present challenges in their full implementation in various applications.

In nature, non-covalent interactions direct the assembly of relatively simple building blocks into the formation of large, complex assemblies, such as the DNA double helix or the tertiary structure of proteins. Through appropriate molecular design, chemists have leveraged similar interactions to access unique molecular organization, resulting in molecules and materials with enhanced properties or exotic functionality. There exists a need in the art, however, for compounds that can provide materials having reactivity similar to CNTs but that can be made with improved uniformity and purity not achieved with conventional CNT synthesis techniques. There also is a need in the art for compounds that can be easily assembled into uniform assemblies without complicated chemical modifications and/or coupling reactions.

SUMMARY

Described herein are embodiments of compounds having a nanohoop structure and assemblies of such compounds. In particular disclosed embodiments, the compounds are halogenated nanohoop compounds comprising at least one halogen atom coupled to the nanohoop skeleton of the compound. In particular disclosed embodiments, the halogenated nanohoop compounds can comprise additional aromatic rings within the nanohoop skeleton that do not require a halogen atom. For example, electron donating units and/or electron accepting units, as described herein, can be used in combination with one or more halogenated aromatic rings to provide a halogenated nanohoop compound. The nanohoop compounds can interact via C—H/C—X interactions (wherein X is a halogen atom selected from chloro, fluoro, bromo, or iodo) such that they assembly into a column-like structure (or an "assembly" as described herein). In some embodiments, assemblies can comprise at least two nanohoop compounds, at least one of which is a halogenated nanohoop compound. Assemblies described herein also can interact to form assembly networks, wherein perhaloarene-arene interactions act to non-covalently join the various assemblies into the network.

The halogenated nanohoop compounds and assemblies described herein can be used in a variety of applications, such as chemical and biological applications. Solely by way of example, the halogenated nanohoop compounds can be used to make energy storage devices, nanoreactors, electronic devices, biological transport devices, or chemical devices. In some embodiments.

Also disclosed herein are embodiments of methods used to make the halogenated nanohoop compound described herein. In particular embodiments, nanohoop precursors can be easily cross-coupled to provide a halogenated nanohoop compound.

The foregoing and other objects, features, and advantages of the present disclosure will become more apparent from the following detailed description, which proceeds with reference to the accompanying figures.

BRIEF DESCRIPTION OF THE DRAWINGS

FIG. 34 is a plot of dimer stabilization energy (ΔE) versus the number of tetrafluorophenylene moieties present in the dimer of halogenated nanohoop compound 212.

FIGS. 35A and 35B show the stabilization energies of the tubular-like dimer (FIG. 35A) and the herringbone-like dimer (FIG. 35B) extracted from the crystal structure of pristine non-fluorinated [10]CPP.

DETAILED DESCRIPTION

I. Explanation of Terms

Figure 1:
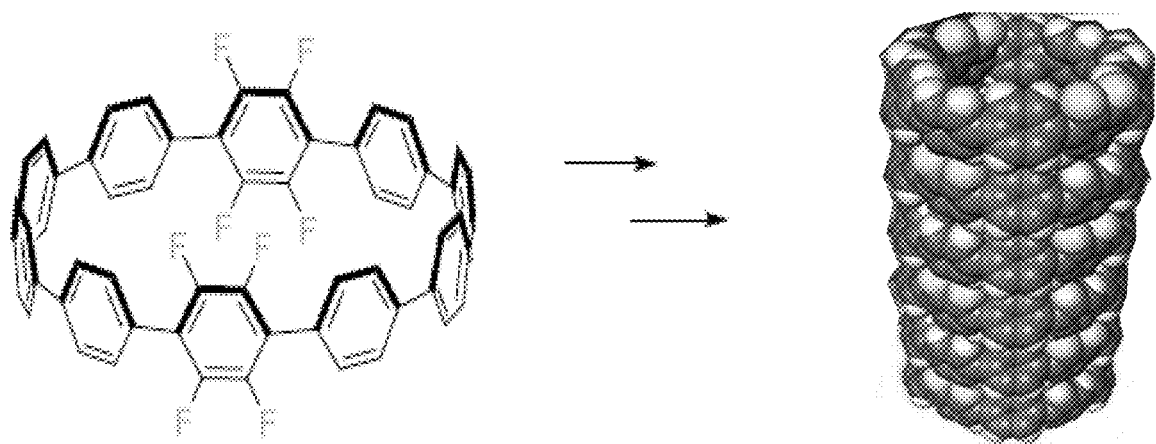
FIG. 1 is an illustration of a representative halogenated nanohoop compound and a representative assembly formed from stacking individual halogenated nanohoop compounds.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided. Certain functional group terms include a "—" symbol at the beginning of the functional group formula; this symbol is not a part of the functional group, but instead denotes how the functional group connects to the formulas described herein. For example, a functional group with a formula "—OC(O)R$^b$" is attached to an atom of the functionalized compound by the oxygen atom of the functional group that is next to the "—" symbol.

Acyl Halide: —C(O)X, wherein X is a halogen, such as Br, F, I, or Cl.

Acyloxy: —OC(O)R$^b$, wherein R$^b$ is selected from hydrogen, alkyl, alkenyl, alkynyl, aryl, heteroalkyl, heteroalkenyl, heteroalkynyl, or heteroaryl.

Aldehyde: —C(O)H.

Aliphatic: A hydrocarbon group having at least one carbon atom to 50 carbon atoms ($C_1$-$C_{50}$), such as one to 25 carbon atoms ($C_1$-$C_{25}$), or one to ten carbon atoms ($C_1$-$C_{10}$), and which includes alkanes (or alkyl), alkenes (or alkenyl), alkynes (or alkynyl), including cyclic versions thereof, and further including straight- and branched-chain arrangements, and all stereo and position isomers as well.

Alkenyl: An unsaturated monovalent hydrocarbon having at least two carbon atom to 50 carbon atoms ($C_2$-$C_{50}$), such as two to 25 carbon atoms ($C_2$-$C_{25}$), or two to ten carbon atoms ($C_2$-$C_{10}$), and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cycloalkenyl), cis, or trans (e.g., E or Z).

Alkoxy: —O-alkyl, —O-alkenyl, or —O-alkynyl, with exemplary embodiments including, but not limited to, methoxy, ethoxy, n-propoxy, isopropoxy, n-butoxy, t-butoxy, sec-butoxy, n-pentoxy.

Alkyl: A saturated monovalent hydrocarbon having at least one carbon atom to 50 carbon atoms ($C_1$-$C_{50}$), such as one to 25 carbon atoms ($C_1$-$C_{25}$), or one to ten carbon atoms ($C_1$-$C_{10}$), wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkynyl: An unsaturated monovalent hydrocarbon having at least two carbon atom to 50 carbon atoms ($C_2$-$C_{50}$), such as two to 25 carbon atoms ($C_2$-$C_{25}$), or two to ten carbon atoms ($C_2$-$C_{10}$), and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Amide: —C(O)NR$^b$R$^c$ wherein each of R$^b$ and R$^c$ independently is selected from hydrogen, aliphatic, heteroaliphatic, aryl, heteroaryl, or any combination thereof.

Amine: —NR$^b$R, wherein each of R$^b$ and R$^c$ independently is selected from hydrogen, alkyl, alkenyl, alkynyl, aryl, heteroalkyl, heteroalkenyl, heteroalkynyl, heteroaryl, and any combination thereof.

Aryl: An aromatic carbocyclic group comprising at least five carbon atoms to 15 carbon atoms ($C_5$-$C_{15}$), such as five to ten carbon atoms ($C_5$-$C_{10}$), having a single ring or multiple condensed rings, which condensed rings can or may not be aromatic provided that the point of attachment to a remaining position of the compounds disclosed herein is through an atom of the aromatic carbocyclic group.

Assembly: A structure formed between at least one halogenated nanohoop compound and one or more other nanohoop compounds that may or may not be halogenated, one or more carbon nanotubes (or a component thereof), and/or one or more other hoop-like compounds (e.g., macrocyclic compounds). In particular disclosed embodiments, an assembly comprises two or more halogenated nanohoops.

Carboxyl: —C(O)OR$^b$, wherein R$^b$ is alkyl, alkenyl, alkynyl, aryl, heteroalkyl, heteroalkenyl, heteroalkynyl, heteroaryl, hydrogen, and any combination thereof.

C—H/C—X Interaction: A non-covalent, chemical interaction between at least one halogenated nanohoop compound and one or more other halogenated or non-halogenated nanohoop compounds (representative non-halogenated nanohoop compounds are described by U.S. Patent Application Publication No. 2016-0372684, which is incorporated herein by reference), wherein the interaction takes place between a halogen atom of a halogenated nanohoop compound and one or more hydrogen atoms of one or more halogenated or non-halogenated nanohoop compounds. The "X" of C—H/C—X represents a halogen atom selected from fluoro, bromo, iodo, or chloro.

Electron-Accepting Group (EAG): A functional group capable of accepting electron density from the ring to which it is directly attached, such as by inductive electron withdrawal.

Electron-Accepting Unit: An aromatic ring comprising one or more electron-accepting groups or an aromatic ring that comprises one or more heteroatoms and/or substituents that are capable of accepting electron density from the core ring to which they are attached. In such embodiments, the core ring comprises two carbon atoms that each are attached to two different rings in a nanohoop structure.

Electron-Donating Group (EDG): A functional group capable of donating at least a portion of its electron density into the ring to which it is directly attached, such as by resonance.

Electron-Donating Unit: An aromatic ring comprising one or more electron-donating groups.

Ester: —C(O)OR$^b$, wherein R$^b$ is selected from alkyl, alkenyl, alkynyl, aryl, heteroalkyl, heteroalkenyl, heteroalkynyl, or heteroaryl.

Functionalized Nanohoop Compound: A nanohoop compound comprising at least one aryl ring comprising at least one electron-accepting group (or an aryl ring that forms an electron-accepting unit) and at least one aryl ring comprising at least one electron-donating group (or an aryl ring that forms an electron-donating unit).

Haloaliphatic: An aliphatic group wherein one or more hydrogen atoms, such as one to 10 hydrogen atoms, independently is replaced with a halogen atom, such as fluoro, bromo, chloro, or iodo.

Haloalkyl: An alkyl group wherein one or more hydrogen atoms, such as one to 10 hydrogen atoms, independently is replaced with a halogen atom, such as fluoro, bromo, chloro, or iodo. In an independent embodiment, haloalkyl can be a $CX_3$ group, wherein each X independently can be selected from fluoro, bromo, chloro, or iodo.

Halogen: An atom selected from fluoro, chloro, bromo, or iodo.

Halogenated Nanohoop: A compound comprising para-linked aromatic groups (e.g., aryl groups) that are organized to form a hoop-like structure wherein at least one of the aromatic groups comprises one or more halogen atoms such that a hydrogen group of the aromatic group is replaced with a halogen atom.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroalkyl/Heteroalkenyl/Heteroalkynyl: An alkyl, alkenyl, or alkynyl group (which can be branched, straight-chain, or cyclic) comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroaryl: An aryl group comprising at least one heteroatom to six heteroatoms, such as one to four heteroatoms, which can be selected from, but not limited to oxygen, nitrogen, sulfur, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group.

Ketone: —C(O)$R^b$, wherein $R^b$ is selected from aliphatic, heteroaliphatic, aryl, heteroaryl, and any combination thereof.

Nanohoop: A compound comprising para-linked aromatic groups that are organized to form a hoop-like structure.

Nanoreactor: An assembly of nanohoop compounds disclosed herein wherein the nanohoop compounds are organized into an assembly having a column-like structure that thereby defines an inner pore, which serves to host one or more guest species, such as chemical compounds, during chemical modifications made to the guest species. Exemplary chemical modifications include, but are not limited to, polymerization, hydrogenation, oxidation, ammonia synthesis/decomposition, hydrosilylation, cycloadditions, cross-coupling reactions, photocatalytic reactions, electrochemical reactions, and the like.

Perhaloarene-arene Interaction: A non-covalent interaction between two or more nanohoop compounds wherein at least one of the nanohoop compounds is a halogenated nanohoop. In some embodiments, the two or more nanohoop compounds can be selected from at least one halogenated nanohoop compound and one or more halogenated nanohoop compound(s), non-halogenated nanohoop compound(s), or a combination thereof. In some embodiments, the perhaloarene-arene interaction can be a perfluoroarene-arene interaction wherein two nanohoop compounds are associated through non-covalent interactions between a fluorinated aryl ring of one of the nanohoop compounds and a non-fluorinated aryl ring of the other nanohoop compound.

Quaternary Amine: —N+$R^b R^c R^d$, wherein each of $R^b$, $R^c$, and $R^d$ independently are selected from hydrogen, aliphatic, heteroaliphatic, aryl, heteroaryl, and any combination thereof.

Sulfonyl/Sulfonate: —SO$_2$$R^b$, wherein $R^b$ is selected from hydrogen, aliphatic, heteroaliphatic, aryl, heteroaryl, and any combination thereof.

A person of ordinary skill in the art would recognize that the definitions provided above are not intended to include impermissible substitution patterns (e.g., methyl substituted with 5 different groups, and the like). Such impermissible substitution patterns are easily recognized by a person of ordinary skill in the art. In formulas and specific compounds disclosed herein, a hydrogen atom is present and completes any formal valency requirements (but may not necessarily be illustrated) wherever a functional group or other atom is not illustrated. For example, a phenyl ring that is drawn as

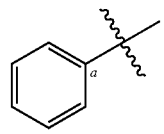 [SMILES: *c1ccccc1]

comprises a hydrogen atom attached to each carbon atom of the phenyl ring other than the "a" carbon, even though such hydrogen atoms are not illustrated.

Any functional group disclosed herein and/or defined above can be substituted or unsubstituted, unless otherwise indicated herein.

ABBREVIATIONS

CNT: Carbon nanotube(s)
[X]CPP: Cycloparaphenylene (wherein X represents an integer corresponding to the number of aryl rings present in the cycloparaphenylene).
DCM: Dichloromethane
NMR: Nuclear magnetic resonance II. Introduction Perfluoroarene-arene interactions have been utilized in the art to align multiple linear biaryl systems in a stack-like conformation; however, these biaryl systems are limited in that they do not possess inherent porosity. The present disclosure describes novel halogenated aryl-based compounds (such as halogenated nanohoop compounds), which possess inherent porosity and that can be arranged in assemblies resembling the structural characteristics of carbon nanotubes, but that avoid typical carbon nanotube synthetic methods and that exhibit unique uniformity and are defect-free. The disclosed halogenated nanohoop compounds can be used to construct assemblies suitable for use as porous materials, conductive films, synthetic scaffolds, energy storage device components, sensors, and the like. In some embodiments, the halogenated nanohoop compounds and assemblies therefore exhibit an inherently porous nature and radially oriented π-systems, which allow them to readily engage in host-guest chemistry. Additionally, the pore diameters and unique electronic properties of the disclosed halogenated nanohoop compounds and assemblies thereof can be modified, such as by changing the number of aryl rings in the nanohoop and/or by modifying the types of aromatic rings included in the nanohoop. The halogenated nanohoop compounds described herein are capable of interacting with other halogenated nanohoop compounds, non-halogenated nanohoop compounds, carbon nanotubes, and the like, through C—H/C—X non-covalent interactions (wherein X is a halogen atom) to form assemblies with the ability to function similar to CNTs. Unlike CNTs, however, the disclosed halogenated compounds are easily synthesized and do not require purification from complex reaction mixtures and further are readily tuned in terms of porosity, functionality, and uniformity not achieved by conventional CNTs. Assemblies of the disclosed halogenated nanohoop compounds can themselves interact with other assemblies, such as through perhaloarene-arene interactions. Thus, a plurality of assemblies can be arranged to provide a network of column-like structures.

III. Halogenated Nanohoop Compounds

Disclosed herein are embodiments of compounds that adopt unique nanostructures, such as hoop-shaped structures comprising para-linked aromatic groups (referred to as nanohoops). The compounds further comprise one or more halogen atoms attached to the aromatic rings that facilitate non-covalent interactions with other such compounds and/or other compounds having a similar nanohoop structure but that are not functionalized with a halogen atoms. In particular disclosed embodiments, the halogenated compounds disclosed herein are halogenated nanohoops comprising para-linked units of aromatic rings that exhibit singular aromatic ring planes that are perpendicular to the radius of the hoop and therefore the carbon atoms do not all sit in one plane of the aromatic ring.

In some embodiments, the halogenated compounds are nanohoops having structures satisfying Formula I.

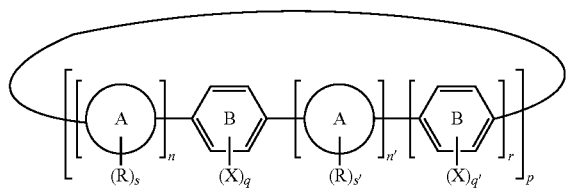

Formula I

With reference to Formula I, the "hoop-shaped" nature of the compounds is represented by the solid curved line, which in turn represents a bond formed between a carbon atom of an "A" ring or "B" ring and a para-positioned carbon atom of another A or B ring to form the hoop structure. Also with reference to Formula I, each "A" ring independently represents an aromatic ring that does not require a halogen atom and each "B" ring independently represents an aromatic ring comprising at least one halogen atom, represented by X in Formula 1. Each X independently can be selected from chloro, fluoro, bromo, or iodo. Each R independently can be selected from an electron-donating group or an electron-accepting group. Each n independently can be an integer selected from 1 to 24; each n' and r independently can be integers selected from 0 to 24; p can be an integer selected from 1 to 12; each s and s' independently can be an integer selected from 0 to 4; and each q and q' independently can be an integer selected from 1 to 4. In particular disclosed embodiments, when each of n, n', and r is 0, then p is at least 6. In yet additional embodiments, when p is 1, then at least one of n, n', or r is 5 and/or n+n'+r=5.

The nanohoop compounds described herein comprise at least one B ring having one or more halogen atoms present. In some embodiments, the halogen atom is selected from fluoro, chloro, bromo, or iodo. In particular disclosed embodiments, the halogen atom is fluoro. In some embodiments, the number of halogen atoms present on a B ring can be 4, 3, 2, or 1. The halogen atoms may be positioned on any open position of a B ring. In embodiments comprising 2 halogen atoms, the halogen atoms can be positioned adjacent to each other or opposite each other. In some embodiments, multiple different types of halogen atoms can be present on the B ring (e.g., a mixture of one or more fluoro atoms and one or more other halogen atoms, such as chloro, bromo, or iodo).

In some embodiments, each "A" ring independently can be selected from an aryl ring comprising an electron-accepting group; or a heteroaryl ring comprising an electron-accepting group or one or more heteroatoms and/or substituents that are capable of accepting electron density from a core ring to which they are attached (wherein the core ring is a ring comprising two carbon atoms that each are attached to two different rings of the nanohoop compound). In some embodiments, each "A" ring independently can be selected from an aryl ring comprising an electron-donating group; or a heteroaryl ring optionally comprising an electron-donating group.

Representative examples of "A" rings include, but are not limited to, (i) phenyl; (ii) phenyl optionally substituted with one or more electron-donating substituents described herein; (iii) a heteroaryl ring system having a structure satisfying a formula:

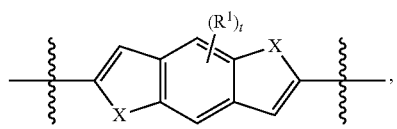

wherein X is selected from O, S, and $NR^b$ (wherein $R^b$ is as defined herein), $R^1$ is selected from an electron-donating group disclosed herein, and t is 0, 1, or 2; (iv) phenyl substituted with one or more electron-accepting substituents described herein; or (v) pyridinyl substituted with an aliphatic or aryl group; or a ring system having a structure satisfying a formula:

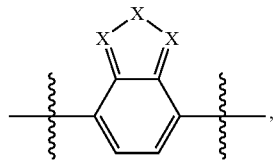

wherein each X independently is selected from O, S, N, or $NR^b$ wherein $R^b$ is as defined herein.

In some embodiments, each A ring independently can be selected from phenyl; benzo[1,2-b:4,5-b']dithiophenyl optionally substituted with one or more electron-donating substituents described herein; benzo[1,2-b:4,5-b']difuranyl optionally substituted with one or more electron-donating substituents described herein; 4,4-dimethyl-4H-cyclopenta[2,1-b:3,4-b']dithiophene optionally substituted with one or more electron-donating substituents described herein; or 1,5-dihydropyrrolo[2,3-f]indolyl optionally substituted with one or more electron-donating substituents described herein; benzo[c][1,2,5]thiadiazolyl; benzo[c][1,2,5]oxadiazolyl; or 2H-benzo[d][1,2,3]triazolyl.

With reference to the groups discussed above and with reference to the "R" groups of Formula I, electron-donating groups can be selected from functional groups capable of donating at least a portion of its electron density into the ring to which it is directly attached, such as by resonance. Exemplary electron-donating groups can be selected from, but not limited to, one or more of the following: alkoxy, thioether, amide, amine, hydroxyl, thiol, acyloxy, aliphatic (e.g., alkyl, alkenyl, alkynyl), aryl, or combinations thereof. With reference to the groups discussed above and with reference to the "R" groups of Formula I, electron-accepting groups can be selected from functional groups capable of accepting electron density from the ring to which it is directly attached, such as by inductive electron withdrawal. Exemplary electron-accepting groups can be selected from, but not limited to, one or more of the following: aldehyde, ketone, ester, carboxylic acid, acyl, acyl halide, cyano, sulfonate, nitro, nitroso, quaternary amine, pyridinyl (or pyridinyl wherein the nitrogen atom is functionalized with an aliphatic or aryl group), alkyl halide, or combinations thereof.
In particular disclosed embodiments, the halogenated nanohoop compounds can have structures satisfying any one of Formulas IIA-IIL below.
TABLE 1
Additional Nanohoop Compound Formulas
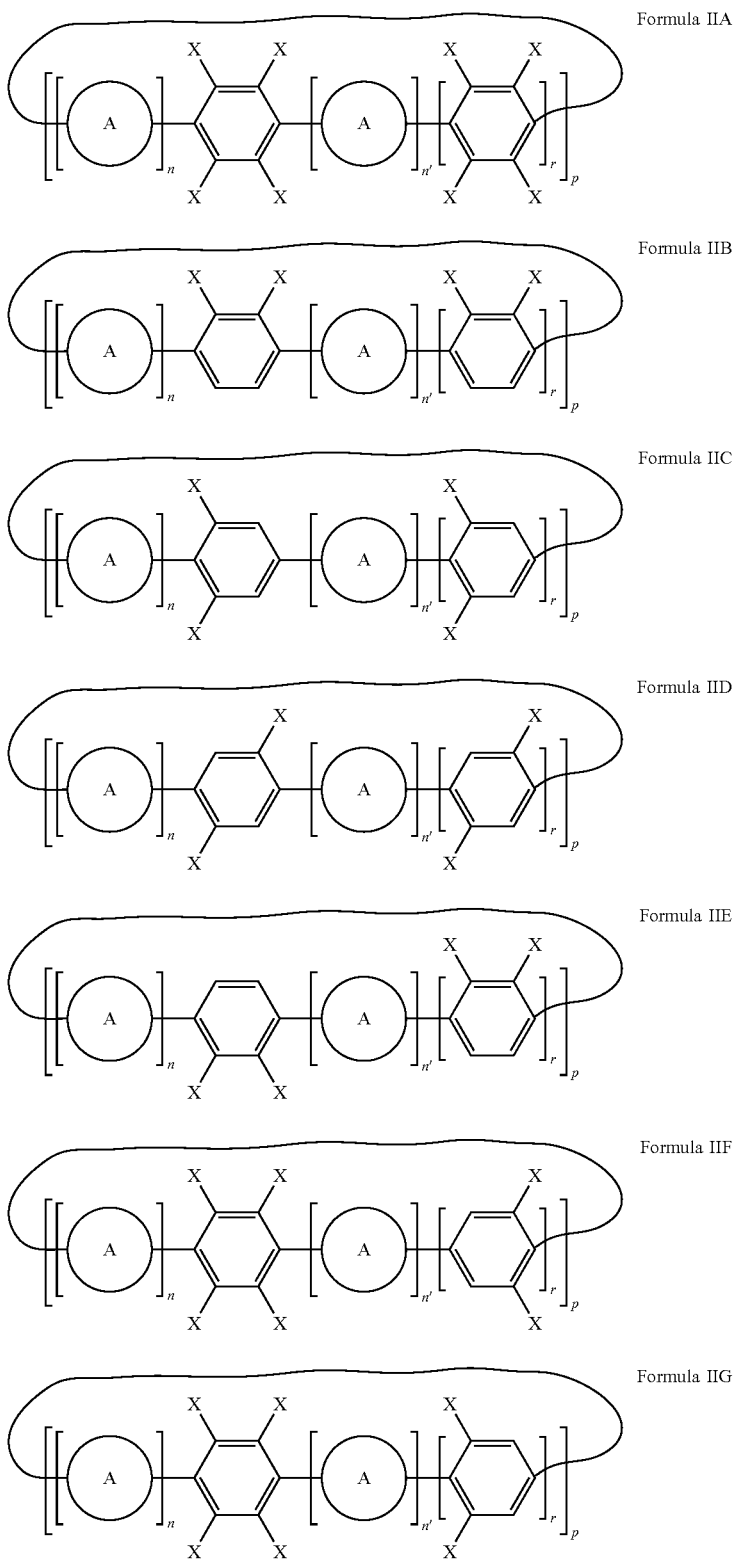

TABLE 1-continued
Additional Nanohoop Compound Formulas
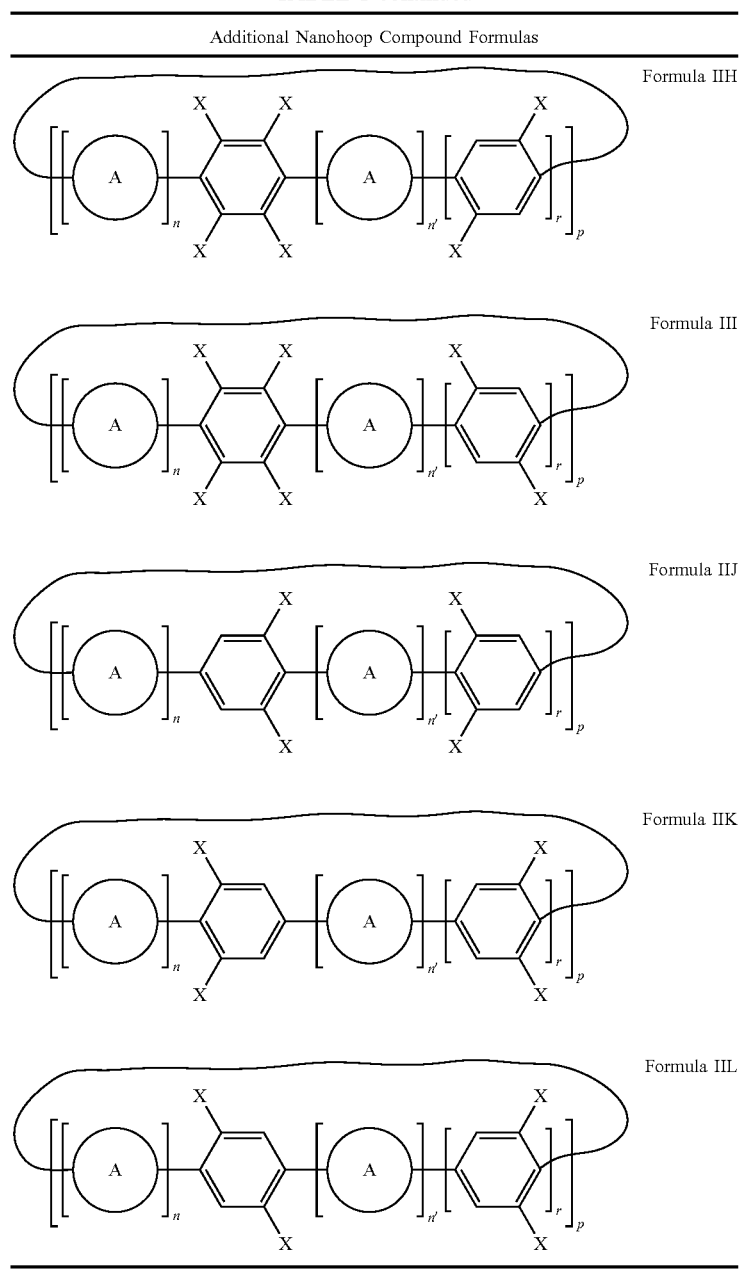
Formula IIH
Formula III
Formula IIJ
Formula IIK
Formula IIL
In some embodiments, the halogenated nanohoop compounds can have structures satisfying Formulas IIIA-IIIC.
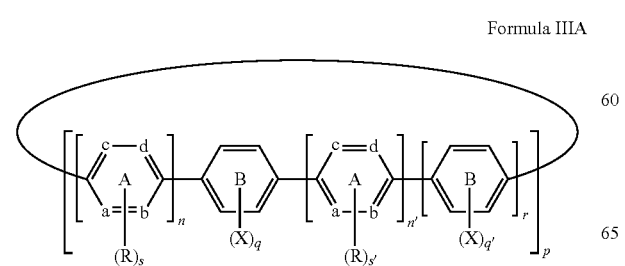
Formula IIIA
-continued
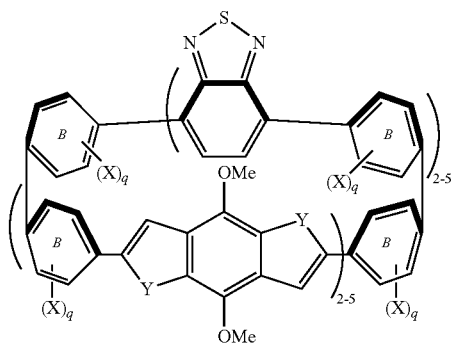
Formula IIIB -continued Formula IIIC

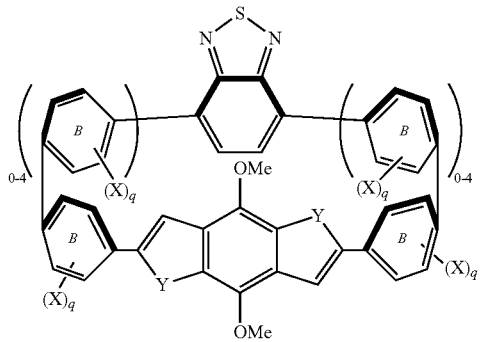

With reference to Formula IIIA, each Ring A, Ring B, X, R, n, n', q, q', s, s', r, and p independently can be as recited above for Formula I; and each a, b, c, and d can be selected from carbon or nitrogen. With reference to Formulas IIIB and IIIC, each X independently can be as recited above for Formula I; each Y independently can be selected from O, S, or NH; each q independently can be as recited above for Formula I.

Embodiments of representative halogenated nanohoop compounds are illustrated below in Table 2. With reference to the compounds in Table 2, each X independently can be selected from fluoro, iodo, bromo, or chloro; and each Y independently can be selected from O, S, or NH.

TABLE 2

Representative Halogenated Nanohoop Compounds

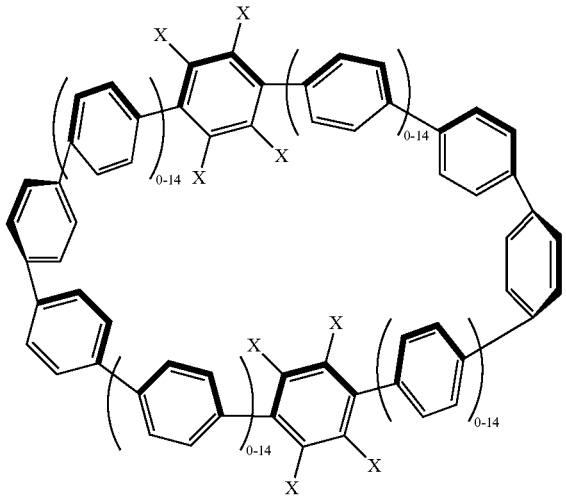

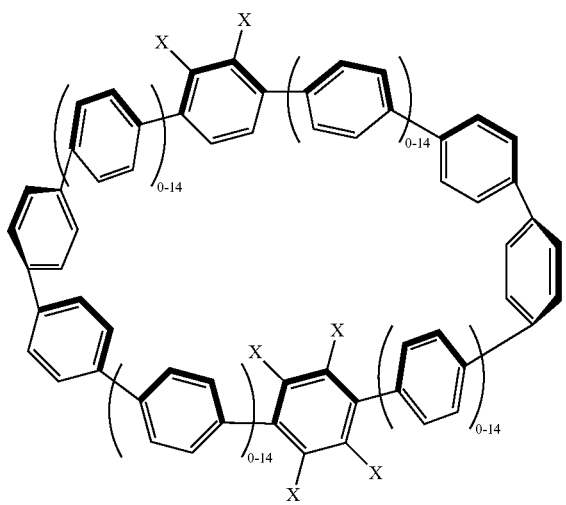

TABLE 2-continued
Representative Halogenated Nanohoop Compounds
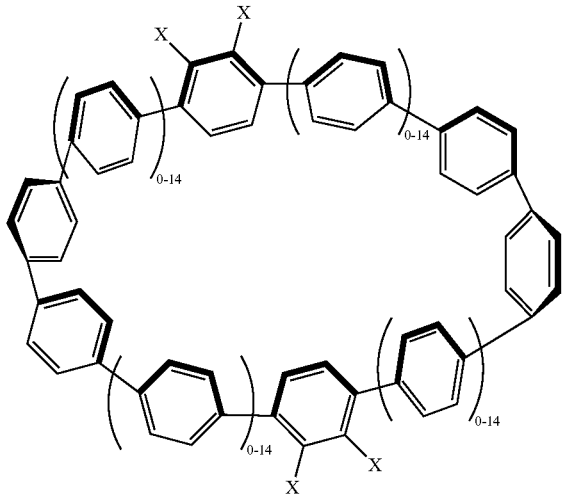
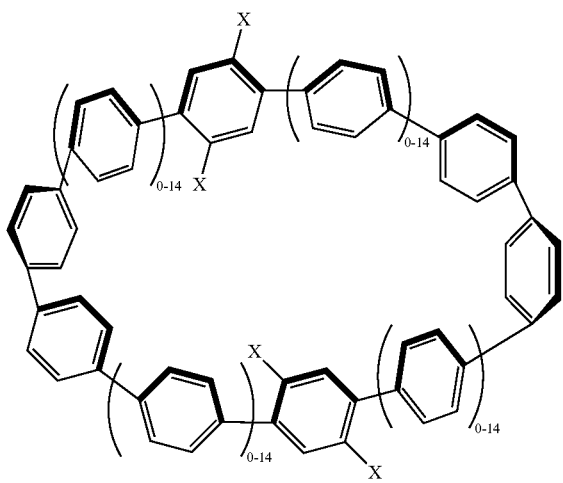
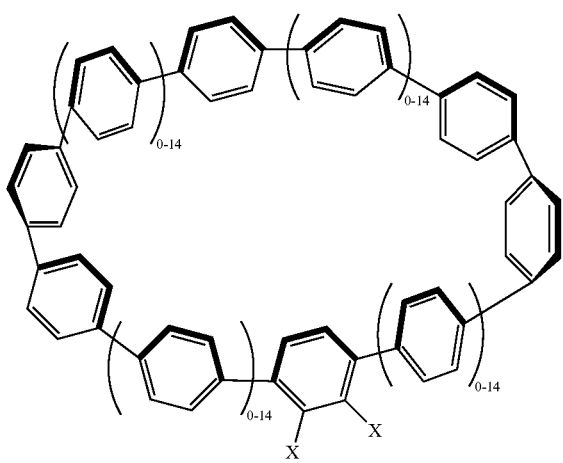

TABLE 2-continued
Representative Halogenated Nanohoop Compounds
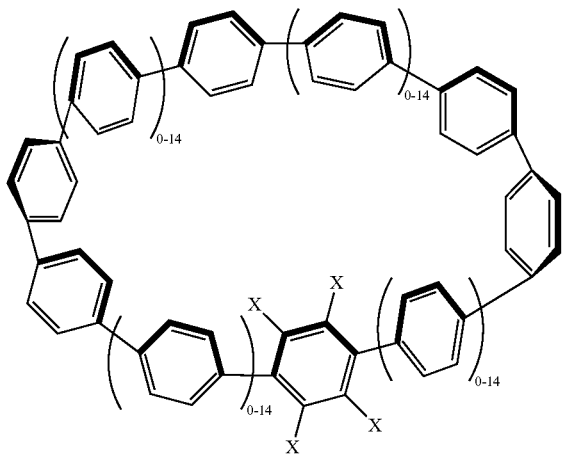
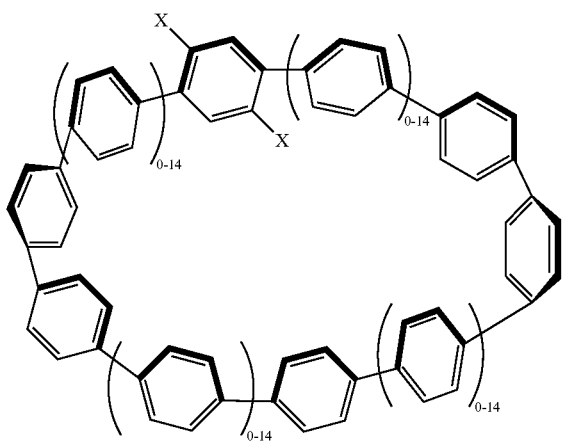
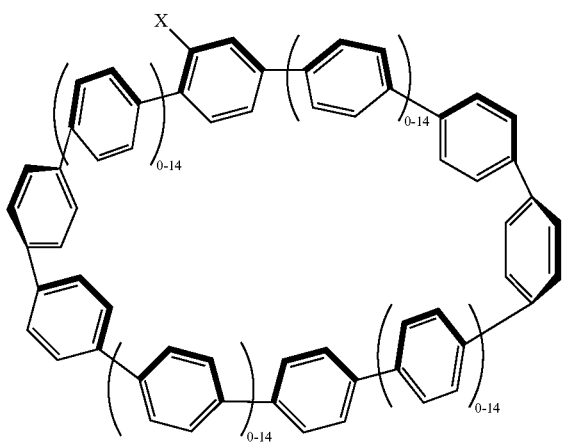

TABLE 2-continued
Representative Halogenated Nanohoop Compounds
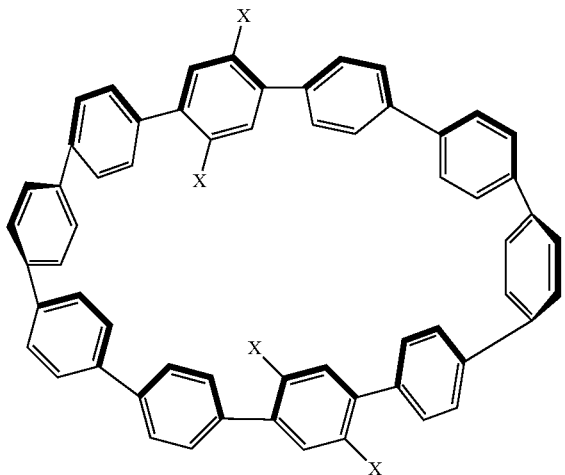
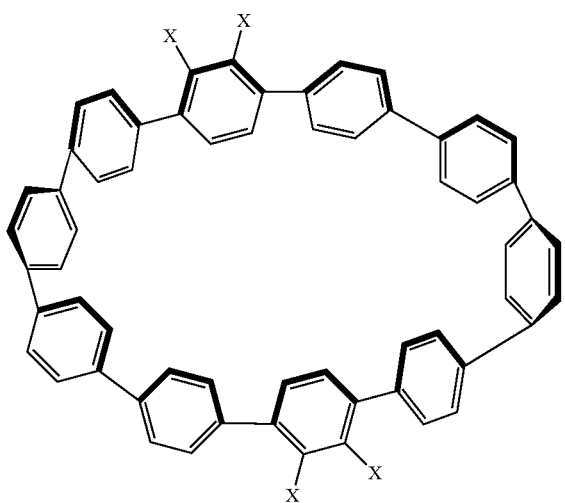
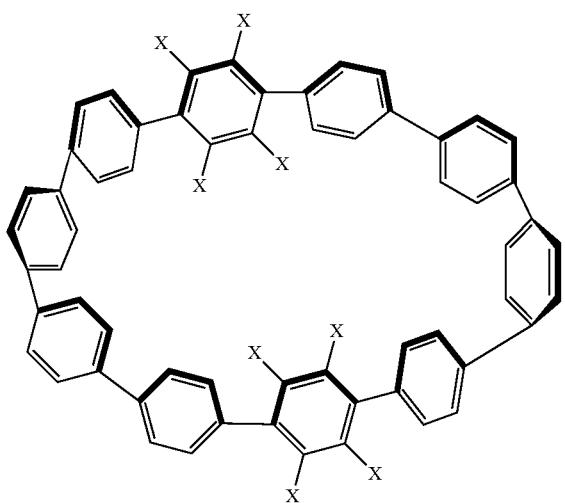

TABLE 2-continued
Representative Halogenated Nanohoop Compounds
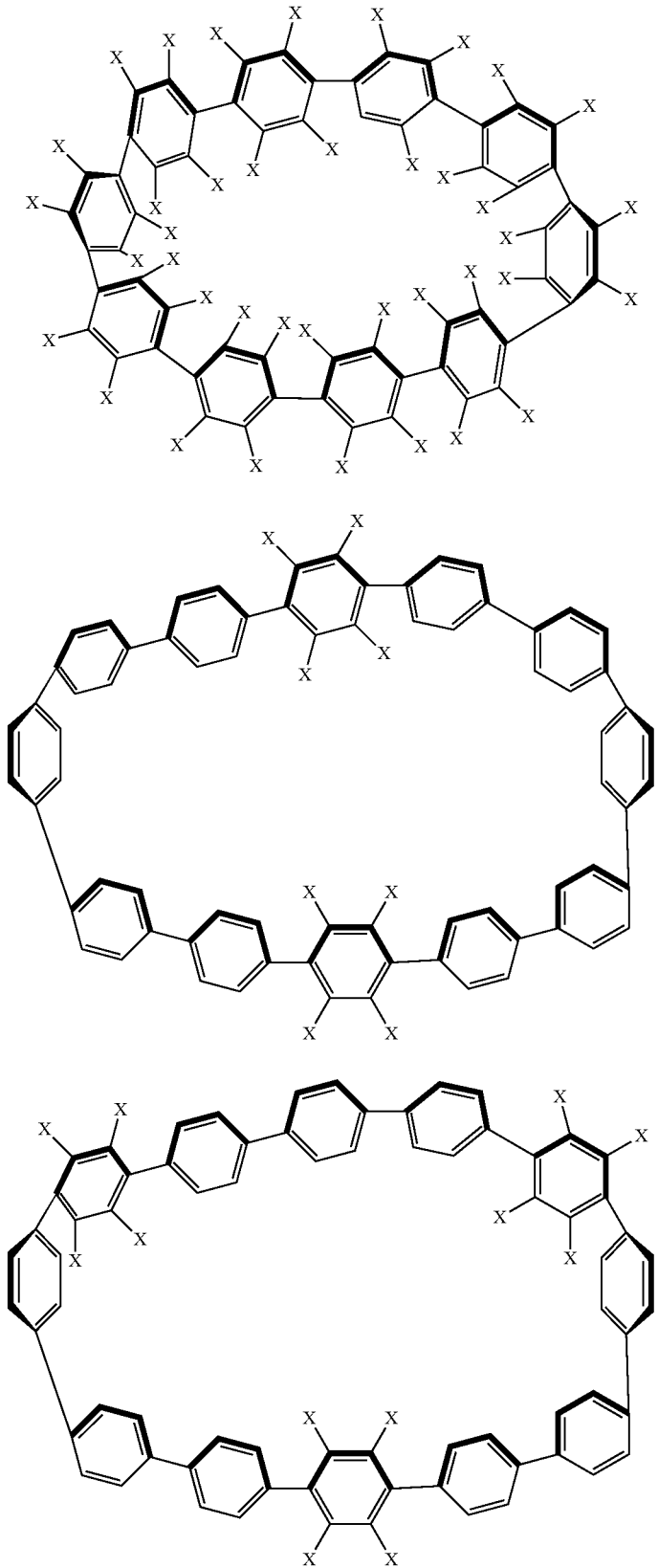

TABLE 2-continued
Representative Halogenated Nanohoop Compounds
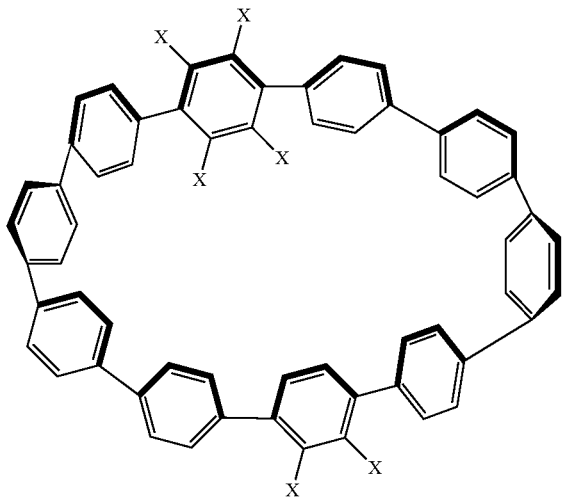
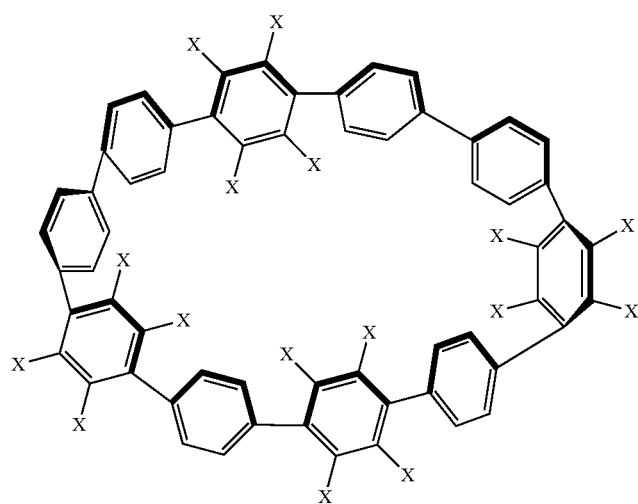
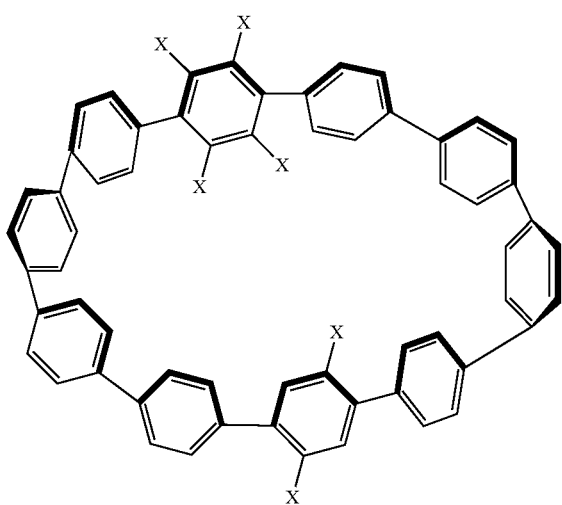

TABLE 2-continued
Representative Halogenated Nanohoop Compounds
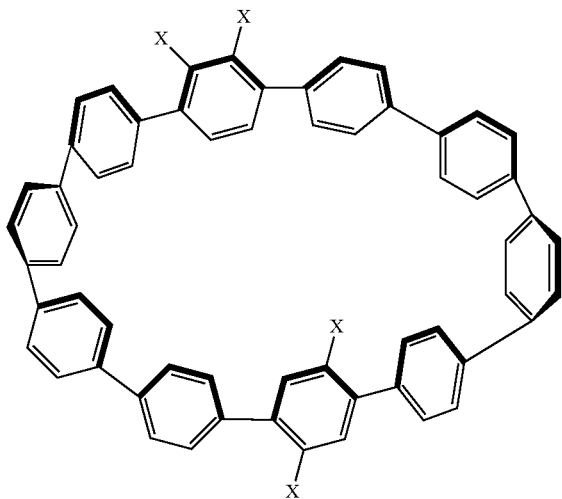
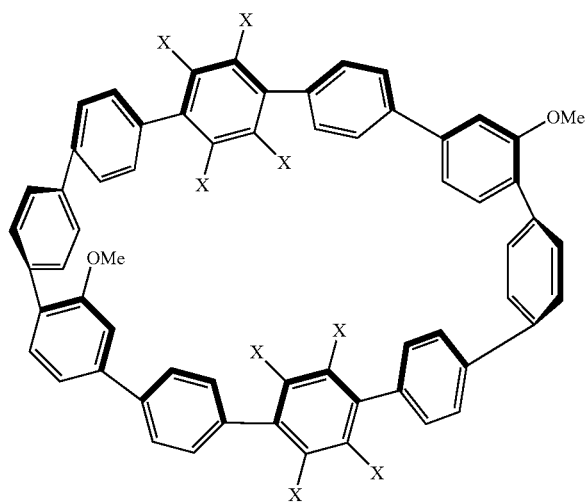
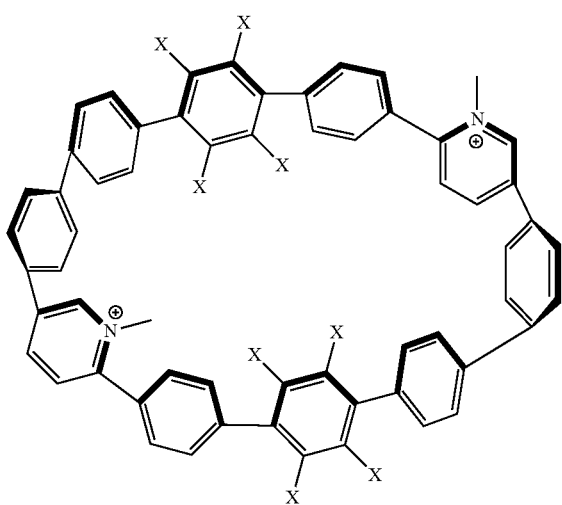

TABLE 2-continued
Representative Halogenated Nanohoop Compounds
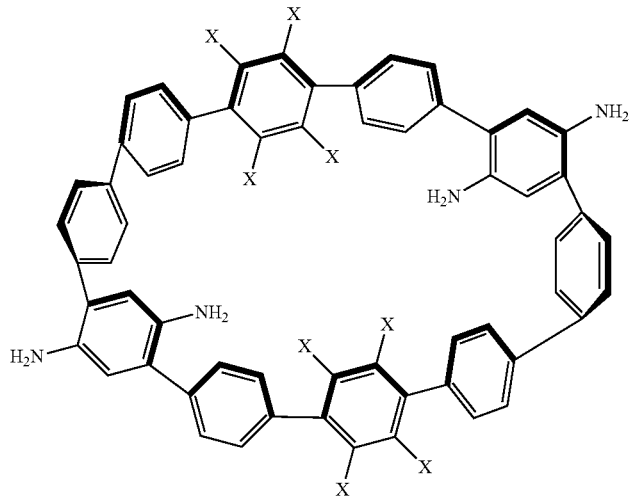
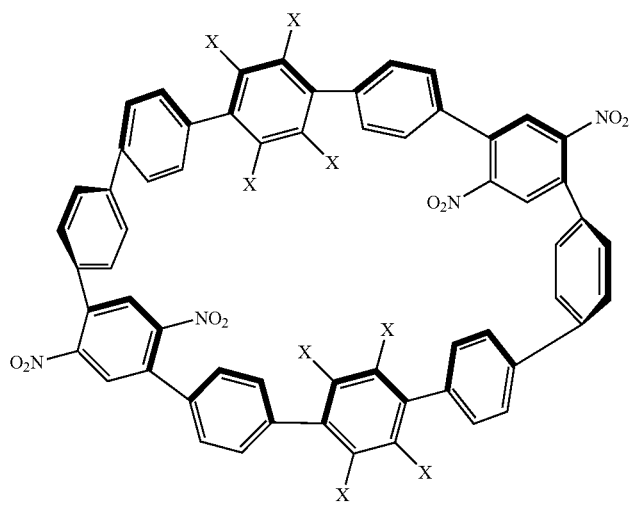
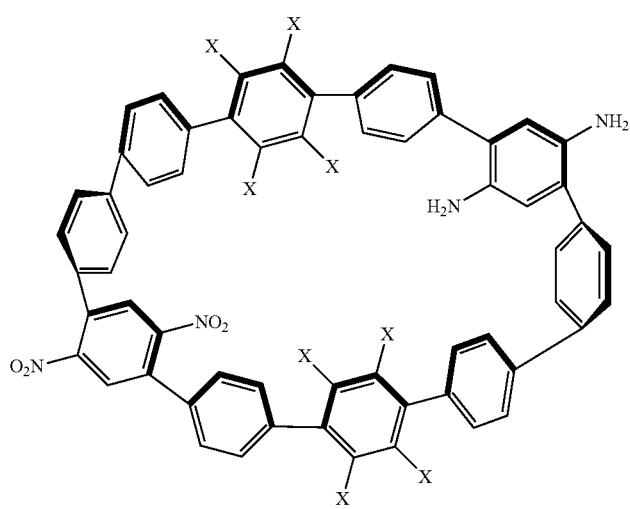

TABLE 2-continued
Representative Halogenated Nanohoop Compounds
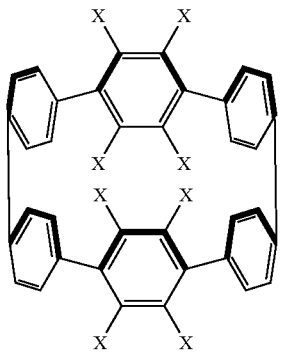
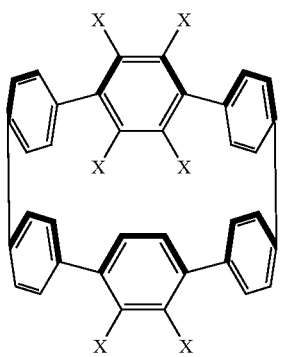
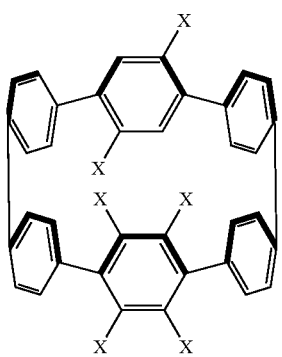
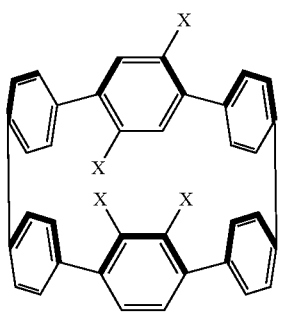

TABLE 2-continued
Representative Halogenated Nanohoop Compounds
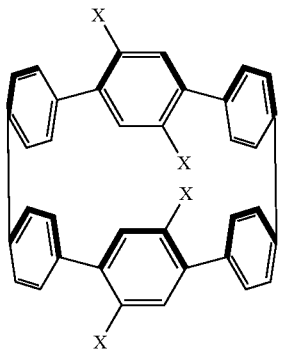
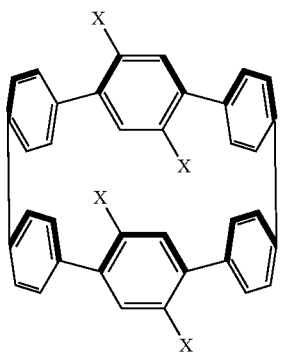
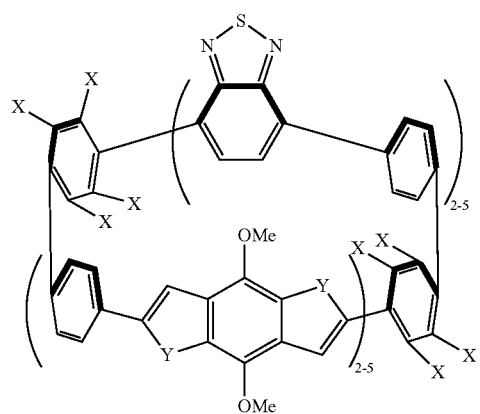
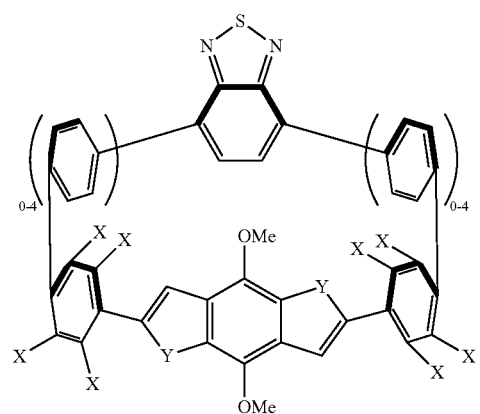

TABLE 2-continued

Representative Halogenated Nanohoop Compounds

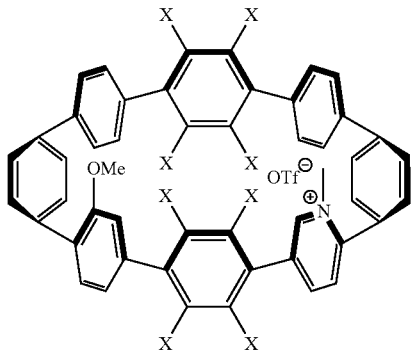

In some embodiments, the halogenated nanohoop compounds can have structures as illustrated above, wherein each X of the illustrated structures is a halogen atom independently selected from fluoro, bromo, chloro and/or iodo and each Y independently is selected from O, S, or NH. Each X can be selected to be the same or different. Also, in each of the compounds illustrated in Table 2, each of the rings making up the nanohoop skeleton that is not substituted or that is not a fused ring system is a phenyl ring. In particular disclosed embodiments, at least one X is fluoro. In some embodiments, each X is fluoro.

Representative species of halogenated nanohoop compounds are provided below by Table 3.

TABLE 3

Representative Halogenated Nanohoop Compounds

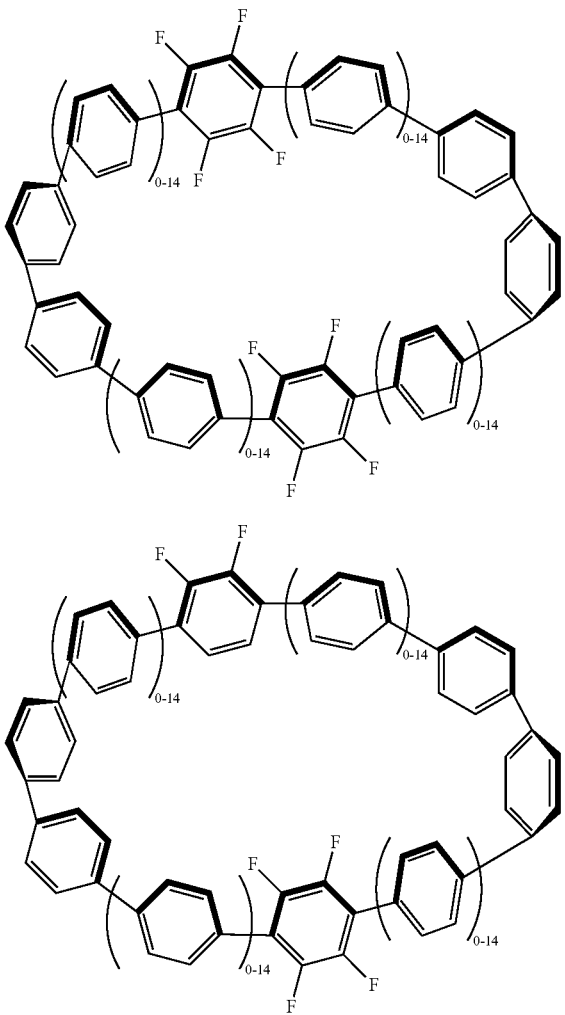

TABLE 3-continued
Representative Halogenated Nanohoop Compounds
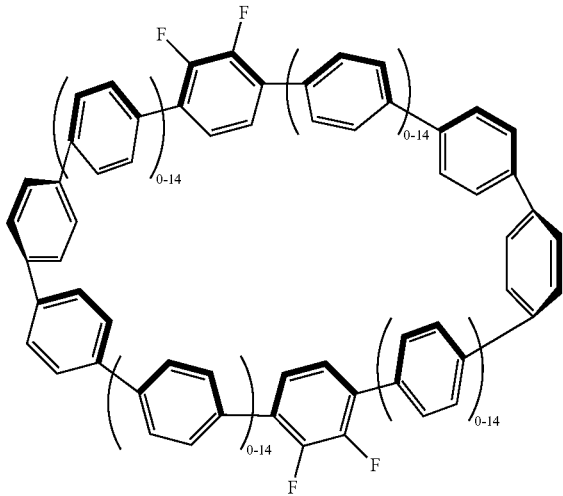
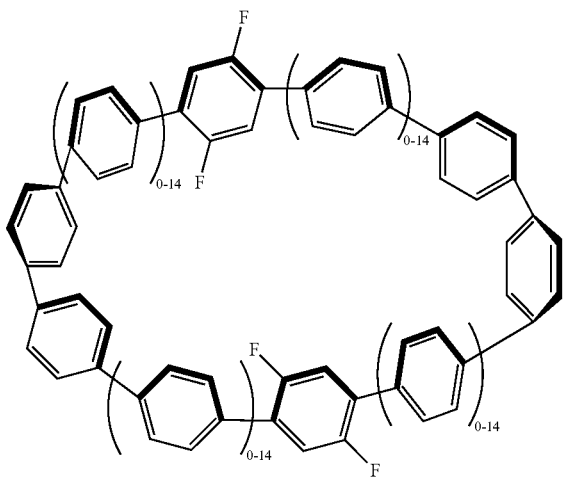
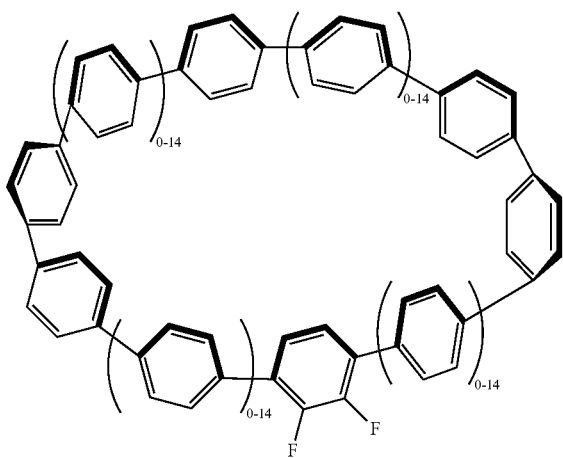

TABLE 3-continued
Representative Halogenated Nanohoop Compounds
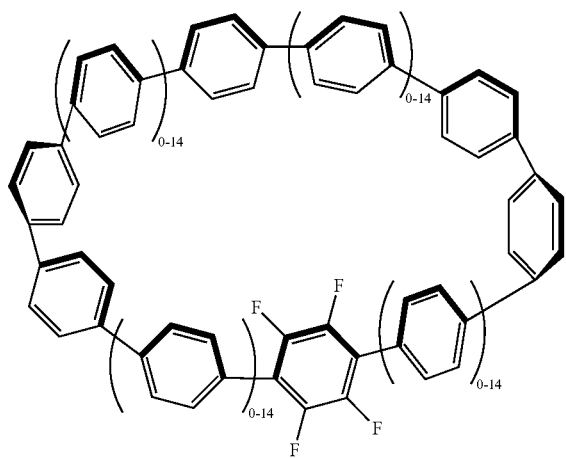
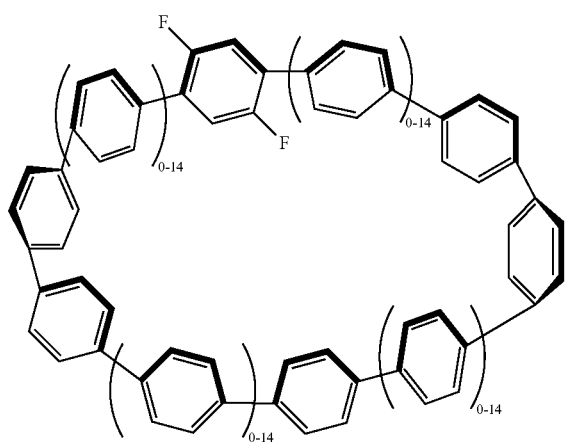
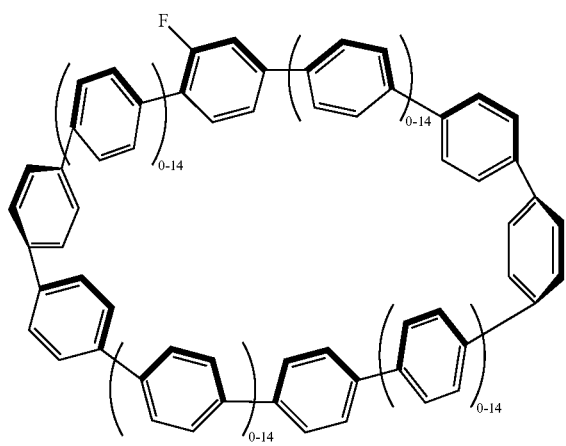

TABLE 3-continued
Representative Halogenated Nanohoop Compounds
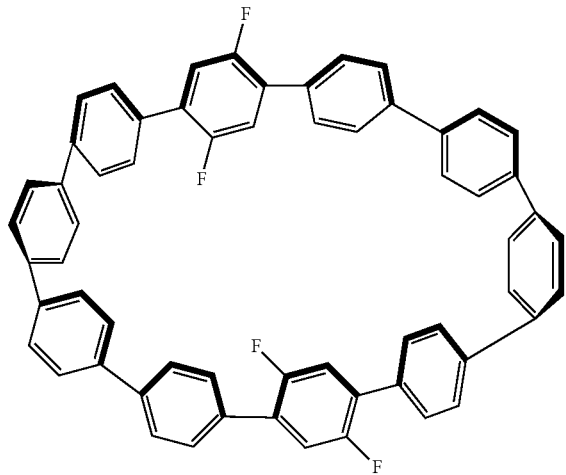
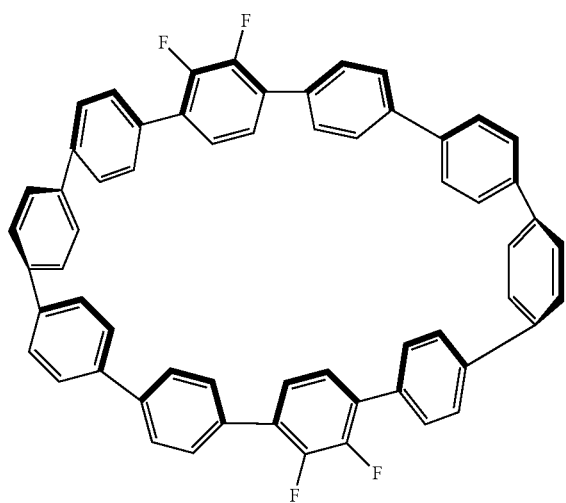
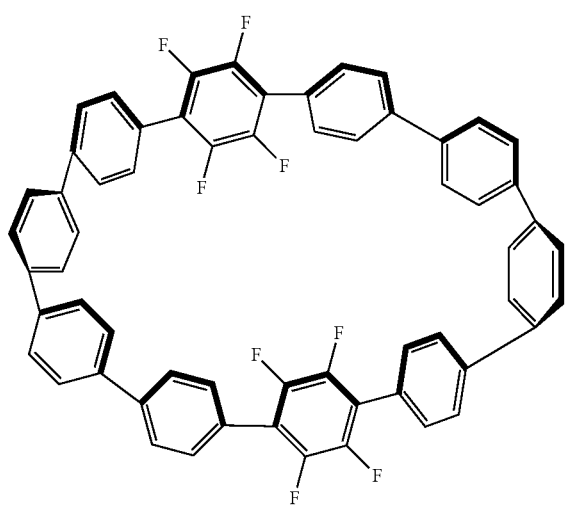

TABLE 3-continued
Representative Halogenated Nanohoop Compounds
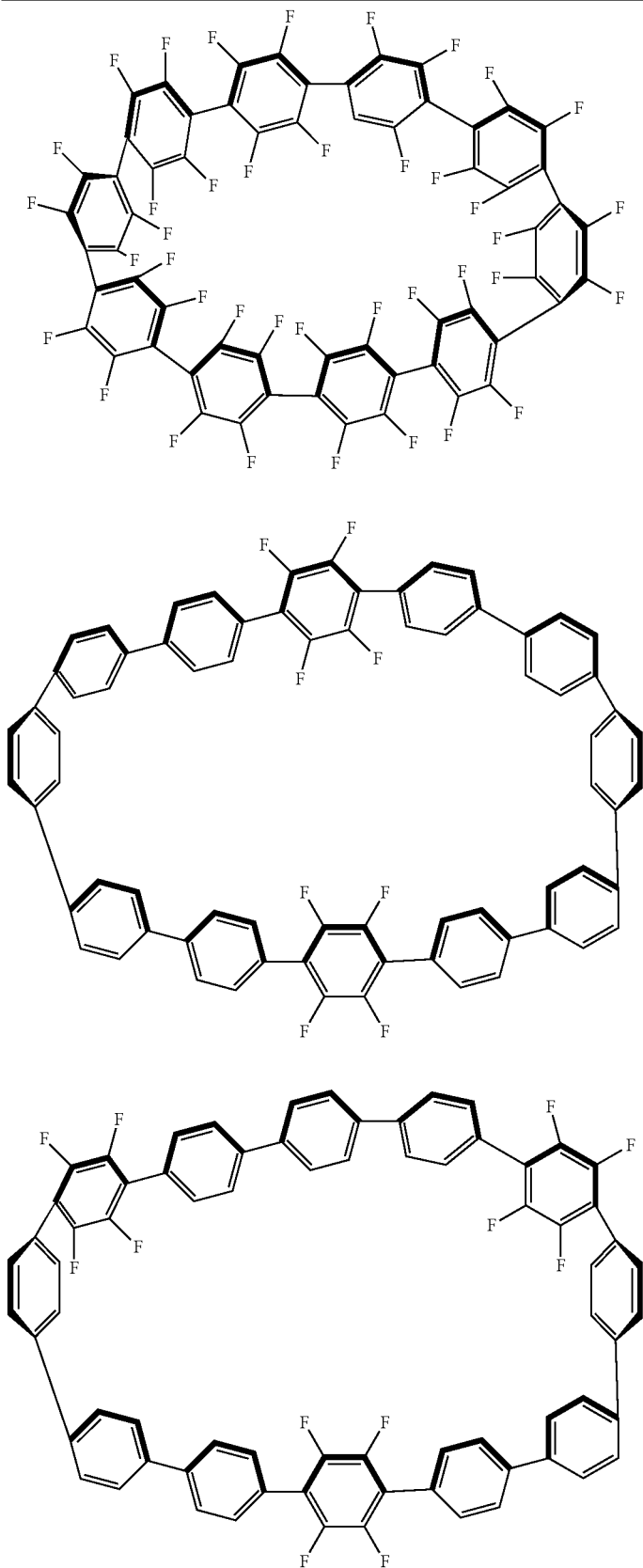

TABLE 3-continued
Representative Halogenated Nanohoop Compounds
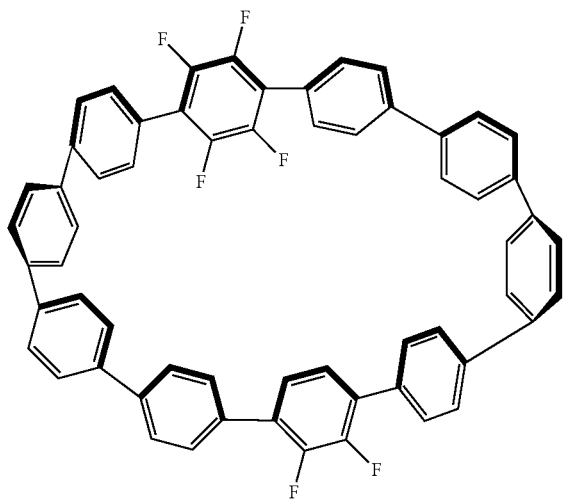
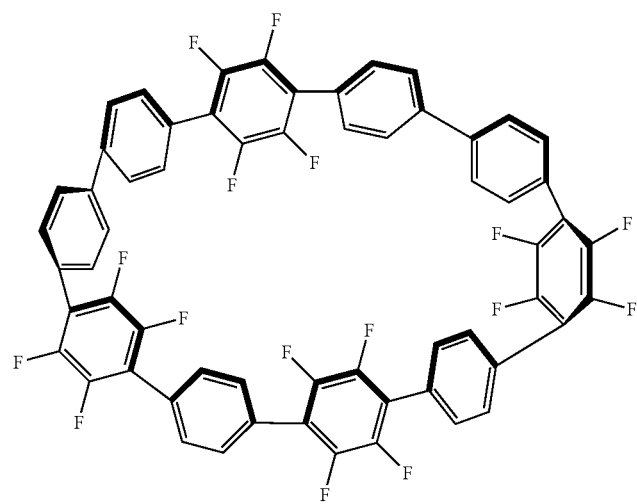
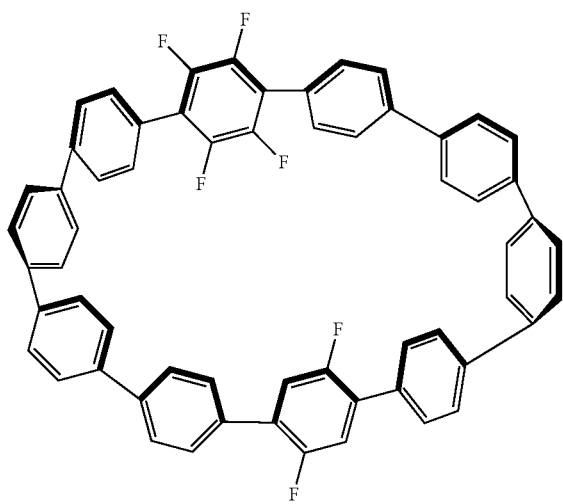

TABLE 3-continued
Representative Halogenated Nanohoop Compounds
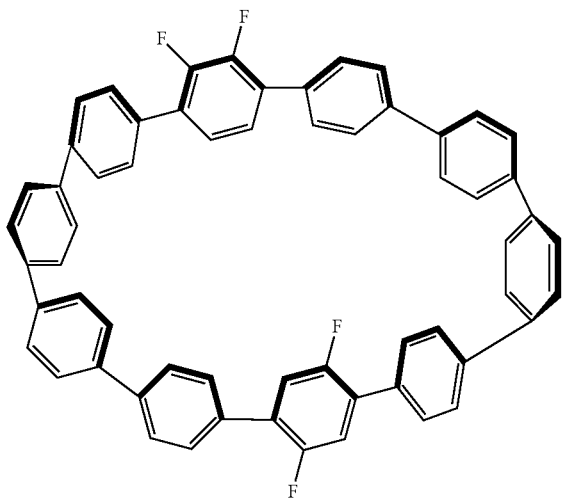
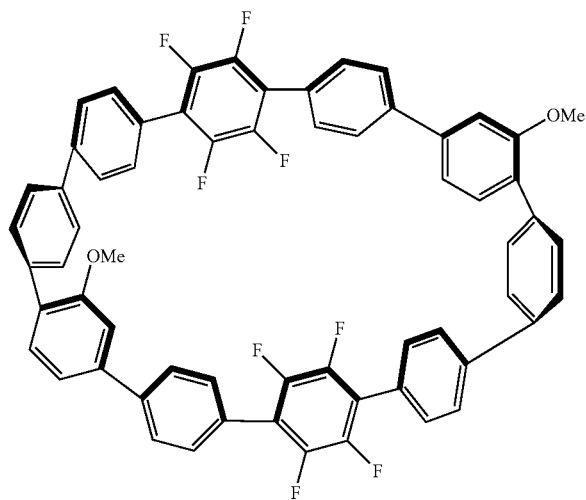
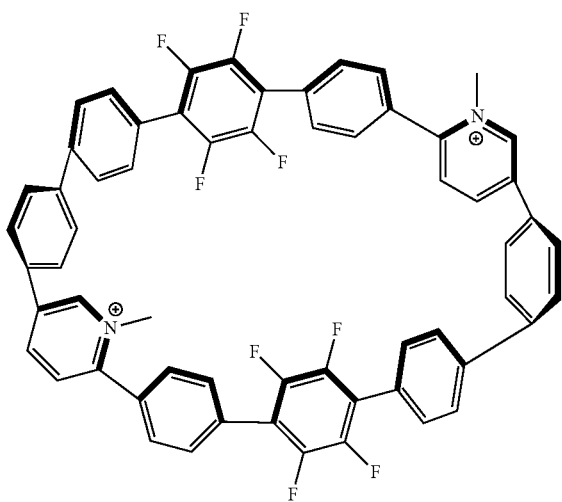

TABLE 3-continued
Representative Halogenated Nanohoop Compounds
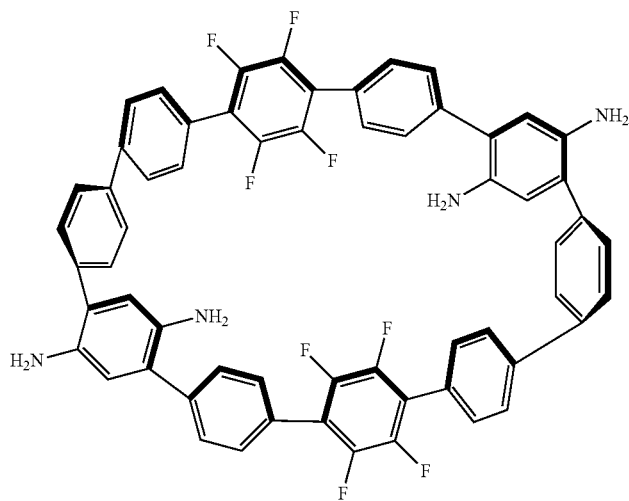
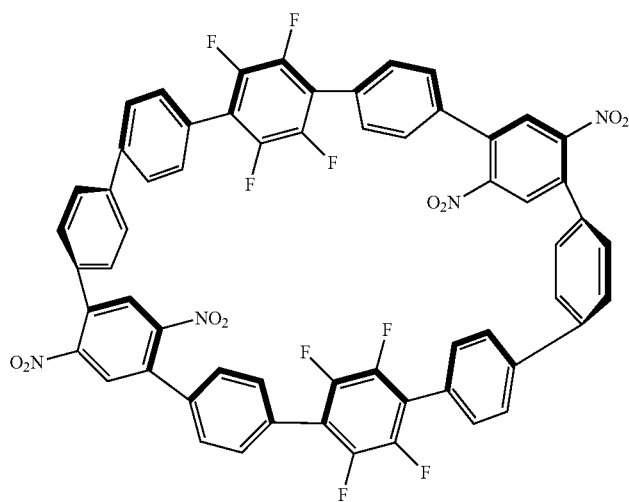
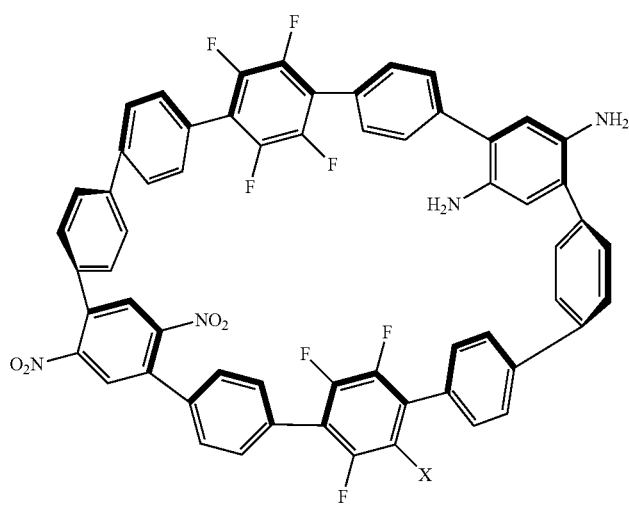

TABLE 3-continued
Representative Halogenated Nanohoop Compounds
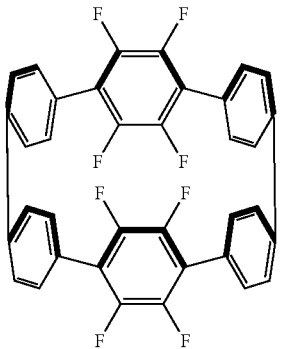
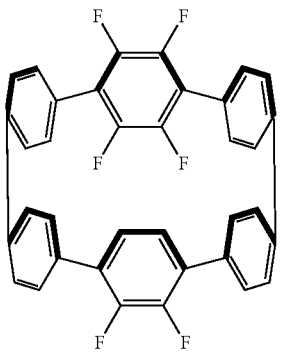
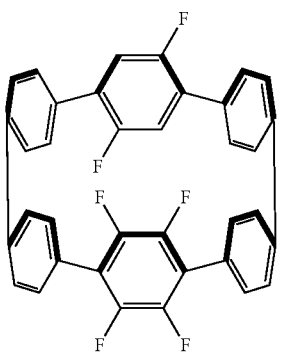
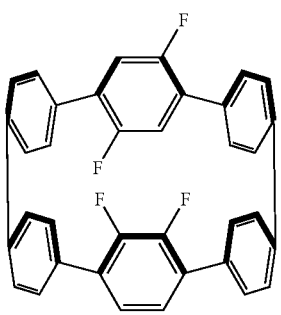

TABLE 3-continued
Representative Halogenated Nanohoop Compounds
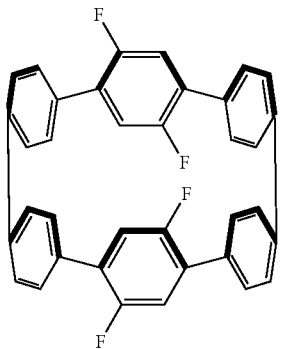
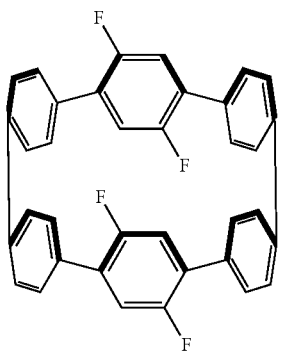
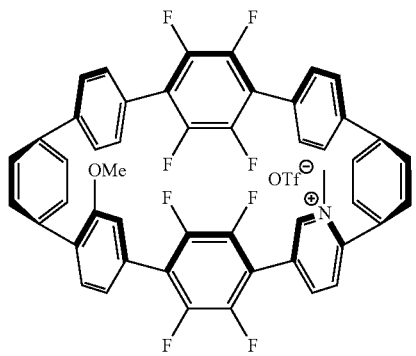
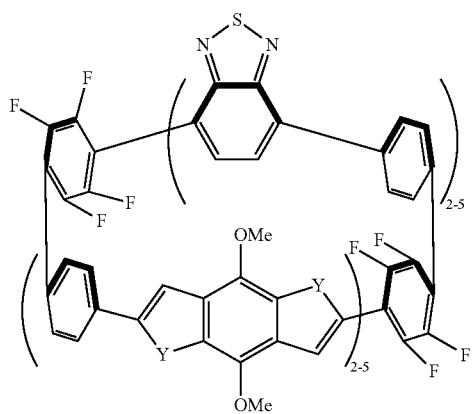

TABLE 3-continued

Representative Halogenated Nanohoop Compounds

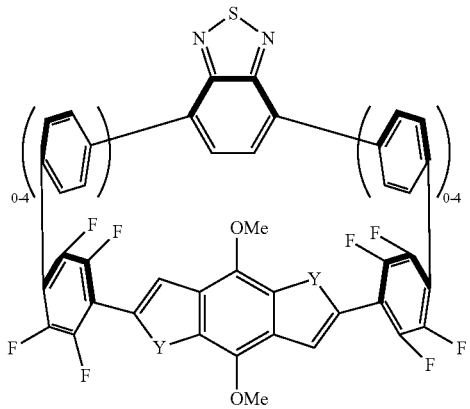

In each of the compounds illustrated in Table 3, each of the rings making up the nanohoop skeleton that is not substituted or that is not a fused ring system is a phenyl ring.

IV. Assemblies Comprising Halogenated Nanohoops

The halogenated nanohoops disclosed herein are capable of assembling into column-like structures whereby a plurality of individual nanohoop compounds align in a stacked conformation. Such assemblies typically comprise at least one halogenated nanohoop. Other halogenated nanohoops and/or non-halogenated nanohoop compounds can be included in the assembly. In some embodiments, disclosed assemblies can comprise only halogenated nanohoop compounds or they can comprise a mixture of halogenated compounds with non-halogenated nanohoop compounds, CNTs, or other cyclic structures. Assemblies formed between individual nanohoop compounds can occur through exploitation of C—H/C—X interactions (wherein X represents a halogen atom, such as fluoro, chloro, bromo, or iodo) between individual nanohoop compounds. For example, one or more halogen atoms of a halogenated nanohoop compound can interact (typically non-covalently) with one or more hydrogen atoms of another halogenated nanohoop compound, a non-halogenated nanohoop compound, a CNT, or other cyclic structure. In particular disclosed embodiments, C—H/C—F interactions are utilized to assemble individual nanohoop compounds into a column-like assembly. A representative column-like assembly is illustrated in FIG. 1.

Figure 2:
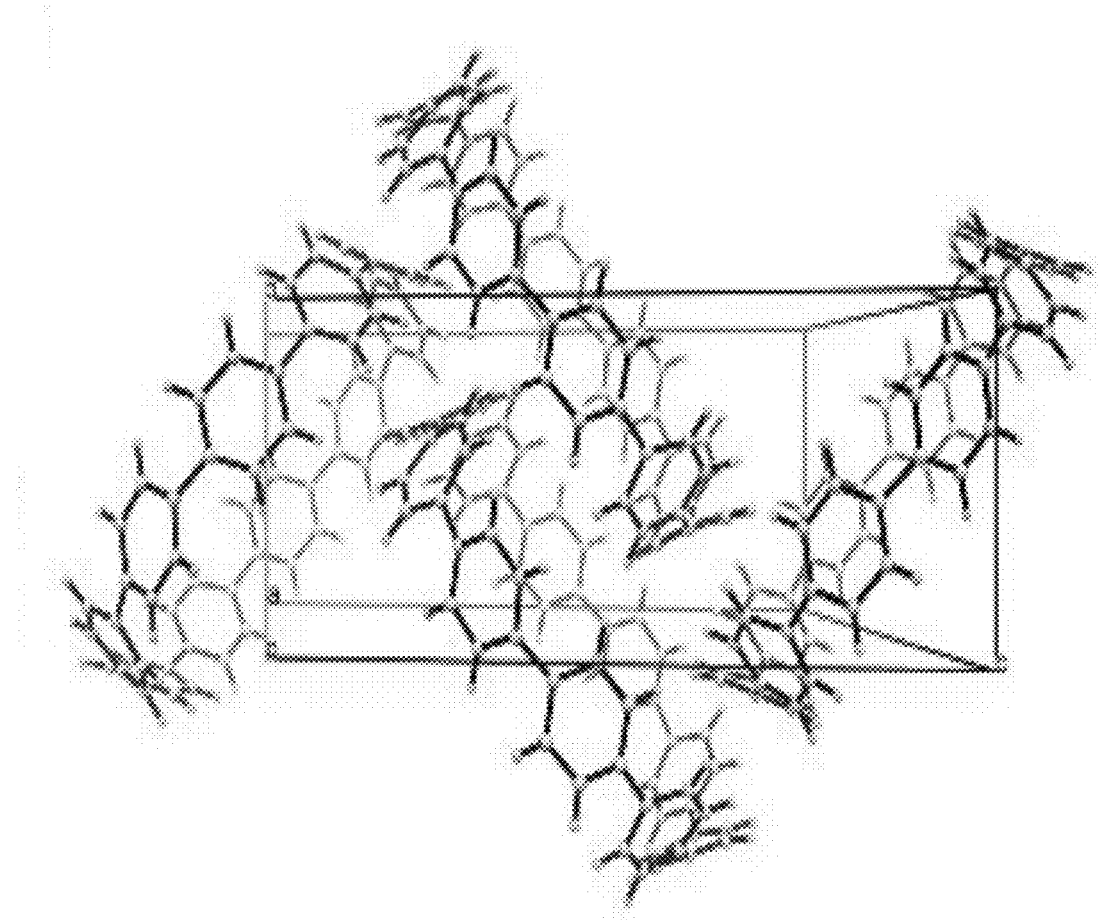
FIG. 2 is an illustration of the type of arrangement formed by non-halogenated nanohoop compounds, which illustrates that assemblies of purely non-halogenated nanohoop compounds do not form the column-like assemblies achieved by disclosed halogenated nanohoop compounds.

As illustrated by FIG. 1, the disclosed assemblies of halogenated nanohoops exhibit solid-state packing of individual halogenated nanohoops (left image) such that a uniform column-like structure is obtained (right image). By way of comparison, this column-like structure is not obtained with non-functionalized nanohoop compounds (that is, hydrocarbon nanohoop compounds that do not comprise halogen groups, or any other functional groups). Non-functionalized nanohoop compounds instead adopt a herringbone-type motif, as illustrated in FIG. 2. Thus, the halogenated nanohoop compounds provide the ability to make column-like assemblies that cannot be obtained with conventional non-functionalized nanohoop compounds.

Figure 3:
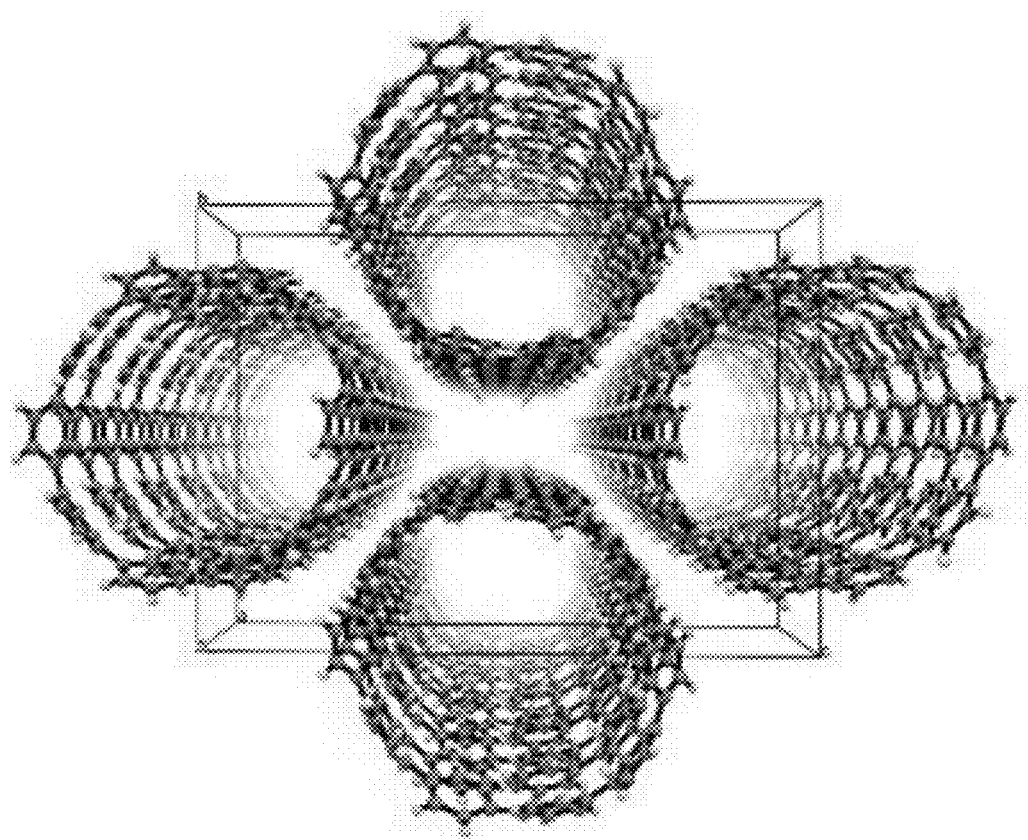
FIG. 3 is an X-ray structure illustrating uniform assemblies formed by representative nanohoop compounds and further showing that these assemblies can form networks through perhaloarene-arene non-covalent interactions.

Also, the disclosed nanohoop compounds provide functionality that allows them not only to interact with other singular nanohoop compounds to form column-like assemblies but also allows the column-like assemblies themselves to interact with other additional column-like assemblies. Thus, a plurality of column-like assemblies can associate with one another, such as through perhaloarene-arene interactions, to form a network of associated column-like assemblies. For example, an assembly as described above can interact (typically non-covalently) with one or more additional assemblies. In particular disclosed embodiments, the assemblies can interact with one another through perhaloarene-arene interactions wherein a halogenated aromatic ring of a nanohoop compound within one assembly can interact with a non-halogenated aromatic ring of another nanohoop compound within another assembly. In particular disclosed embodiments, perfluoroarene-arene interactions are utilized to associate individual assemblies into a network of assembled column-like structures. In such embodiments, one or more fluorinated aromatic rings of one or more of the nanohoop compounds of an assembly interact with one or more non-halogenated aromatic rings of one or more nanohoop compounds of another assembly. The one or more non-halogenated aromatic rings can be simple benzene rings, donor rings, and/or acceptor rings. A representative network of assembled column-like structures is illustrated in FIG. 3.

The assemblies described herein exhibit a uniformity (e.g., uniform pore diameter and uniform exterior and/or interior surfaces that are free of defects) that is not achieved using conventional carbon nanotubes or macrocyclic compounds. Also, the disclosed assemblies of halogenated nanohoops can be used to facilitate transport of chemical species through the inner pore of the assemblies, thus lending to their use in applications requiring transport mechanisms (e.g., transport through biological membranes) and/or filtering mechanisms. The nanohoop assemblies also can be used to confine chemical species within the inner pore of the assemblies and then initiate reactions within the inner pore of the assemblies. As such, the disclosed nanohoop assemblies can replace carbon nanotubes in a variety of applications (e.g., as nanoreactors, chemical sensors, biological components, etc.). Carbon nanotubes are difficult to make without myriad side-products (making isolation/purification of a single CNT difficult) and often present difficulties in introducing chemical compounds/species into the CNT core given the heterogeneous nature of CNTs and the possibility that such CNTs include mixture of CNTs having different diameters. The compounds and assemblies described herein avoid these fallbacks.

Figure 4:
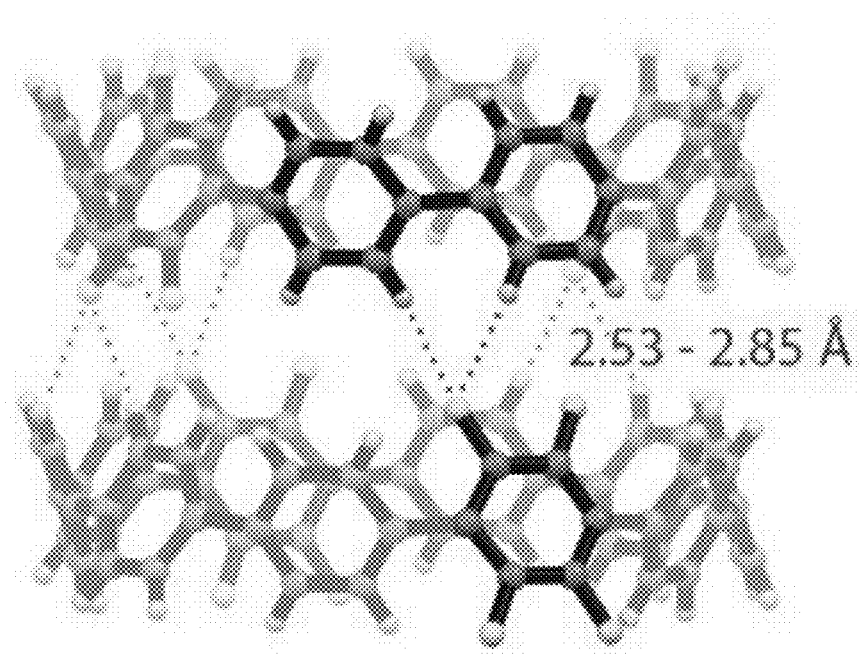
FIG. 4 is an image showing the C—H/C—X non-covalent interactions that can take place between a halogenated nanohoop compound and another nanohoop compound (which need not be halogenated) to form column-like assemblies described herein.
Figure 5:
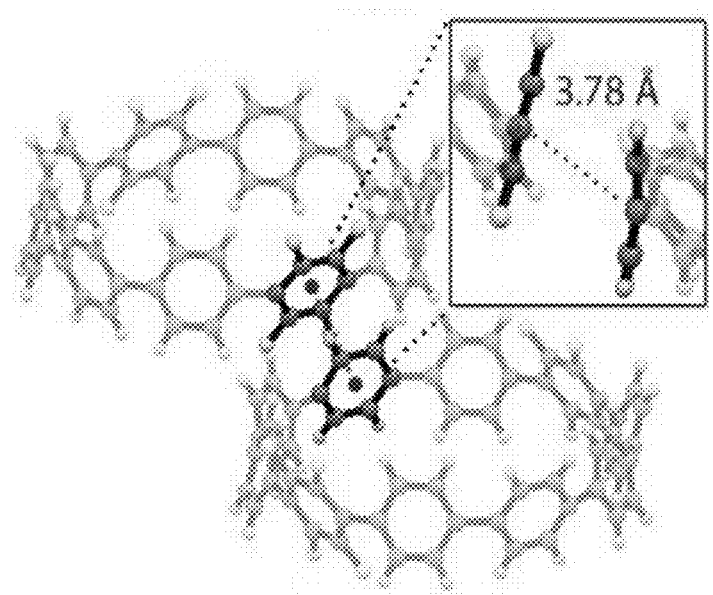
FIG. 5 is an X-ray structure of two halogenated nanohoop compounds that exhibit perhaloarene-arene non-covalent interactions.
Figure 6:
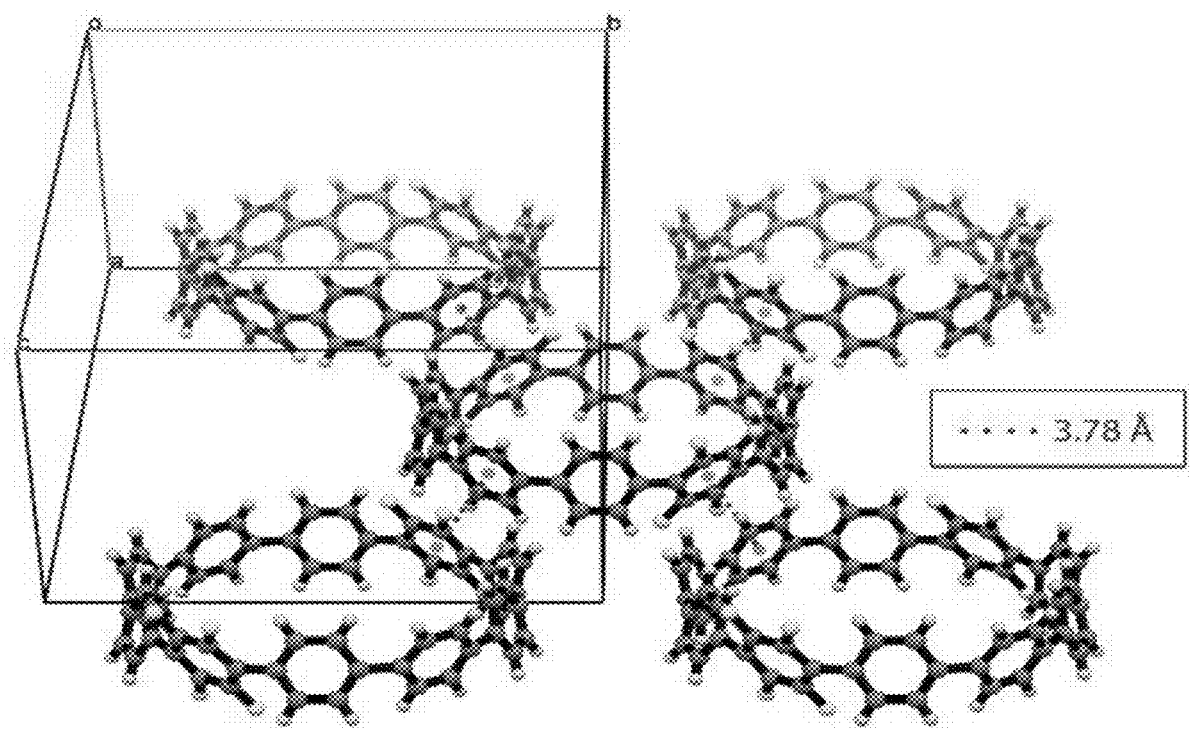
FIG. 6 is an X-ray structure of five halogenated nanohoop compounds that exhibit perhaloarene-arene non-covalent interactions.

The assemblies described herein can be formed between individual halogenated nanohoop compounds by utilizing C—H/C—X non-covalent interactions (wherein X is a halogen atom) between the individual nanohoops. The assemblies themselves also can be associated with one another through perhaloarene-arene interactions between the individual assemblies. In particular disclosed embodiments, the halogenated nanohoops are halogenated with fluorine atoms and can exhibit perfluoroarene-arene and/or C—H/C—F non-covalent interactions. In some embodiments, the C—H/C—F interaction can constitute a non-covalent interaction such that a distance of 2.50 Å to 2.90 Å (such as 2.53 Å to 2.85 Å) exists between a fluoro atom of a halogenated nanohoop compound and one or more hydrogen atoms of another halogenated or a non-halogenated nanohoop compound. Representative C—H/C—F interactions are illustrated in FIG. 4. A plurality of C—H/C—F interactions can exist between a plurality of nanohoop compounds. In some embodiments, the perfluoroarene-arene non-covalent interaction can comprise an interaction whereby a distance of 3.40 Å to 3.80 Å (such as 3.60 Å to 3.80 Å, with some embodiments being 3.78 Å) exists between a fluorinated aryl ring of a nanohoop compound of one assembly and a non-fluorinated aryl ring of a nanohoop compound of another assembly. Representative perfluoroarene-arene interactions are illustrated in FIGS. 5 and 6. A plurality of perfluoroarene-arene interactions can exist between a plurality of assemblies. In some embodiments, the electronics of the nanohoop assemblies can be altered by utilizing halogenated nanohoops comprising donor and/or acceptor rings within the nanohoop structure, such as nanohoops having structures meeting Formulas I, IIA-IIL, and IIIA-IIIC.

V. Methods of Making Halogenated Nanohoop Compounds

Methods of making halogenated nanohoop compounds are disclosed herein. Representative methods of making halogenated nanohoop compounds disclosed herein are illustrated below in the following schemes. In some embodiments, the synthesis of the disclosed halogenated nanohoop compounds utilizes halogenated precursors as building blocks, thereby avoiding potentially corrosive and/or toxic halogenation reagents.

As illustrated in Schemes 1A and 1B below, two halogenated cross-coupling partners 106 and 108 (or 106 and 110, as illustrated in Scheme 1B) comprising two cyclohexadiene moieties as "masked" benzene rings can be used as intermediates to a nanohoop precursor compound 112 or nanohoop precursor compound 116, as illustrated in Scheme 1B. Intermediate 104 can be made from a halogenated precursor compound 100 through a halogen-metal-based coupling reacting whereby the halogenated precursor compound 100 is exposed to a lithium-containing base and a halogenated coupling partner 102. After protecting the product from this reaction, intermediate 106 is obtained. Intermediate 104 also serves as a starting material to produce intermediate 108 by forming a boronate ester from the intermediate. As illustrated by Scheme 1A, additional A and B rings optionally can be added to intermediate 108 using suitable cross-coupling conditions to produce boronate ester 110. The two intermediates 106 and 108 (or intermediate 106 and 110, as illustrated in Scheme 1B) can then be cross-coupled using suitable cross-coupling conditions, such as transition metal-mediated cross-couplings (e.g., Suzuki-Miyaura cross-coupling conditions). The curved nature of these intermediates can provide a sufficient strain energy for forming the desired nanohoop compound. Utilizing this inherent reactivity and an acid-based deprotection step of nanohoop precursor compounds 112 and 116, the desired halogenated nanohoop compounds 114 and 118 can be obtained (as illustrated in Scheme 1B).

Scheme 1A

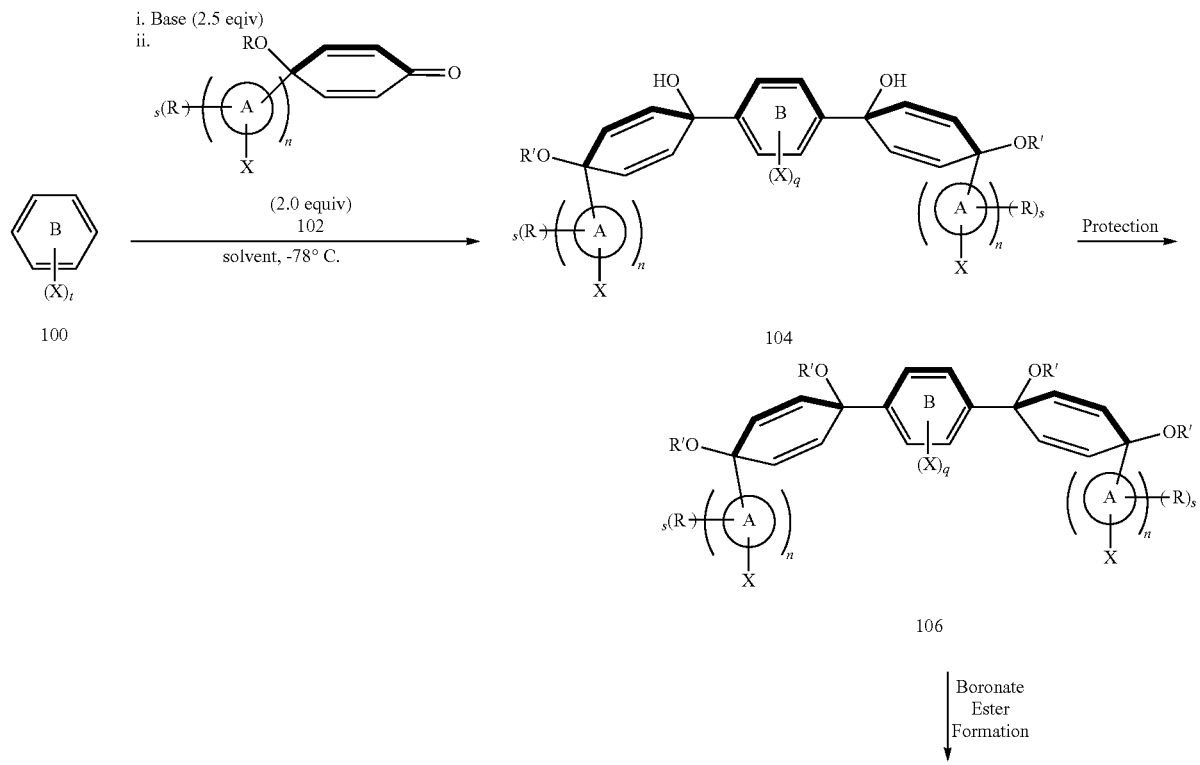

-continued
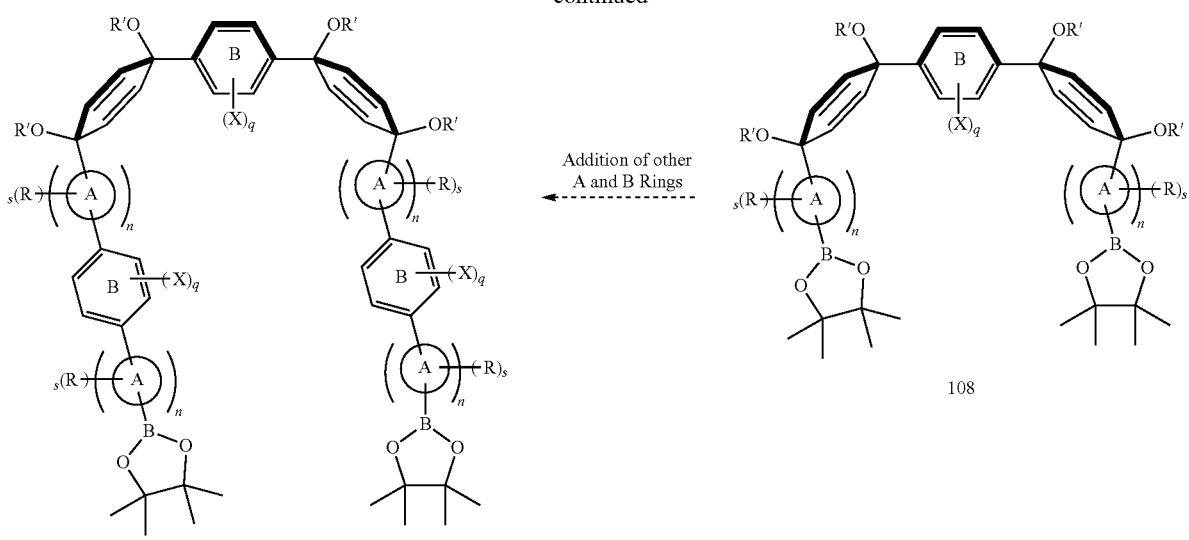
Scheme 1B
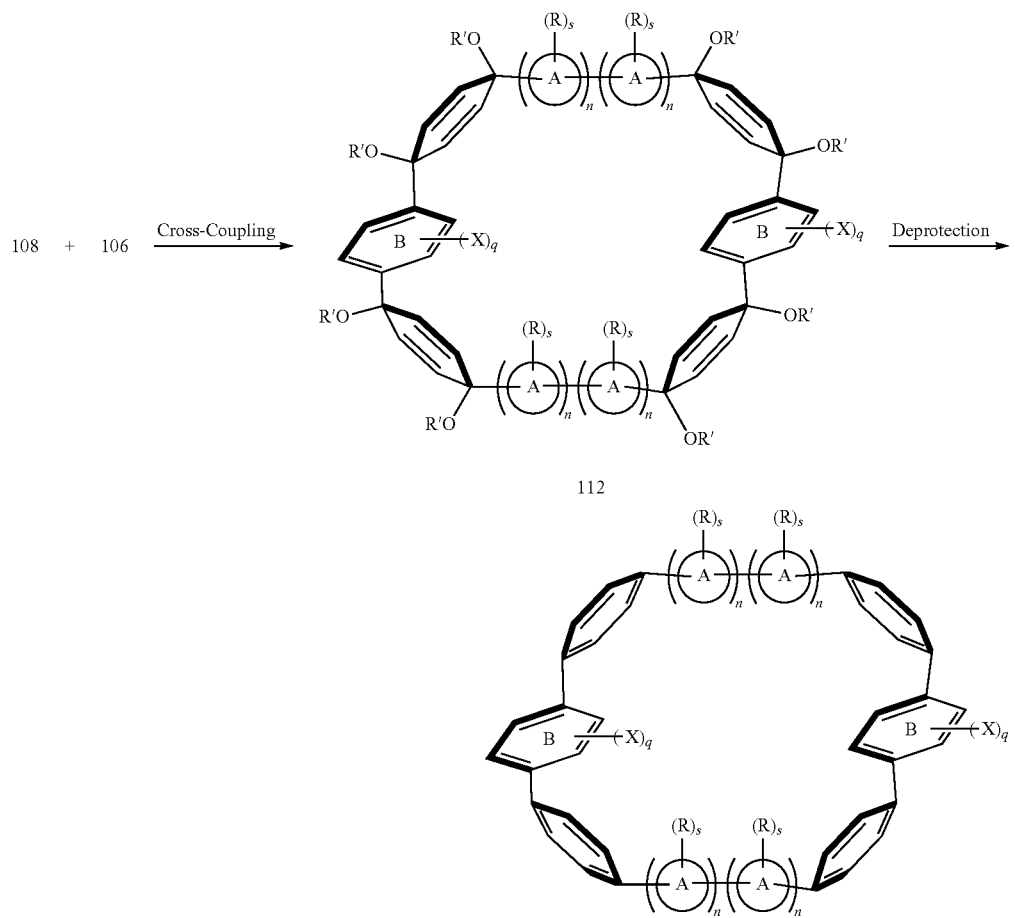

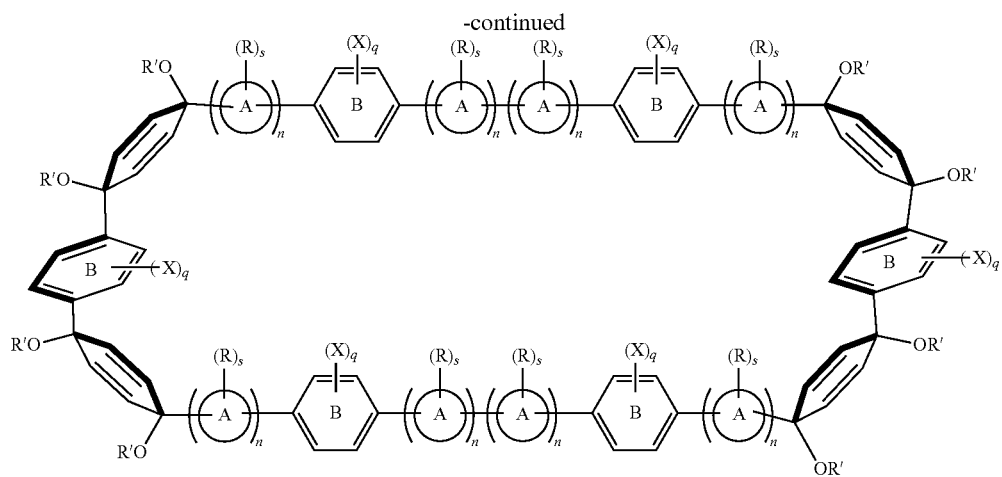

116

Deprotection

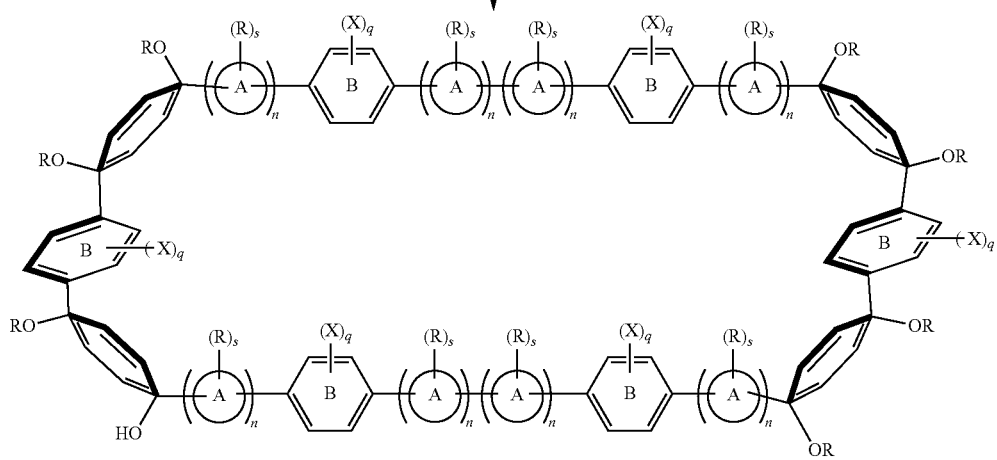

118

With reference to Schemes 1A and 1B, each R independently can be a protecting group selected from silyl protecting groups (e.g., TES, TMS, TBS, TBDPS, TIPS, and the like). The other variables in Schemes 1A and 1B above are as disclosed for the formulas described herein.

An additional embodiment of a cross-coupling partner that can be used to make a halogenated nanohoop, including a method of making this cross-coupling partner, is illustrated in Scheme 1C below. In some embodiments, compound 123 can be cross coupled with compound 108 or compound 110 to form a halogenated nanohoop.

Scheme 1C

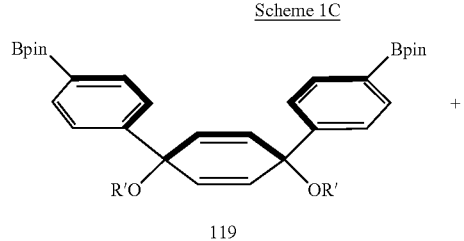

119

-continued

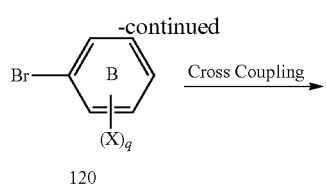

120

Cross Coupling

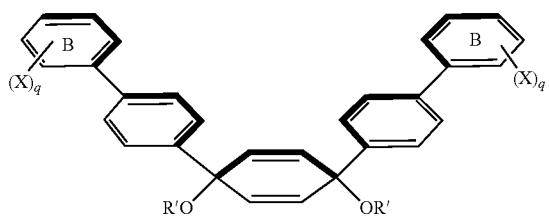

122

Iodination

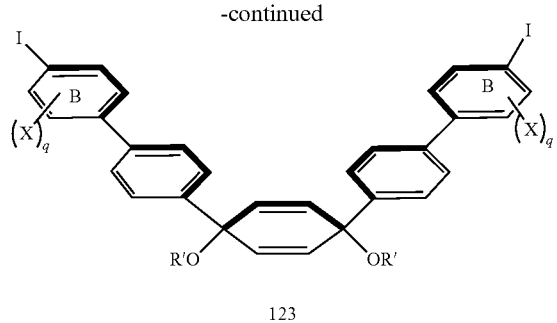

123

In a particular embodiment of the method described above in Schemes 1A and 1B, commercially available and inexpensive 1,2,4,5-tetrafluorobenzene (200) is used as a building block (Scheme 2). As illustrated below in Scheme 2, two 1,2,4,5-tetrafluorobenzene-embedded Suzuki-Miyaura cross-coupling partners 206 and 208, which include two cyclohexandienes as "masked" benzene rings, are used as the primary strain-building intermediates. Fluorinated [10] CPP compound 212 is made by first preparing cross-coupling partners 206 and 208 (Scheme 2). In some embodiments, when 1,2,4,5-tetrafluorobenzne (200) is treated with excess lithium diisopropylamine (LDA) in the presence of two equivalents of aryl-bromide 202, a diol is readily formed, which, after protection of the resulting diols with chlorotriethylsilane (TESCl), provides dibromide 206. Next, dibromide 206 and diboronate 208 are cross-coupled under dilute conditions (e.g., 2 mM) to give macrocycle 210. In some embodiments, any difficulties associated with deprotecting macrocycle 210 can be prevented by deprotecting macrocycle 210 with acetic acid, which provides a deprotected. Aromatization of the resulting free alcohol-containing macrocycle provides the final fluorinated nanohoop 212. A representative method for making additional cross-coupling partners is illustrated in Scheme 3 and a representative method for coupling these partners is shown in Schemes 4 and 5.

Scheme 2

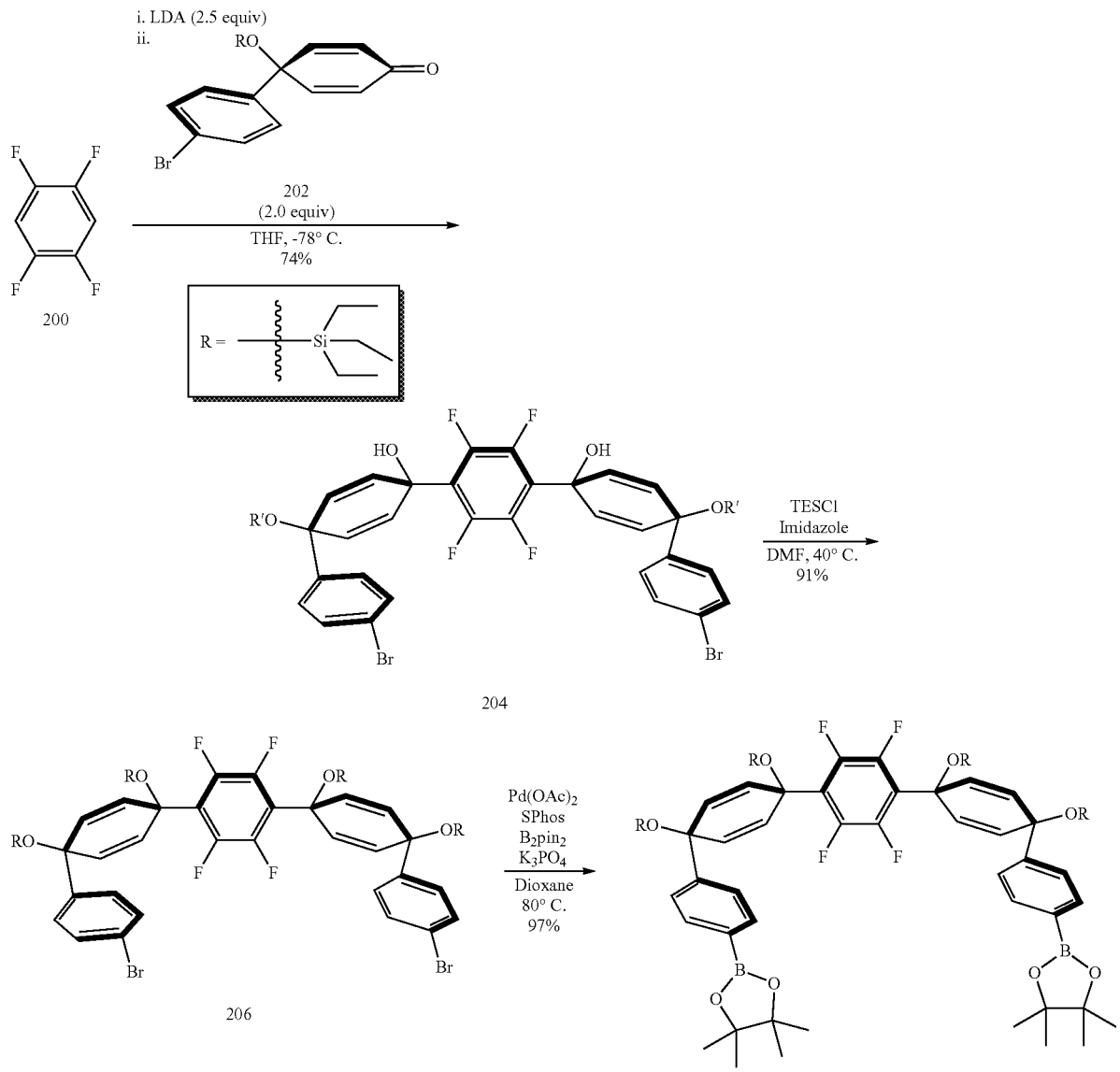

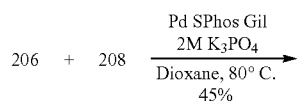
-continued
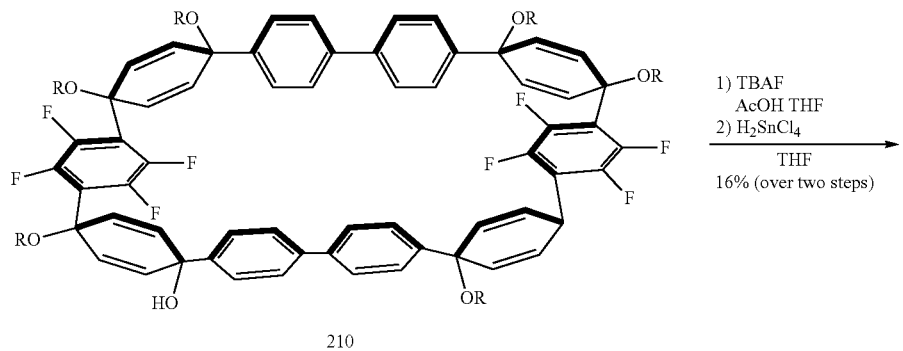
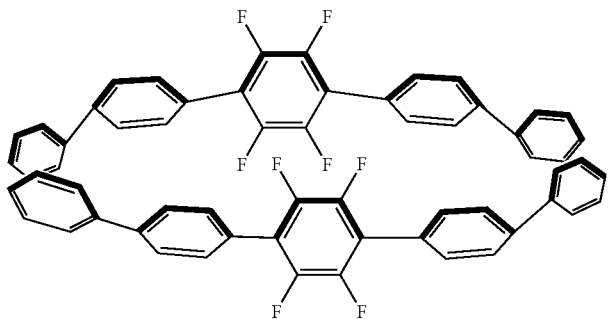
Scheme 3
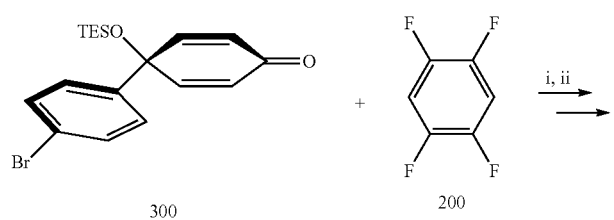
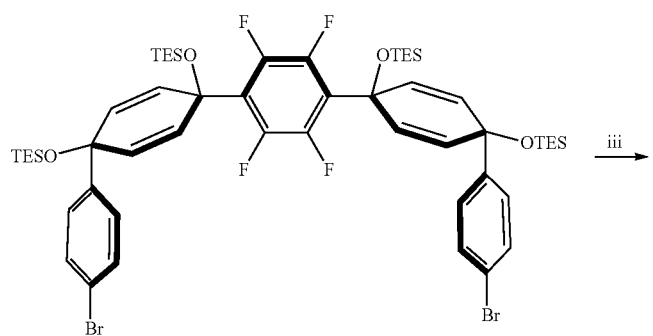

-continued
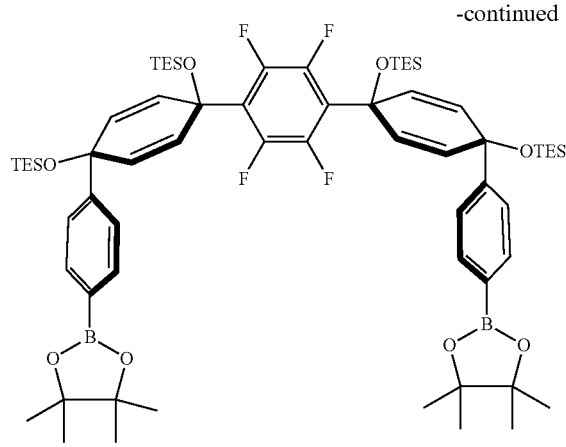
304
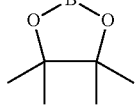
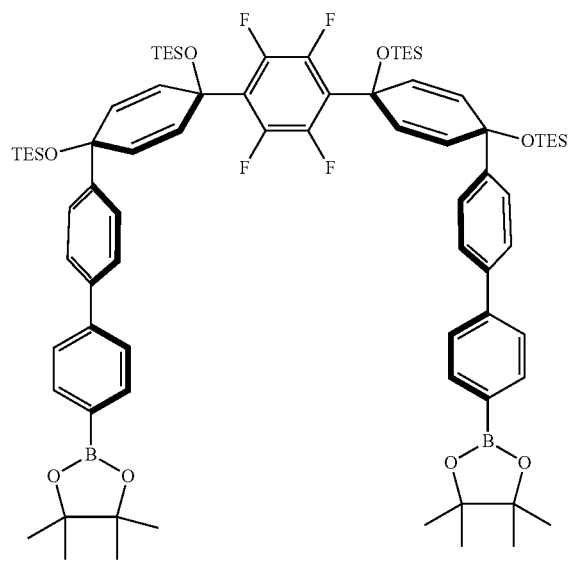
306
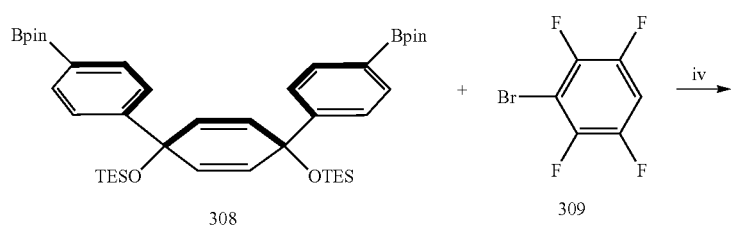

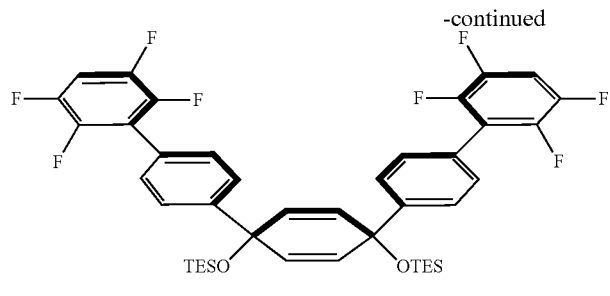
310
↓ v
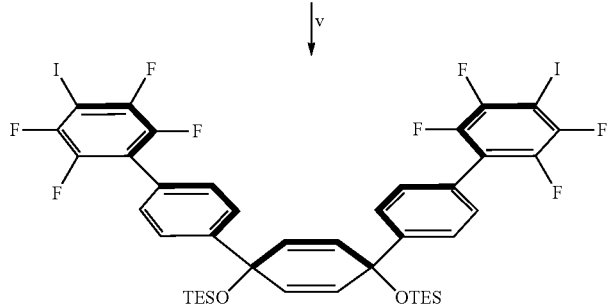
312
With reference to Scheme 3, the following conditions can be used: i) LDA, AcOH/MeOH, THF, −78° C.; ii) TESCl, Imidazole, DMF, 40° C.; iii) Pd(OAc)$_2$, SPhos, B$_2$pin$_2$, K$_3$PO$_4$, 1, 4-dioxane, 80° C.; iv) Pd(dppf)Cl$_2$, 2M K$_3$PO$_4$ (aq), 1, 4-dioxane, 80° C.; and v) LDA, I$_2$, Na$_2$S$_2$O$_3$, THF, −78° C.
Scheme 4
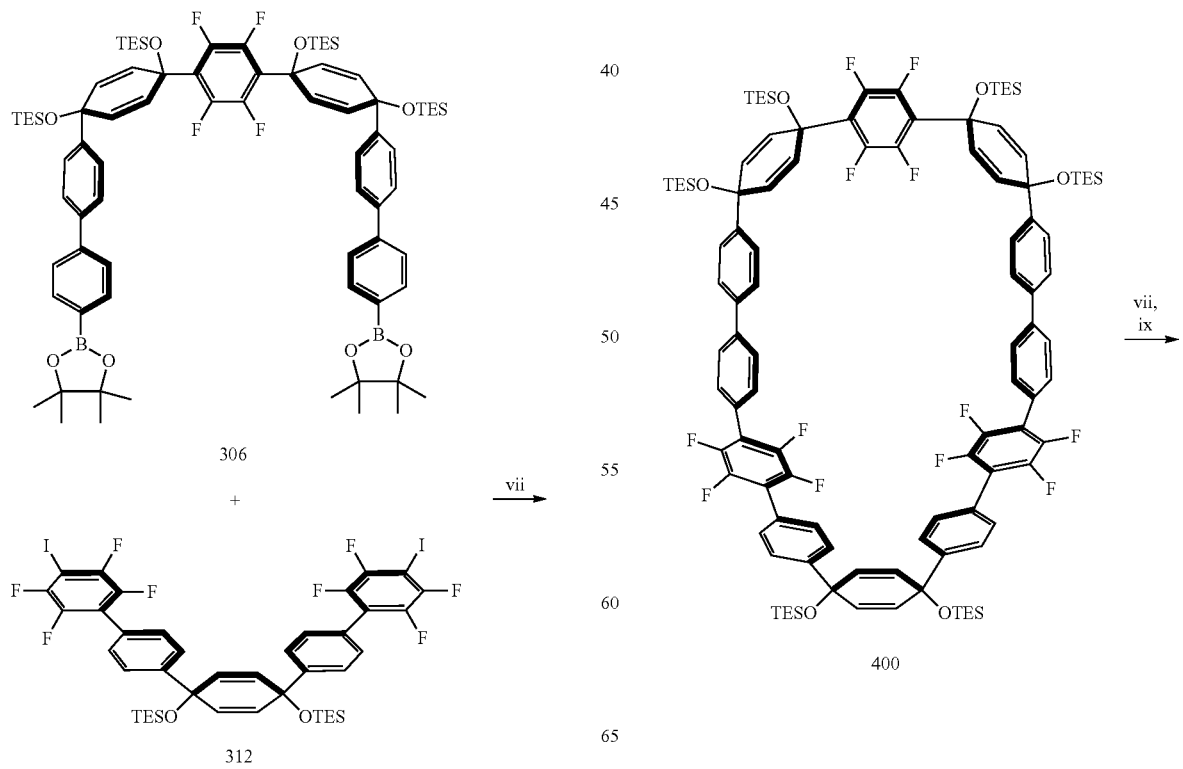

-continued

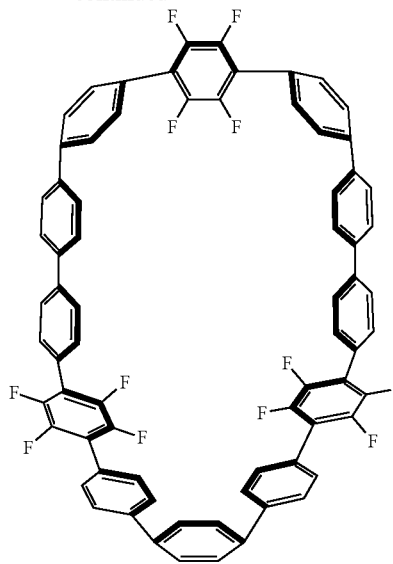

402

-continued

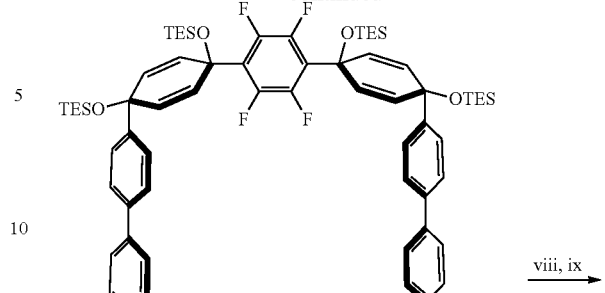

502

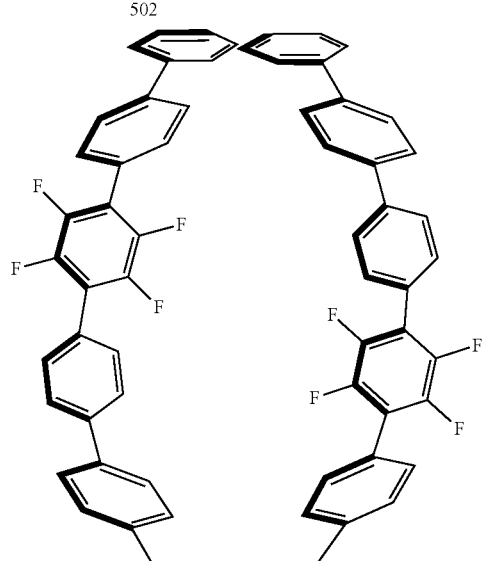

504

Scheme 5

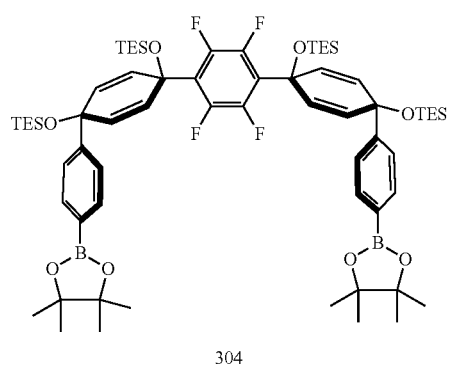

304

+

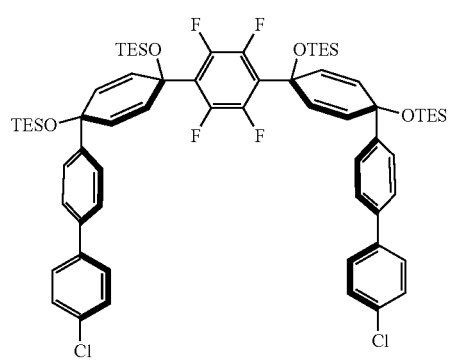

500

→ vii

With reference to Schemes 4 and 5, the following conditions can be used: vii) Pd SPhos GII, 2M $K_3PO_4$, 1,4-dioxane, 80° C., 1-3 hours; viii) AcOH, TBAF, THF, room temperature, 18 hours; and ix) $H_2SnCl_4$, THF, room temperature, 18 hours.

VI. Methods of Using Halogenated Nanohoops and Assemblies

The halogenated nanohoop compounds and assemblies disclosed herein can be used in a variety of different applications. The assemblies described herein can exist as solid-state porous materials that can serve as transport facilitators, synthetic templates (e.g., nanoreactors), and even act as electrically conductive materials. As such, the halogenated nanohoop compounds and assemblies thereof can be used in different biological and/or chemical systems and even in energy storage devices.

In particular disclosed embodiments, the porous nature of the assemblies described herein allow the halogenated nanohoops and assemblies thereof to be used in applications where porous structures can be utilized. For example, the halogenated nanohoops and assemblies thereof can host chemical compounds within the central pore of each assembly and even in regions formed between different assemblies (such as in a network of assemblies). As such, the disclosed assemblies (and assembly networks) can function as nanoreactors wherein different chemical modifications can be made to a guest species while confined within a pore of the nanoreactor. Exemplary guest species that can be hosted within the disclosed nanoreactors include, but are not limited to, chemical compounds that can be hydrogenated using the nanoreactors (e.g., benzene, α-ketoesters, α,β-unsaturated acids, aldehydes, olefins, carbonyls, acetates, carbon dioxide, carbon monoxide, and the like); chemical compounds that can be oxidized, dehydrogenized, and/or hydroxylated using the nanoreactors (e.g., methane, carbon monoxide, benzyl alcohols, styrene compounds, alkenes, silanes, aromatic compounds, cycloalkanes, and the like); chemical compounds that can be used for ammonia synthesis and/or decomposition (e.g., nitrogen gas/hydrogen gas and ammonia); chemical compounds that can be polymerized (e.g., olefin-containing compounds); chemical compounds that can be hydrosilylated (e.g., alkynes); chemical compounds that can undergo cycloadditions or cross-compound reactions (e.g., alkynes, azides, aryl halides, boronic acids); chemical compounds that can undergo photodegradation (e.g., methylene blue); chemical compounds that can be electrochemically reduced or oxidized (e.g., methanol, oxygen, hydrazine, and the like); and chemical compounds that can undergo substitution reactions (e.g., alkenes, acetamides, and the like).

The nanoreactors disclosed above can be used to perform any of these chemical modifications with good selectivity and yield and also can increase reaction rates (e.g., by increasing local concentration and/or effective pressure within the confined reaction environment; that is, the pore(s) of the nanoreactor) and improve reaction kinetics. In some embodiments, the nanoreactors disclosed herein provide the ability to conduct chemical modifications while avoiding harsh reaction conditions (e.g., excessive heat, toxic chemicals, excessive reagent amounts, and the like). In yet some other embodiments, the nanoreactors are sufficiently robust and can serve as a shielding environment so that harsh conditions (e.g., high temperatures) can be used without negatively impacting the nanoreactor or the guest species within the nanoreactor. The disclosed nanoreactors also can be used for reactions utilizing catalysts as they can serve as a platform upon which catalysts can anchor and thereby can stabilize the catalysts and prolong their reactivity (by avoiding sintering, coalescence and/or poisoning). In particular disclosed embodiments, the nanoreactors can be used to convert small molecule inorganic precursors into inorganic nanowires, such as silicon nanowires. Also, they could be used to convert small aromatic molecules into longer graphene ribbons.

In some embodiments, the halogenated nanohoop compounds and assemblies thereof can be used as transport facilitators. For example, the halogenated nanohoop compounds can be made to have particular inner diameters and when these compounds are assembled into column-like structures, they can provide column-like assemblies that have a defined inner pore through which chemical species can travel. Such transport facilitators are useful as, for example, biological channels that facilitate transport across membranes. In some embodiments, the assemblies described herein (or assembly networks) can be used to selectively transport molecules (e.g., ions and/or drug molecules) across biological membranes, wherein the selective transport is controlled by the inner pore diameter, the polarity of the rings of the individual nanohoop compounds making up the assemblies, functional groups located on rings of the individual nanohoop compounds making up the assemblies, and/or the electrochemical nature of the assemblies. In some embodiments, the nanohoop compounds and assemblies thereof can be modified to comprise a detectable moiety, such as a fluorescent moiety. Such embodiments can be used, for example, in DNA sequencing.

In some embodiments, the assemblies can be used for mass transport of fluids (e.g., liquid or gas), chemical compounds (e.g., ionic species, such as potassium, sodium, and the like), and combinations thereof. As the disclosed halogenated nanohoops are readily synthesized on large scale and further can be made with a pre-defined inner diameter and good uniformity, assemblies made from these halogenated nanohoop compounds are readily implemented into a variety of biological contexts (e.g., as protein channels, biological lumens, and the like). Also, the surface chemistry of the assemblies can be varied by modifying the precursors used to make the halogenated nanohoops.

Figure 7:
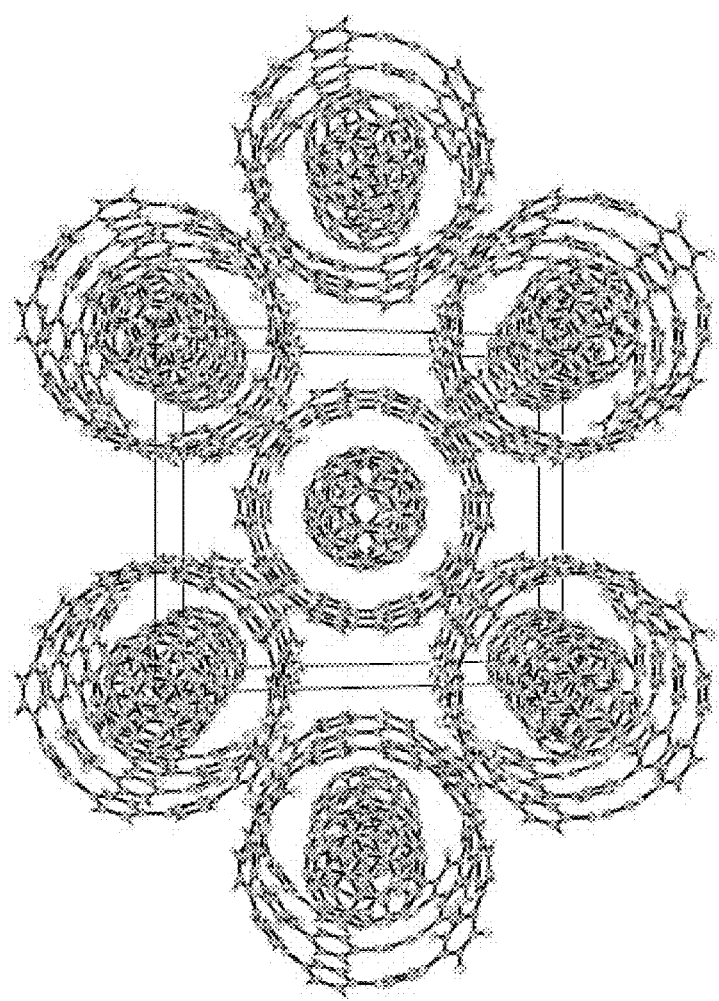
FIG. 7 is an X-ray structure of a network of assemblies that further comprise C60 molecules within the inner pores of the assemblies.

In yet additional embodiments, the disclosed assemblies and assembly networks can be used in applications using porous materials. For example, the disclosed assemblies and assembly networks can be used as chemical sensors (e.g., gas detectors capable of identifying toxic gases, greenhouse gases, and the like; gas separators capable separating individual gases from gas mixtures; gas-permeable membranes), adsorbent materials (e.g., purification systems capable of removing pollutants and contaminants, iodine adsorbers, and the like), drug delivery systems, and the like. The inherent pores of the disclosed assemblies and assembly networks provide a region (or space) wherein compounds can be trapped and/or from which compounds can be released. Solely by way of example, the ability of the disclosed assemblies and assembly networks to house compounds within the inner pores of the assemblies is illustrated in FIG. 7, which is an X-ray structure showing C60 molecules housed within inner pores of representative assemblies within an assembly network. As can be seen by FIG. 7, a plurality of the C60 molecules can be housed within an individual assembly's inner pore. In some embodiments, regions formed between different assemblies (such as in a network of assemblies) can serve as pores to absorb and/or adsorb different compounds.

The disclosed halogenated nanohoop compounds and assemblies thereof can be used as components of energy storage devices. For example, the assemblies described herein exhibit electrical conductivity that enables them to serve as organic electronic materials (e.g., films) in energy storage devices. In some embodiments, the assemblies described herein can be used to form thin films for use in energy storage devices, such as capacitors, batteries, fuel cells, solar cells, and the like. Thin films comprising the assemblies can be obtained through solution-based deposition techniques whereby the assemblies are dissolved or dispersed in a solvent (e.g., ether-based solvents, such as THF) and then deposited on a substrate (e.g., metallic or non-metallic substrates, such as silicon substrates, silicon oxide substrates, or combinations thereof and other substrates suitable for use in energy storage). Suitable deposition methods include, but are not limited to, dip-coating methods, spin-coating methods, spray-coating methods, and the like. The thin films can have thicknesses ranging from 1 nm to hundreds of micrometers, such as 1 nm to 800 μm, or 100 nm to 500 μm, or 10 μm to 200 μm. Films prepared using the disclosed assemblies can be used to achieve good capacitance values throughout a range of current densities. In particular disclosed embodiments, thin films of the disclosed assemblies can exhibit conductivity values of $3.8 \times 10^{-7}$ S cm$^{-1}$ to $7.8 \times 10^{-7}$ S cm$^{-1}$; however, the conductivity values obtained using the disclosed nanohoop compounds can have values ranging from $1 \times 10^{-5}$ S cm$^{-1}$ to $1 \times 10^{-8}$ S cm-1.

Figure 8:
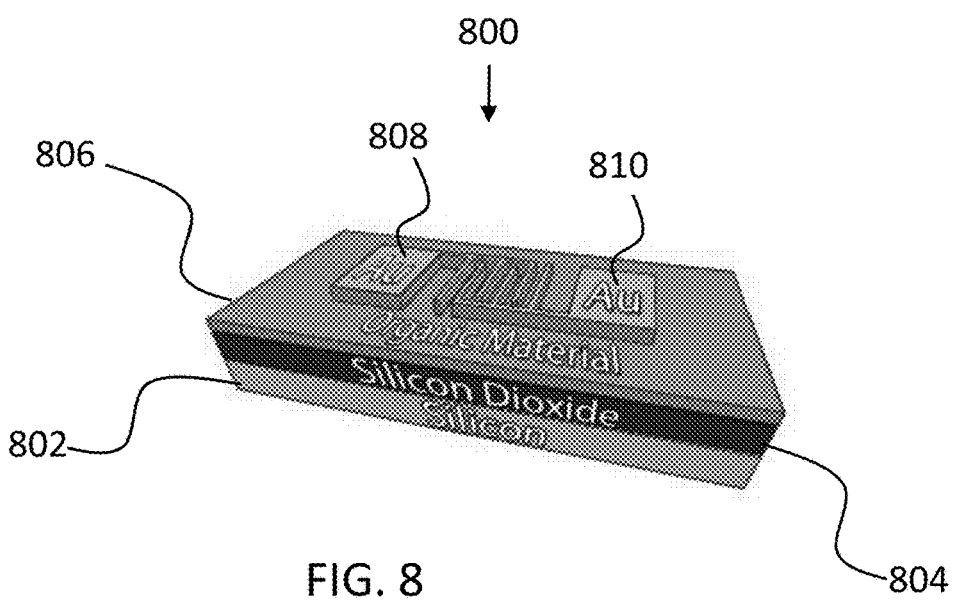
FIG. 8 illustrates a representative electronic device that can be made using disclosed halogenated nanohoops and assemblies thereof.

Devices comprising the halogenated nanohoop compounds and assemblies thereof are contemplated by the present disclosure. In some embodiments, a solar cell is disclosed wherein the disclosed assemblies are used to form a photoactive layer of the solar cell. For example, the solar cell can comprise a cathode, a metal-containing layer, a photoactive layer, a polymeric layer, and another metal-containing layer. A representative solar cell comprises an aluminum cathode associated with a layer of LiF, which is in turn associated with a layer formed from a disclosed assembly embodiment, wherein the assembly further houses a compound, such as C60. The assembly layer can be associated with a polymeric layer, such as a layer comprising PEDOT:PSS, which in turn is associated with an ITO layer. In yet additional embodiments, the assemblies can be used to form thin-film layers for electronic devices, such the two-contact device illustrated in FIG. 8. As illustrated in FIG. 8, a two-contact electronic device 800 can be made using assemblies described herein such that the two-contact electronic device 800 comprises a silicon layer 802, a silicon dioxide layer 804, a deposited assembly thin-film 806, and two contacts 808 and 810.

VII. Examples

General Information:

$^1$H NMR spectra were recorded at 500 MHz on Varian VNMR spectrometer, 500 MHz on a Bruker, or 600 MHz on Bruker. All $^1$H NMR spectra are referenced to TMS (δ 0.00 ppm), CH$_2$Cl$_2$ (δ 5.32 ppm), or (CH$_3$)$_3$CO (δ 2.05 ppm). All $^{13}$C NMR spectra are references to a residual CHCl$_3$ (δ 77.16 ppm), CH$_2$Cl$_2$ (54.00 ppm), or (CH$_3$)$_3$CO (δ 29.84 ppm). All reagents were obtained commercially. All glassware was flame-dried and cooled under an inert atmosphere of nitrogen unless otherwise noted. Moisture sensitive reactions were carried out under an inert atmosphere of nitrogen using standard syringe/septa technique. Absorbance spectra were collected in dichloromethane (DCM) in a 1 cm quartz cuvette on an Agilent Cary 60 UV-Vis spectrophotometer. Cyclic voltammetry experiments (scan rate=100 mV/s) were performed using a CH Instruments 1200B potentiostat running CH Instruments software. Measurements were conducted in degassed 0.100 M nBu$_4$PF$_6$ (recrystallized 3× from methanol) in tetrahydrofuran under an N$_2$ atmosphere with a glassy carbon working electrode, platinum counter electrode, and an Ag reference electrode. The ferrocene/ferrocenium couple was used as an internal reference. Silica column chromatography was conducted with Zeochem Zeoprep 60 Eco 40-63 μM silica gel while alumina chromatography utilized Sorbent Technologies 50-200 um Basic Activity II-II Alumina.

Example 1

To a flame-dried 100 mL flask containing THF (30 mL) was added diisopropylamine (0.774 mL, 5.49 mmol, 2.60 equiv). This flask was then cooled to 0° C. at which point nBuLi (2.5 M in hexanes, 1.94 mL, 4.85 mmol, 2.30 equiv.) was added dropwise. After stirring for 10 minutes at 0° C., the flask was then was then cooled to −78° C. over 45 minutes. To this flask was then added 1,2,4,5-tetrafluorobenzene (neat) (240 uL, 2.11 mmol, 1.00 equiv) followed by 302 (as a solution in 3 mL THF) (2.0 g, 5.27 mmol, 2.5 equiv) resulting in a bright yellow solution that slowly became brown/orange over the course of 1 h. After 1 hour of stirring, the reaction was slowly quenched with a 20% acetic acid/methanol solution (5 mL), resulting in a colorless solution which was then brought to room temperature. The organic solvents were then removed via rotary evaporation and the remaining slightly yellow aqueous layer was extracted with ethyl acetate (3×75 mL). The combined organic phases were washed with H$_2$O (3×100 mL), and brine (1×100 mL), and dried over sodium sulfate. The solvent was removed under reduced pressure to afford a faint yellow oil. Chromatography (0 to 10% EtOAc/Hexanes) of this oil yielded 305 as a colorless oil (1.41 g, 74%). $^1$H NMR (500 MHz, Chloroform-d) δ 7.41 (d, J=8.7 Hz, 4H), 7.21 (d, J=8.5 Hz, 4H), 6.30 (d, J=10.2 Hz, 4H), 6.01 (d, J=10.1 Hz, 4H), 2.55 (s, 2H), 0.99 (t, J=7.9 Hz, 18H), 0.69 (q, J=7.9 Hz, 12H). $^{13}$C NMR (126 MHz, CDCl$_3$) δ 143.96, 134.16, 131.48, 127.64, 127.41, 121.43, 71.06, 68.02, 7.18, 6.58. $^{19}$F NMR (471 MHz, Chloroform-d) δ −138.00 (s). δ HRMS (TOF, ES+) (m/z): [M+2Na]+ calculated for C$_{42}$H$_{47}$O$_4$Na$_2$Br$_2$F$_4$Si$_2$, 951.1111; found, 951.1354.

Example 2

Figure 9:
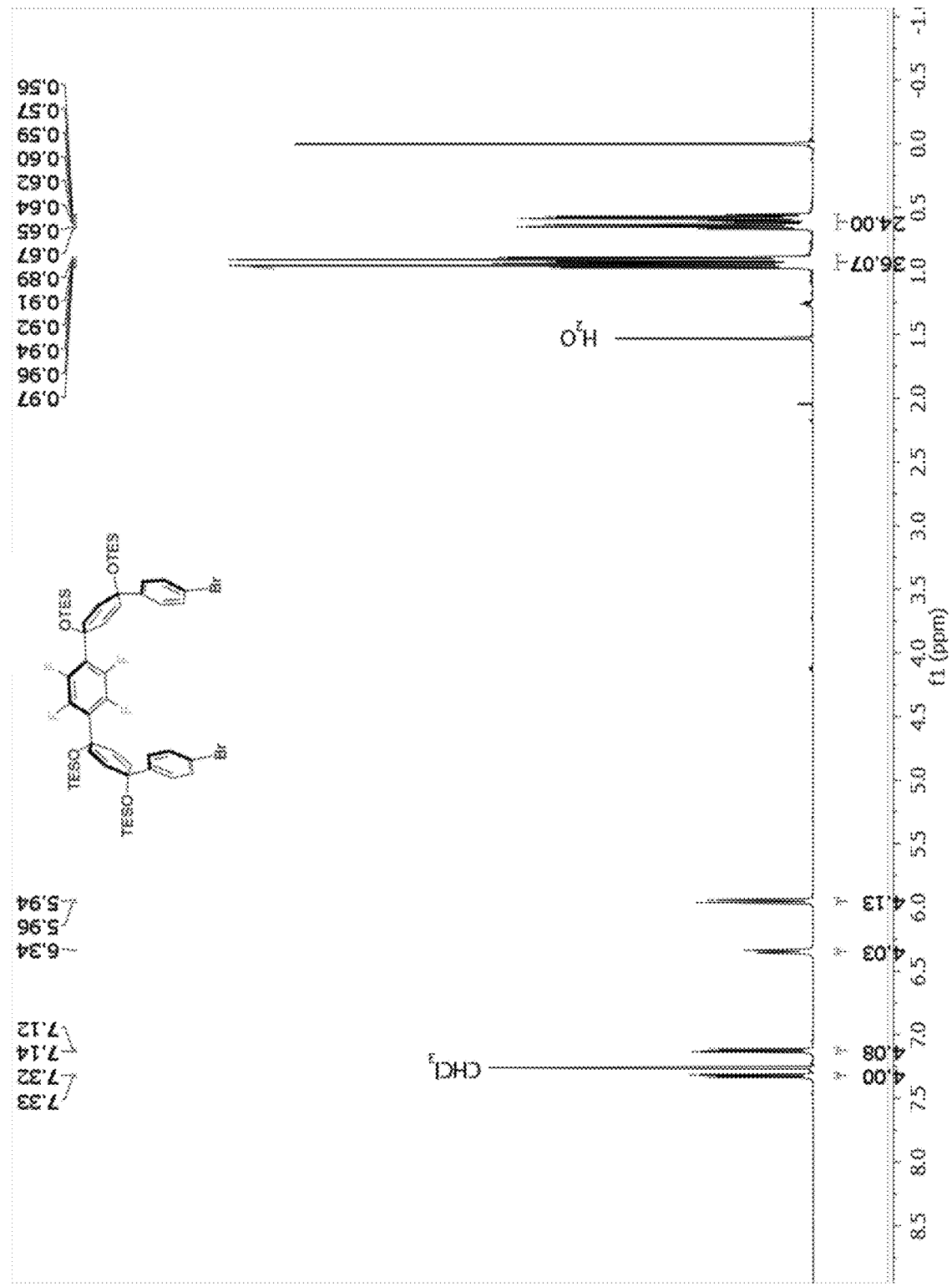
FIG. 9 is a $^1$H-NMR spectrum of a representative halogenated nanohoop intermediate compound.
Figure 10:
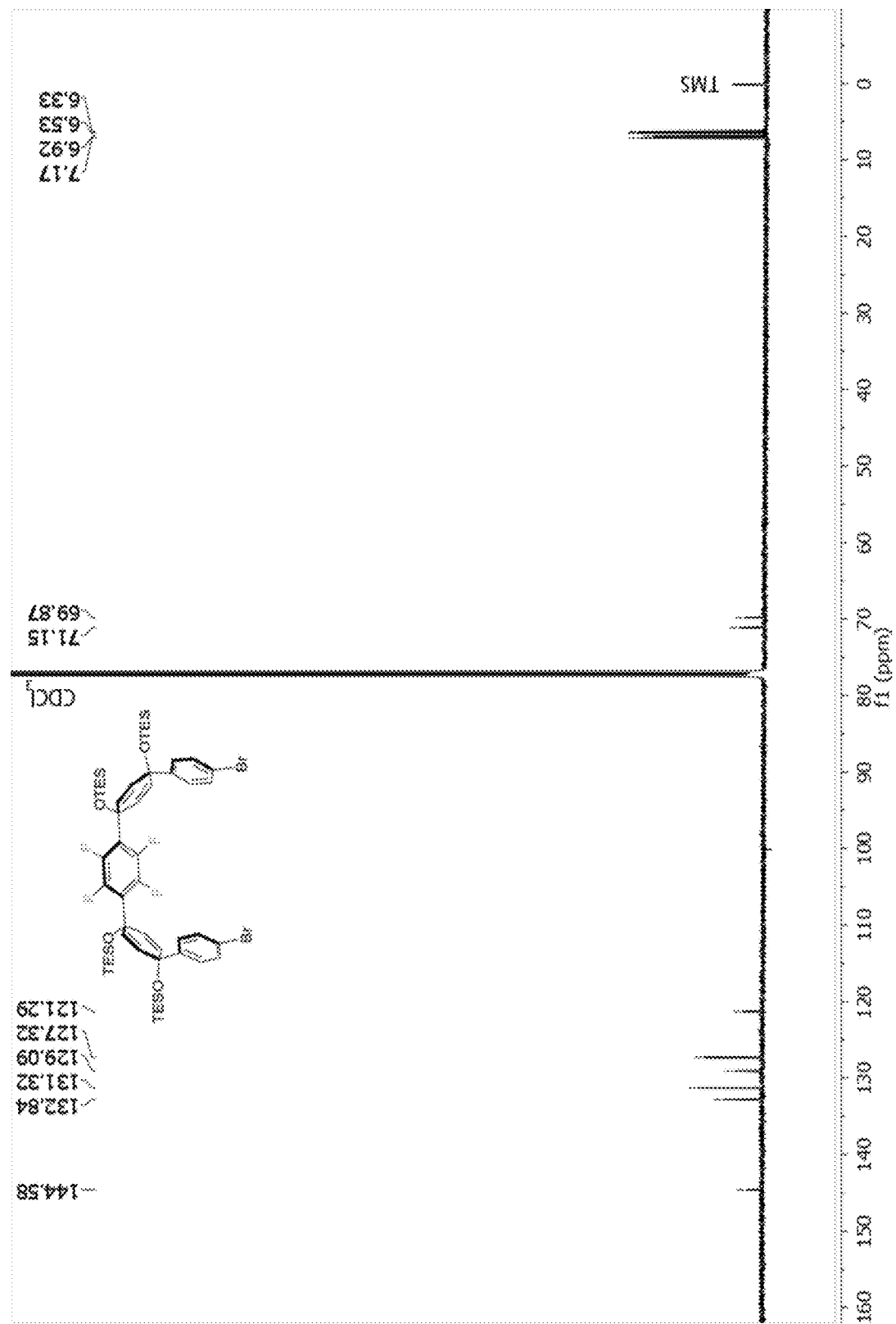
FIG. 10 is a $^{13}$C-NMR spectrum of a representative halogenated nanohoop intermediate compound.

Imidazole (0.420 g, 6.16 mmol, 4.0 equiv), and 305 (1.40 g, 1.54 mmol, 1.00 equiv.) were added to a 100 mL flame-dried RBF, then dissolved in 25 mL DMF. The resulting solution was heated to 40° C. at which point chlorotriethylsilane (TESCl) (0.700 g, 4.63 mmol, 3.00 equiv.) was added dropwise. The reaction was monitored via $^1$H NMR until all the starting material was consumed (typically 4 hours). Once complete, the reaction was neutralized with sodium bicarbonate followed by extraction of the resulting white suspension with EtOAc (3×75 mL). The combined organic phases were washed with 5% LiCl (5×100 mL), followed by H$_2$O (1×100 mL), brine (1×100 mL), and then placed over sodium sulfate. Removal of solvent via rotary evaporation yielded a yellow oil which was then triturated with MeOH followed by filtration and collection of the resulting white solid to give 306 (1.52 g, 89%). $^1$H NMR (500 MHz, Chloroform-d) δ 7.32 (d, J=8.7 Hz, 4H), 7.13 (d, J=8.7 Hz, 4H), 6.35 (d, J=9.7 Hz, 4H), 5.95 (d, J=10.2 Hz, 4H), 0.99-0.86 (m, 36H), 0.70-0.53 (m, 24H). $^{13}$C NMR (126 MHz, CDCl$_3$) δ 144.58, 132.84, 131.32, 129.09, 127.32, 121.29, 71.15, 69.87, 7.17, 6.92, 6.53, 6.33. $^{19}$F NMR (471 MHz, CDCl$_3$) δ −136.88 (s). δ LRMS (TOF, MALDI) (m/z): [M]+ calculated for C$_{54}$H$_{76}$O$_4$Br$_2$F$_4$Si$_4$, 1134.315; found, 1136.425. See FIGS. 9 and 10 for $^1$H NMR and $^{13}$C NMR spectra, respectively.

Example 3

Figure 11:
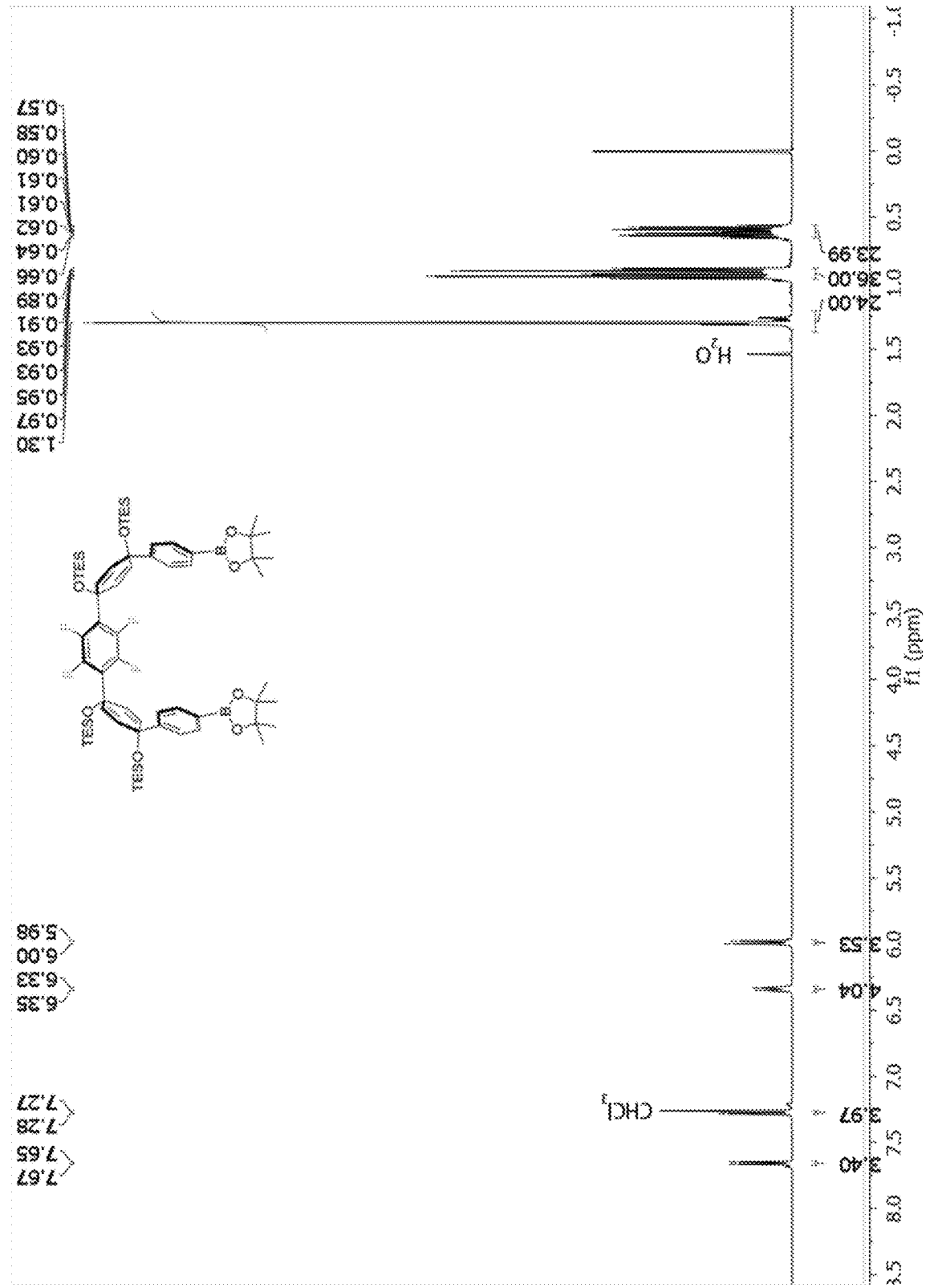
FIG. 11 is a $^1$H-NMR spectrum of a representative halogenated nanohoop intermediate compound.
Figure 12:
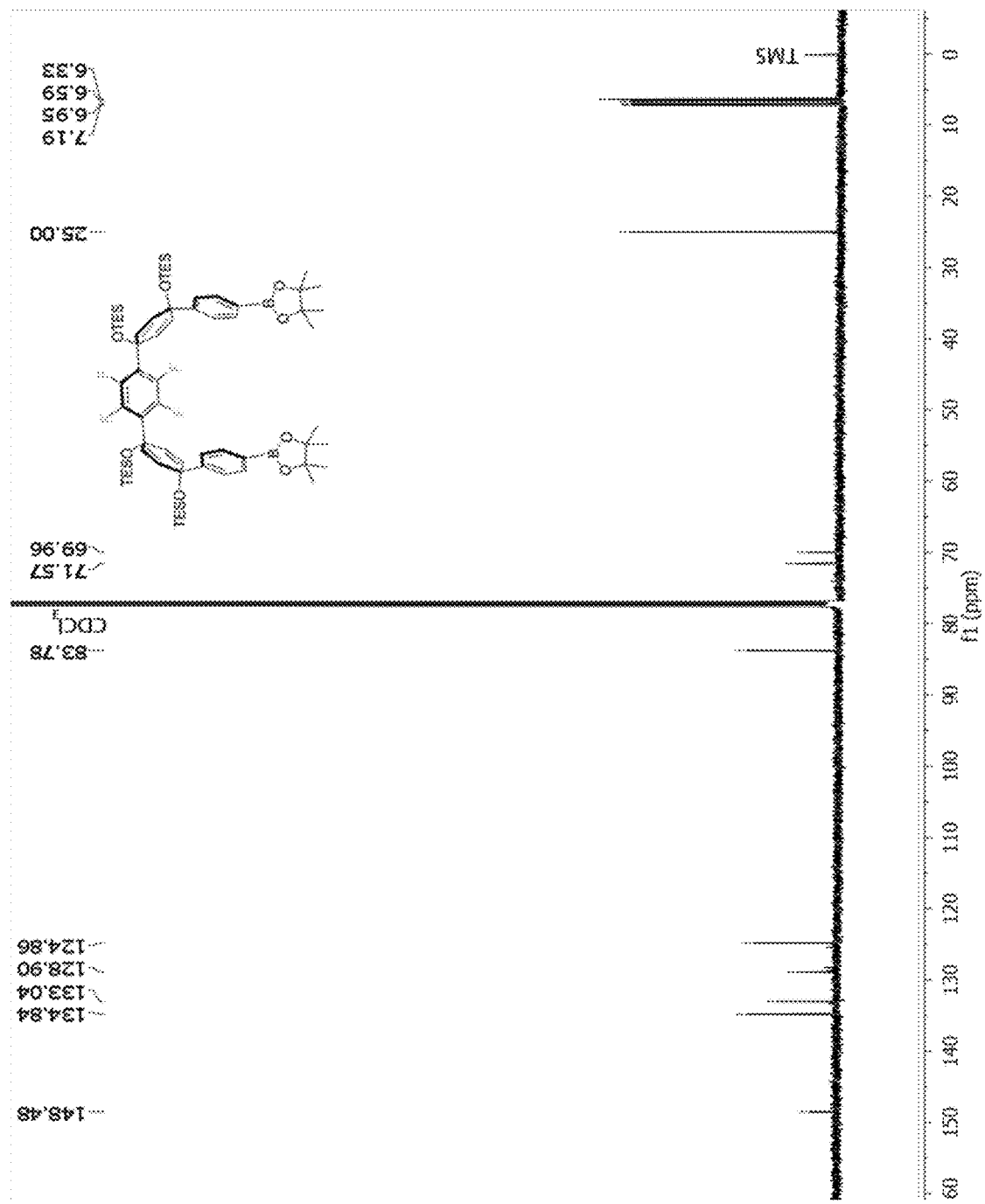
FIG. 12 is a $^{13}$C-NMR spectrum of a representative halogenated nanohoop intermediate compound.

To a 100 mL flame-dried flask was added Pd(OAc)$_2$ (11.0 mg, 0.0484 mmol, 0.100 equiv), 2-dicyclohexylphosphino-2', 6'dimethoxybiphenyl (50.0 mg, 0.121 mmol, 0.250 equiv), bis(pinacolato)diboron (0.492 g, 1.94 mmol, 4.00 equiv.), 306 (0.550 g, 0.484 mmol, 1.00 equiv.), and K$_3$PO$_4$ (0.520 g, 2.45 mmol, 5.00 equiv.). After the solids were added, the flask was evacuated and backfilled with nitrogen 5 times. 1,4-dioxane (30 mL) was then added to the flask resulting in an orange solution, which was then placed into an 80° C. oil bath. After 3 h, the resulting black solution was brought to room temperature and the solvent was removed under reduced pressure. To this black solid was added $H_2O$ (50 mL), followed by extracted with hexanes (3×75 mL). The combined organic phases were then washed with water (3×50 mL), brine (1×100 mL), and then dried over sodium sulfate. After removing the organic solvent via rotary evaporation, the resulting white solid was then washed with plenty of methanol, which after filtration, gave 308 as a white solid (2.99 g, 92%). $^1$H NMR (500 MHz, Chloroform-d) δ 7.66 (d, J=8.4 Hz, 4H), 7.27 (d, J=8.2 Hz, 4H), 6.34 (d, J=10.1 Hz, 4H), 5.99 (d, J=10.2 Hz, 4H), 1.30 (s, 24H), 0.98-0.88 (m, 36H), 0.68-0.56 (m, 24H). $^{13}$C NMR (126 MHz, $CDCl_3$) δ 148.48, 134.84, 133.04, 128.90, 124.86, 83.78, 71.57, 69.96, 25.00, 7.19, 6.95, 6.59, 6.33. $^{19}$F NMR (471 MHz, $CDCl_3$) δ −137.01 (s). δ HRMS (TOF, ES+) (m/z): [M+Na]+ calculated $C_{66}H_{100}O_8NaF_4Si_4B_2$, 1253.6515; found, 1253.6544. See FIGS. 11 and 12 for $^1$H NMR and $^{13}$C NMR spectra, respectively.

Example 4

Figure 13:
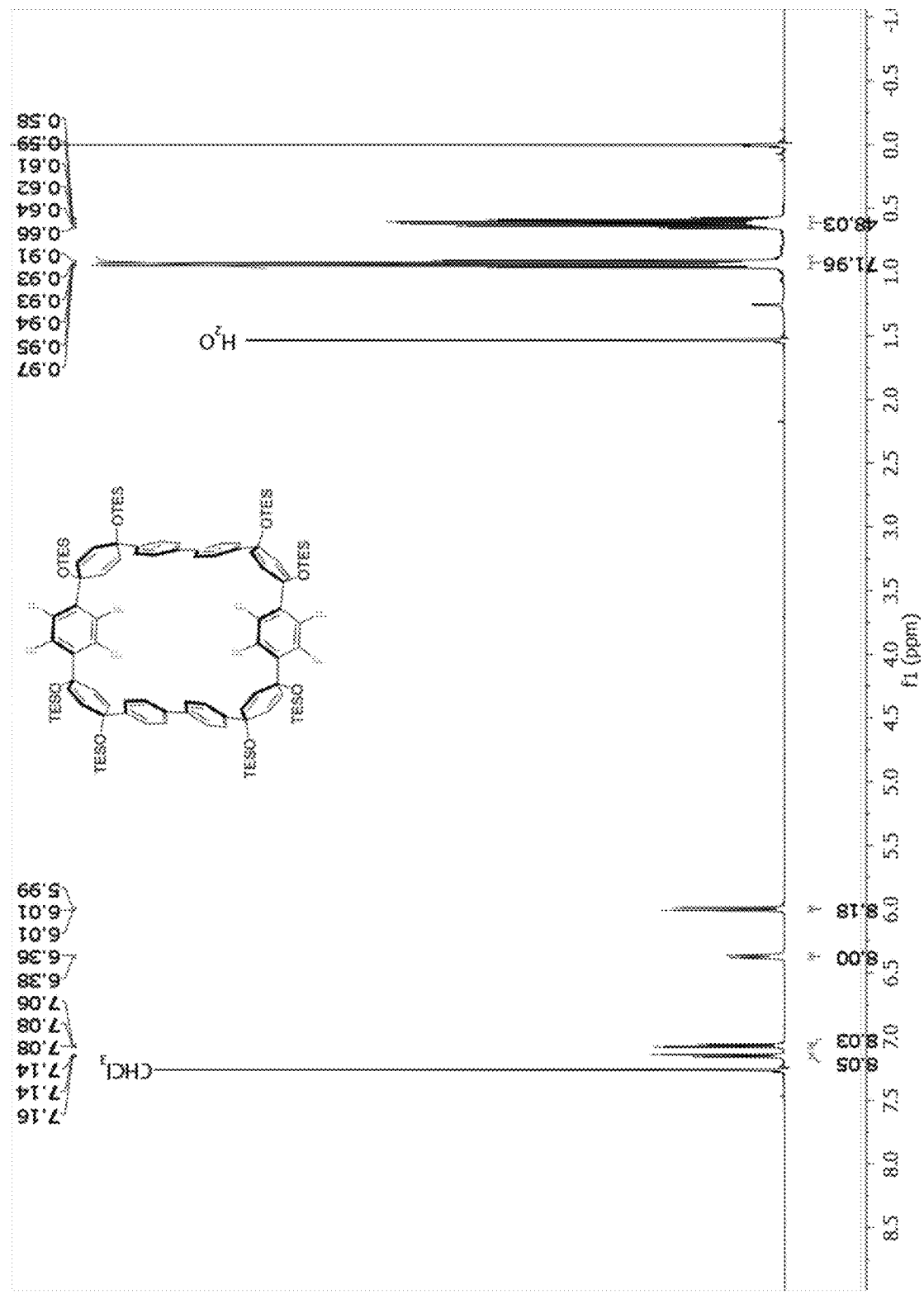
FIG. 13 is a $^1$H-NMR spectrum of a representative halogenated nanohoop precursor compound.
Figure 14:
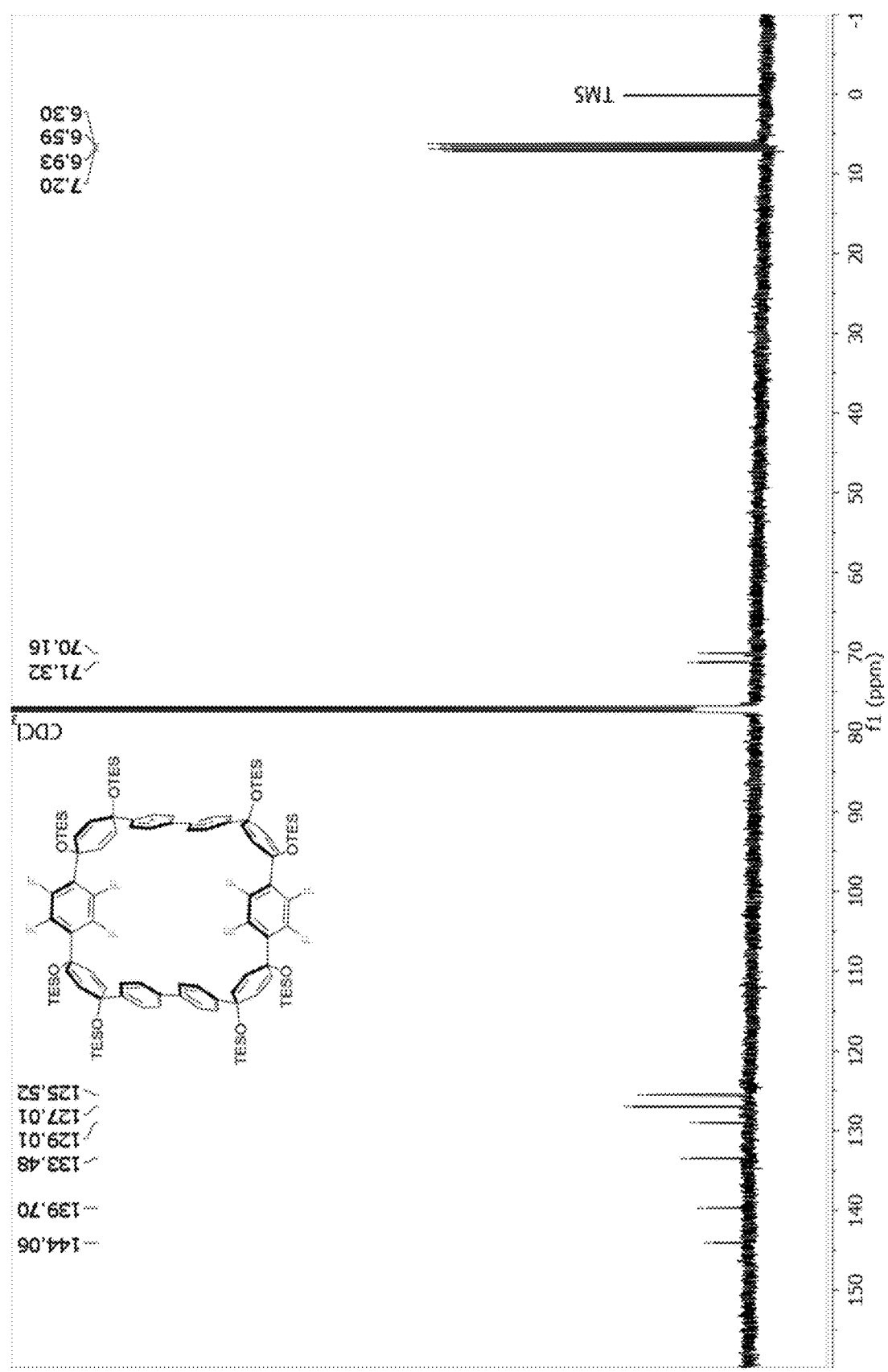
FIG. 14 is a $^{13}$C-NMR spectrum of a representative halogenated nanohoop precursor compound.

To a flame-dried 250 mL round bottom flask equipped with a stir bar was added 306 (0.268 g, 2.36 mmol, 1.00 equiv), 308 (0.290 g, 2.36 mmol, 1.00 equiv.), and Pd SPhos GII (16.9 mg, 0.0236 mmol, 0.100 equiv). The flask was evacuated and back-filled with $N_2$ 5 times, followed by addition of 1,4-dioxane (118 mL). This solution was then vigorously spared with $N_2$ for 2 hours at which point the solution was placed into an oil bath at 80° C. At this point, an aqueous solution of 2M $K_3PO_4$ (11.8 mL, 23.6 mmol, 10.0 equiv) was added, quickly turning the colorless solution bright yellow. This solution was allowed to stir for 1 hour, at which point the solution was cooled to room temperature followed by removal of the solvent via rotary evaporation. The resulting yellow/brown oil was extracted with hexanes (3×100 mL), followed by washing of the combined organic phases with $H_2O$ (3×100 mL), brine (1×100 mL), and finally placed over sodium sulfate. After solvent removal, the brown oil was dissolved in hexanes and then filtered over a fritted funnel. The brown solids were washed with plenty of hexanes and the resulting yellow filtrate was concentrated to a yellow oil. The addition of acetone caused the precipitation of a white solid, which after collection via filtration and washing with acetone yielded 210 as a white solid (0.207 g, 45%). $^1$H NMR (500 MHz, Chloroform-d) δ 7.15 (d, J=8.4 Hz, 8H), 7.07 (d, J=8.5 Hz, 8H), 6.37 (d, J=10.2 Hz, 8H), 6.00 (d, J=10.4 Hz, 8H), 1.01-0.81 (m, 72H), 0.76-0.53 (m, 48H). $^{13}$C NMR (126 MHz, $CDCl_3$) δ 144.06, 139.70, 133.48, 129.01, 127.01, 125.52, 71.32, 70.16, 7.20, 6.93, 6.59, 6.30. 19F NMR (471 MHz, $CDCl_3$) δ −136.43 (s). δ LRMS (TOF, MALDI) (m/z): [M]+ calculated for $C_{108}H_{152}O_8F_8Si_8$, 1952.951; found, 1954.126. See FIGS. 13 and 14 for $^1$H NMR and $^{13}$C NMR spectra, respectively.

Example 5

To a flame-dried 100 mL round bottom flask equipped with a stir bar was added 310 (0.180 g, 0.0922 mmol, 1.00 equiv.) followed by THF (20 mL). To this solution was then added glacial acetic acid (0.265 mL, 4.61 mmol, 50.0 equiv.), followed by tetrabutylammonium fluoride (1M in THF, 1.84 mL, 1.84 mmol, 20.0 equiv). The resulting colorless solution was then stirred for 18 hours at which point $H_2O$ (10 mL) was added, followed by removal of THF via rotary evaporation. The white solid was then filtered and washed with $H_2O$ (30 mL) and DCM (3×10 mL) to give 211 (0.0901 g, 94%). $^1$H NMR (500 MHz, DMSO-d6) δ 7.47 (d, J=8.5 Hz, 8H), 7.35 (d, J=8.4 Hz, 8H), 6.20 (d, J=9.9 Hz, 8H), 5.97-5.91 (m, 12H), 5.61 (s, 8H). 19F NMR (471 MHz, DMSO) δ −138.55 (s). Due to insolubility, $^{13}$C NMR data was not be obtained. δ HRMS (TOF, ES+) (m/z): [M+Na]+ calculated for $C_{60}H_{40}F_8O_8Na$, 1063.2493; found 1063.2474.

Example 6

Figure 15:
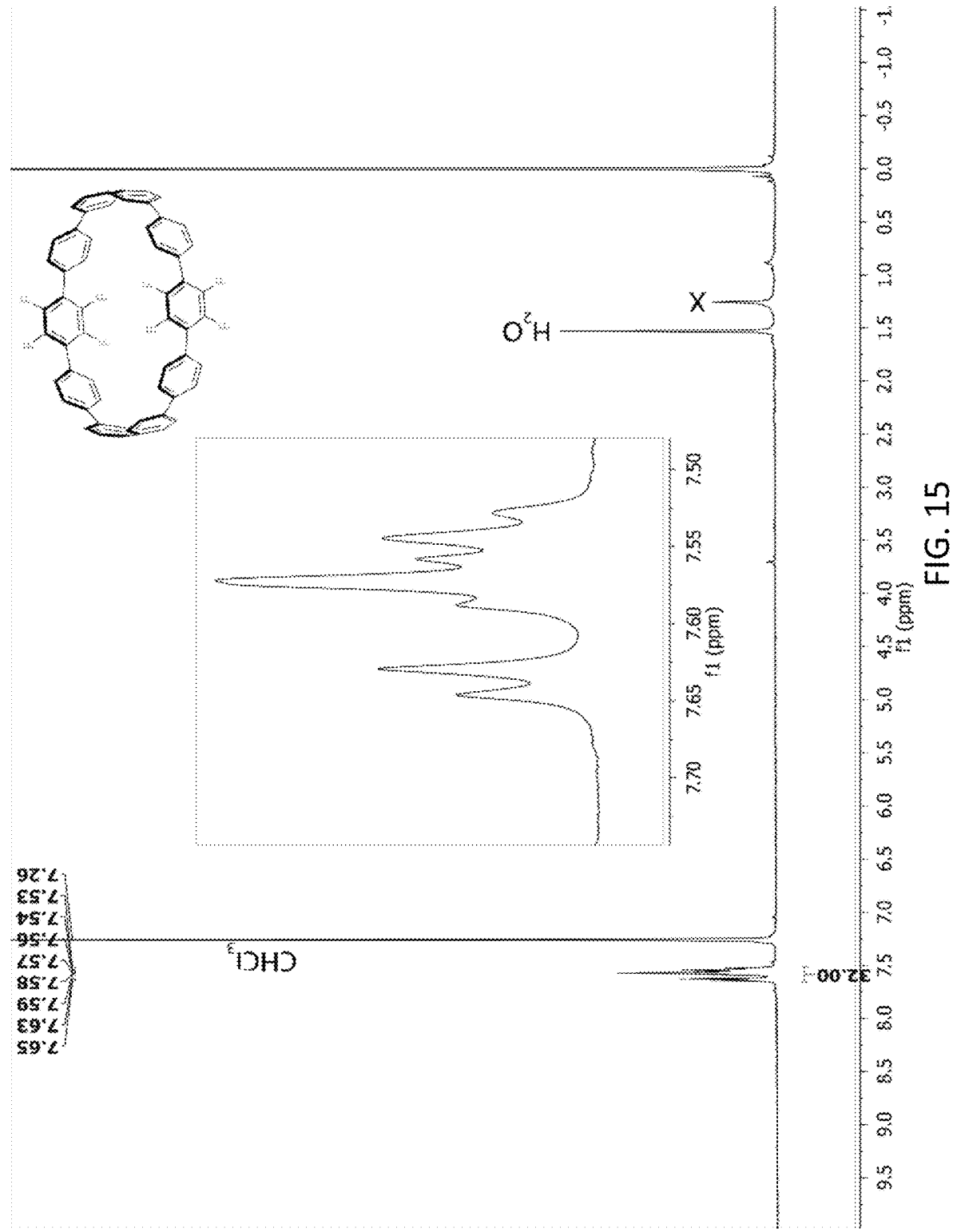
FIG. 15 is a $^1$H-NMR spectrum of a representative halogenated nanohoop compound.
Figure 16:
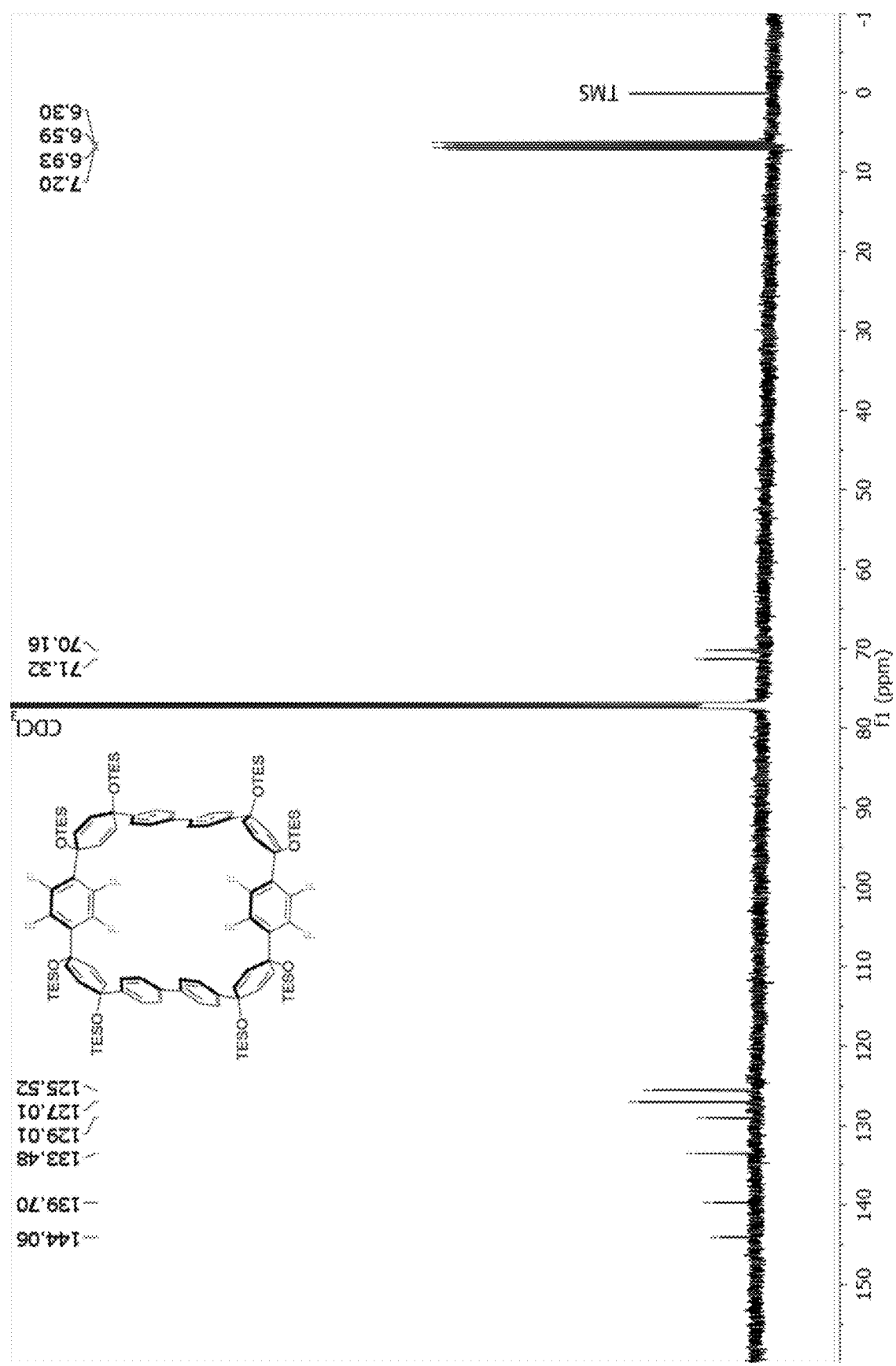
FIG. 16 is a $^{13}$C-NMR spectrum of a representative halogenated nanohoop compound.
Figure 17:
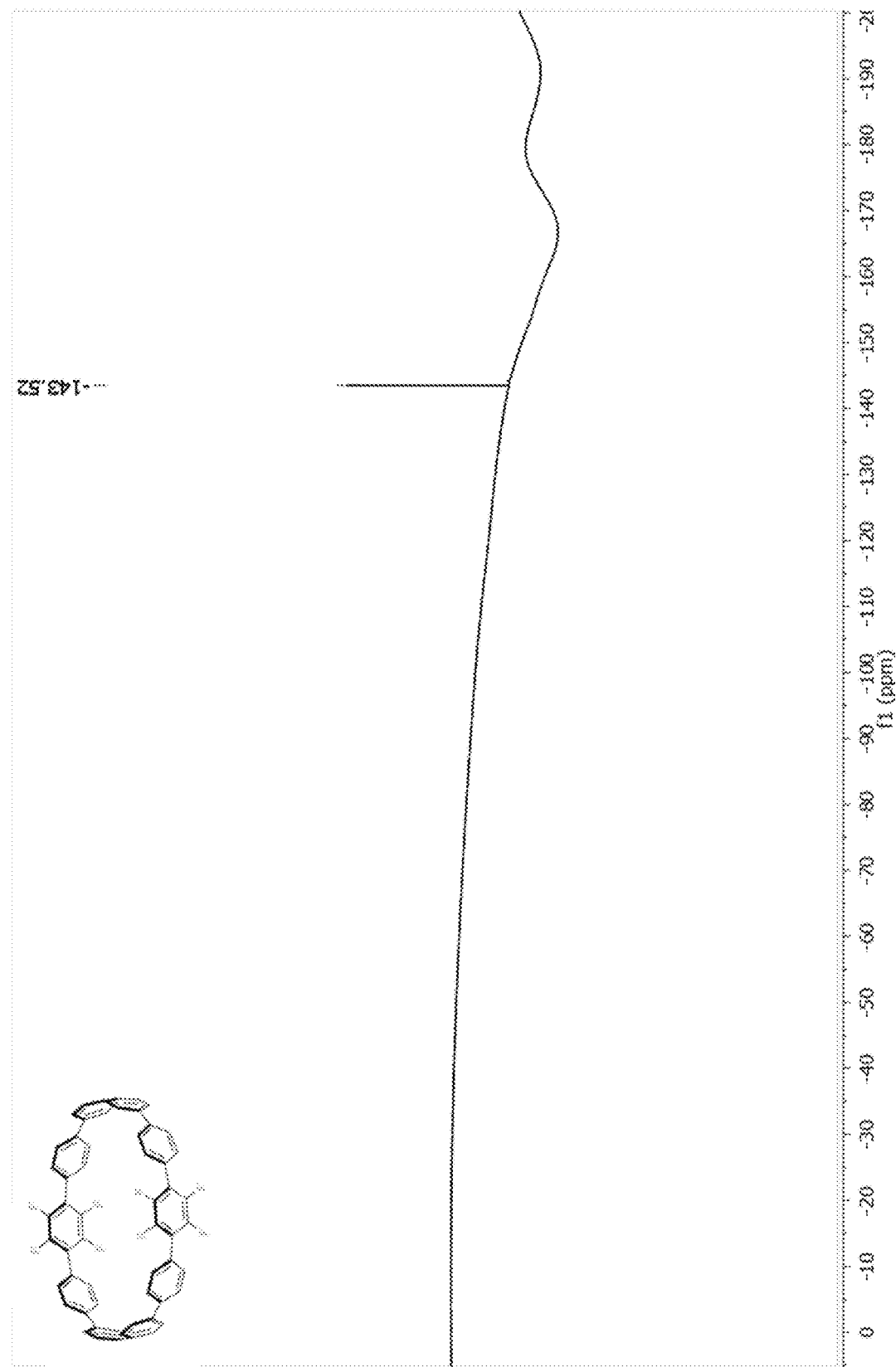
FIG. 17 is a $^{19}$F-NMR spectrum of a representative halogenated nanohoop compound.

To a flame-dried 100 mL round bottom flask equipped with a stir bar was added 311 (0.0901 g, 0.0866 mmol, 1.00 equiv.), followed by THF (40 mL). To this suspension was added $H_2SnCl_4$ (0.40 M in THF, 0.683 mmol, 1.73 mL, 8 equiv), resulting in a yellow suspension. This was then allowed to stir for 3 hours, at which point aqueous (18 w/w %) ammonia (10 mL) was added followed by removal of THF via rotary evaporation. The resulting aqueous suspension was then extracted with DCM (3×100 mL). The combined organic phases were washed with $H_2O$ (3×50 mL), brine (1×50 mL) and then dried over sodium sulfate. After removal of DCM under reduced pressure, the resulting yellow solid was run through a short alumina column using DCM eluent, providing 212 as a white solid (12.5 mg, 16%). $^1$H NMR (500 MHz, Chloroform-d) δ 7.71-7.45 (m, 32H). $^{19}$F NMR (471 MHz, $CDCl_3$) δ −143.52 (s). Due to insolubility, $^{13}$C NMR data was not be obtained. δ HRMS (TOF, ES+) (m/z): [M]$^+$ calculated for $C_{60}H_{32}F_8$, 904.2376; found, 904.2380. See FIGS. 15-17 for $^1$H NMR, $^{13}$C NMR, and $^{19}$F NMR spectra, respectively.

Example 7

To a 100 mL flame-dried flask was added 302 (0.296 g, 0.240 mmol, 1 equiv), 1-bromo-4-chlorobenzene (0.276 g, 1.44 mmol, 6 equiv), and [1, 1'bis(diphenylphosphino)ferrocenedichloropalladium (0.018 g, 0.024 mmol, 0.100 equiv). After the solids were added, the flask was evacuated and backfilled with nitrogen 5 times. 1,4-dioxane (10.0 mL) was then added to the flask and the solution was sparged for 10 min. before aqueous 2M $K_3PO_4$ (0.660 mL, 1.32 mmol, 5.5 equiv), sparged for 1 h prior to use, was added. The solution was then placed in an 80° C. oil bath and allowed to stir for 12 h. The next day, the reddish-black solution was allowed to come to room temperature before removing the solvent under reduced pressure. Next, $H_2O$ (50 mL) was added, followed by extraction with hexanes (3×50 mL). The combined organic phases were then washed with water (3×50 mL), brine (1×75 mL), and dried over sodium sulfate. After removal of solvent via rotary evaporation, the resulting yellow oil was purified via column chromatography to provide 500 (2-5% EtOAc/Hexanes) to afford a clean, colorless oil that was pure via NMR. If desired, the oil can be washed with methanol to access the compound as a white solid (0.276 g, 96%).

Example 8

To a 100 mL flame-dried flask was added $Pd(OAc)_2$ (0.003 g, 0.029 mmol, 0.05 equiv), 2-dicyclohexylphosphino-2'6'dimethoxybiphenyl (0.015 g, 0.036 mmol, 0.125 equiv), bis(pinacolato)diboron (0.584 g, 2.30 mmol, 8 equiv), 500 (0.353 g, 0.290 mmol, 1 equiv), and $K_3PO_4$ (0.228 g, 2.30 mmol, 8 equiv). After the solids were added, the flask was evacuated and backfilled with nitrogen 5 times. 1,4-dioxane (8.0 mL) was then added to the flask and the solution was sparged for 10 min. before being placed in an 80° C. oil bath overnight. The next day, the black solution was brought to room temperature and the solvent was removed under reduced pressure. To the resulting black solid was added H$_2$O (50 mL), followed by extraction with DCM (3×50 mL). The combined organic phases were then washed with water (3×50 mL), brine (1×100 mL), and then dried over sodium sulfate. After removing the solvent via rotary evaporation, the resulting brown solid was washed with methanol, which after filtration afforded 306 as a white solid (0.374 g, 93%). $^1$H NMR (500 MHz, Chloroform-d) δ 7.82 (d, J=7.4 Hz, 4H), 7.52 (d, J=7.4 Hz, 4H), 7.45 (d, J=7.6 Hz, 4H), 7.33 (d, J=7.9 Hz, 4H), 6.36 (d, J=9.8 Hz, 4H), 6.01 (d, 8H), 1.35 (s, 24H), 0.98 (t, J=7.9 Hz, 18H), 0.90 (t, J=7.6 Hz, 18H), 0.67 (q, J=7.9 Hz, 12H), 0.59 (q, J=7.9 Hz, 12H). $^{13}$C NMR (126 MHz, Chloroform-d) δ 144.66, 143.42, 139.71, 135.16, 133.07, 128.70, 126.93, 126.29, 125.79, 83.77, 71.25, 69.85, 24.88, 7.07, 6.80, 6.44, 6.19. $^{19}$F NMR (471 MHz, Chloroform-d) δ −136.83 (s).

Example 9

To a 100 mL flame-dried flask was added 308 (0.224 g, 0.300 mmol, 1 equiv) and [1, 1'bis(diphenylphosphino)ferrocenedichloropalladium (0.022, 0.030 mmol, 0.100 equiv). After the solids were added, the flask was evacuated and backfilled with nitrogen 5 times. 1,4-dioxane (8.0 mL) was then added to the flask, followed by 1-bromo-2,3,5,6-tetrafluorobenzene (0.412 g, 1.80 mmol, 6 equiv), and the solution was sparged for 10 min. before 2M K$_3$PO$_4$ (0.825 mL, 1.65 mmol, 5.5 equiv), sparged for 1 h prior to use, was added. The solution was then placed in an 80° C. oil bath and allowed to stir overnight. The next day, the black solution was allowed to come to room temperature before removing the solvent under reduced pressure. Next, H$_2$O (50 mL) was added, followed by extraction with hexanes (3×50 mL). The combined organic phases were then washed with water (3×50 mL), brine (1×75 mL), and dried over sodium sulfate. After removing the solvent via rotary evaporation, the crude, yellow-orange oil was purified via column chromatography (2-5% EtOAc/Hexanes) and 310 isolated as a pale yellow oil (0.175 g, 74%). $^1$H NMR (500 MHz, Chloroform-d) δ 7.47 (d, J=7.7 Hz, 2H), 7.37 (d, J=7.9 Hz, 2H), 7.04 (p, J=8.4 Hz, 2H), 6.07 (s, 4H), 0.96 (t, J=7.9 Hz, 18H), 0.64 (q, J=7.8 Hz, 12H). $^{13}$C NMR (126 MHz, Chloroform-d) δ 146.95, 131.58, 129.94, 126.12, 71.38, 7.03, 6.46. $^{19}$F NMR (471 MHz, Chloroform-d) δ −139.24 (m, J=22.4, 11.3 Hz), −143.81 (m, J=21.1, 12.7, 7.4 Hz).

Example 10

To a 250 mL flame-dried flask was added 20 mL THF and diisopropylamine (0.093 mL, 0.666 mmol, 3 equiv). This solution was placed in a 0° C. ice bath and allowed to stir for 20 min. before n-butyllithium (2.2 M in hexanes, 0.252 mL, 0.555 mmol, 2.5 equiv) was added dropwise. The solution was allowed to stir for 15 min. before being transferred to a −78° C. dry ice bath, after which the solution was allowed to cool for 45 minutes. Next, 310 (0.175 g, 0.222 mmol, 1 equiv), dissolved in minimal THF (approx. 2 mL), was added dropwise and the solution was allowed to stir for 10 min. before 12 (0.279 g, 1.11 mmol, 5 equiv.), dissolved in minimal THF (approx. 2 mL), was added quickly, turning the solution dark orange-brown. The solution was allowed to stir for 2 h before being quenched with concentrated Na$_2$S$_3$O$_3$ (approx. 100 mL), resulting in an off white solution. The solution was brought under reduced pressure to remove THF and 50 mL of water was added, followed by a workup in EtOAc (3×50 mL). The combined organic phases were washed with water (3×50 mL), brine (1×50 mL), and dried over sodium sulfate. After removing the solvent via rotary evaporation, the crude yellow-brown oil was purified via column chromatography (10-25% DCM/Hexanes), resulting in a waxy clear oil. Washing with methanol then afforded the product 312 as a white powdery solid, which was collected via vacuum filtration (0.190 g, 82%). $^1$H NMR (500 MHz, Chloroform-d) δ 7.47 (d, J=8.2 Hz, 2H), 7.36 (d, J=8.0 Hz, 2H), 6.07 (s, 4H), 0.95 (t, J=7.9 Hz, 18H), 0.64 (q, J=7.9 Hz, 12H). $^{13}$C NMR (126 MHz, Chloroform-d) δ 147.16, 131.57, 129.87, 126.18, 71.38, 7.03, 6.46. $^{19}$F NMR (471 MHz, Chloroform-d) δ −120.77 (m), −141.47 (m).

Example 11

To a flame-dried 250 mL round bottom flask equipped with a stir bar was added 304 (0.334 g, 0.271 mmol, 1.00 equiv.), 500 (0.325 g, 0.271 mmol, 1.00 equiv.), and SPhos-Pd-G2 (0.039 g, 0.0542 mmol, 0.200 equiv.). The flask was evacuated and back-filled with N$_2$ 5 times, followed by addition of 1,4-dioxane (90 mL). This solution was then vigorously spared with N$_2$ for 1 h at which point the solution was placed into an oil bath at 80° C. At this point, an aqueous solution of 2M K$_3$PO$_4$ (9.03 mL, 4.52 mmol, 17.0 equiv) was added. The solution was allowed to stir for 12 hours, after which the solution was brought to room temperature and the solvent was removed under reduced pressure. Water (50 mL) was added, followed by extraction with DCM (3×50 mL). The combined organic phases were washed with water (3×50 mL), brine (1×50 mL), and dried over sodium sulfate. The solvent was removed via rotary evaporation, and the resulting brown solid was purified via column chromatography (0-40% DCM/Hexanes) using basic alumina as the stationary phase. This afforded 502 as a white solid (0.199 g, 35%). $^1$H NMR (500 MHz, Chloroform-d) δ 7.36 (d, J=7.9 Hz, 8H), 7.28 (d, J=7.7 Hz, 8H), 6.40 (d, J=9.7 Hz, 8H), 5.99 (d, J=9.3 Hz, 8H), 0.99 (t, J=7.8 Hz, 36H), 0.94 (t, J=8.0 Hz, 36H), 0.69 (q, J=7.9 Hz, 24H), 0.61 (q, J=7.8 Hz, 24H). $^{13}$C NMR (126 MHz, Chloroform-d) δ 144.12, 139.60, 139.06, 133.18, 128.59, 127.09, 126.62, 125.66, 71.37, 69.95, 7.08, 6.80, 6.43, 6.20. $^{19}$F NMR (471 MHz, Chloroform-d) δ −136.37 (s).

Example 12

To a flame-dried 50 mL round bottom flask equipped with a stir bar was added 502 (0.374 g, 0.180 mmol, 1.00 equiv.) followed by THF (10 mL). To this solution was then added glacial acetic acid (0.520 mL, 9.00 mmol, 50.0 equiv.), followed by tetrabutylammonium fluoride (1M in THF, 4.50 mL, 4.50 mmol, 25.0 equiv.) dropwise. The resulting colorless solution was then stirred for 18 h at which point H$_2$O (10 mL) was added, followed by removal of THF via rotary evaporation. The resulting suspension was vacuum filtered, washed with water and minimal DCM, and allowed to fully dry. The resulting white solid was then added to an oven-dried 100 mL round bottom flask equipped with a stir bar, followed by THF (8 mL), resulting in a white suspension. Next, H$_2$SnCl$_4$ (0.04 M, 36.0 mL, 8 equiv) was added dropwise, after which the solution was allowed to stir for 12 h. Next, the THF was removed via rotary evaporation and water (50 mL) was added followed by extraction in DCM (3×50 mL). The combined organic phases were then washed with water (3×50 mL), brine (1×50 mL), and dried over sodium sulfate. The solvent was removed via rotary evaporation and the resulting white solid was purified via column chromatography (0-40% DCM/Hexanes) using basic alumina as the stationary phase. After the removal of solvent, 504 was isolated as a white solid (0.012 g, 12%). $^1$H NMR (500 MHz, Chloroform-d) δ 7.70-7.63 (m, 30H), 7.57 (d, J=8.4 Hz, 10H). $^{19}$F NMR (471 MHz, Chloroform-d) δ −143.86 (s). Due to insolubility, $^{13}$C NMR data could not be obtained.

Example 13

To a flame-dried 250 mL round bottom flask equipped with a stir bar was added 306 (0.183 g, 0.132 mmol, 1.00 equiv.), 312 (0.137 g, 0.132 mmol, 1.00 equiv.), and SPhos-Pd-G2 (0.019 g, 0.0264 mmol, 0.200 equiv.). The flask was evacuated and back-filled with $N_2$ 5 times, followed by addition of 1,4-dioxane (44 mL). This solution was then vigorously spared with $N_2$ for 1 h at which point the solution was placed into an oil bath at 80° C. At this point, an aqueous solution of 2M $K_3PO_4$ (4.4 mL, 2.20 mmol, 17.0 equiv) was added. The solution was allowed to stir for 12 hours, after which the solution was brought to room temperature and the solvent was removed under reduced pressure. Water (50 mL) was added, followed by extraction with hexanes (3×50 mL). The combined organic phases were washed with water (3×50 mL), brine (1×50 mL), and dried over sodium sulfate. The solvent was removed via rotary evaporation, and the resulting reddish solid was purified via gel permeation chromatography to afford 400 as a white crystalline solid. Alternatively, the crude material can be washed with acetone and minimal isopropyl alcohol at a slight loss of purity (0.164 g, 65%). $^1$H NMR (500 MHz, Chloroform-d) δ 7.64 (d, J=7.7 Hz, 4H), 7.57-7.45 (m, 16H), 7.38 (d, J=7.8 Hz, 4H), 6.41 (d, J=9.5 Hz, 4H), 6.11 (s, 4H), 6.06 (d, J=9.6 Hz, 4H), 1.05-0.88 (m, 54H), 0.66 (dt, J=28.5, 7.6 Hz, 36H). $^{13}$C NMR (151 MHz, Chloroform-d) δ 146.95, 144.90, 141.52, 139.01, 133.05, 131.58, 130.49, 130.04, 128.80, 128.63, 127.14, 126.91, 126.14, 125.93, 71.26, 69.86, 7.06, 6.81, 6.47, 6.43, 6.20. $^{19}$F NMR (471 MHz, Chloroform-d) δ −136.86 (s), −144.33 (m).

Example 14

To a flame-dried 50 mL round bottom flask equipped with a stir bar was added 400 (0.174 g, 0.091 mmol, 1.00 equiv.) followed by THF (10 mL). To this solution was then added glacial acetic acid (0.261 mL, 4.54 mmol, 50.0 equiv.), followed by tetrabutylammonium fluoride (1M in THF, 2.27 mL, 2.27 mmol, 25.0 equiv.) dropwise. This solution was then stirred for 18 h at which point $H_2O$ (10 mL) was added, followed by removal of THF via rotary evaporation. The resulting suspension was vacuum filtered, washed with water and minimal DCM, and allowed to fully dry. The resulting crude white solid was then added to an oven-dried 100 mL round bottom flask equipped with a stir bar, followed by THF (8 mL), resulting in a white suspension. Next, $H_2SnCl_4$ (0.04 M, 18.15 mL, 8 equiv) was added dropwise, after which the solution was allowed to stir for 3 h. Next, the THF was removed via rotary evaporation and water (50 mL) was added followed by extraction in DCM (3×50 mL). The combined organic phases were then washed with water (3×50 mL), brine (1×50 mL), and dried over sodium sulfate. The solvent was removed via rotary evaporation and the resulting white solid was purified via column chromatography (0-40% DCM/Hexanes) using basic alumina as the stationary phase. After the removal of solvent, 402 was isolated as a light beige solid (0.004 g, 4%). $^1$H NMR (500 MHz, Chloroform-d) δ 7.69 (d, J=6.2 Hz, 24H), 7.59 (d, J=8.2 Hz, 12H). $^{19}$F NMR (471 MHz, Chloroform-d) δ −143.82 (s). Due to insolubility, $^{13}$C NMR data could not be obtained.

Example 15

To determine how halogenated nanohoop compounds, such as fluorinated nanohoops, differ from the all-hydrocarbon-CPPs in the solid-state, X-ray crystallography was used. Slow evaporation of a solution of 212 in THF readily provided large, transparent single crystals suitable for X-ray crystallography. Shown in FIGS. 1 and 2 is the solid-state packing of fluorinated nanohoop 212 (FIG. 1) and the solid-state packing of [10]CPP (FIG. 2) for comparison. The packing of nanohoop 212 is significantly different than that of [10]CPP, where [10]CPP adopts a herringbone-type motif—a common observation in the all-hydrocarbon nanohoops—and nanohoop 212 packs into nanotube-like columnar sheets. Also noteworthy is the observation that the crystal of fluorinated nanohoop 212 appears to contain a large amount of void space, with each nanohoop hosting only a single THF molecule. Additionally, it was found that vapor diffusion of pentane into a concentrated solution 212 in THF provided single crystals with packing nearly identical to that shown in FIG. 1, with the primary difference being pentane hosted by the nanohoop rather than THF. Further analysis of the solid-state data of 212 revealed the likely origin of this tubular structure where two different non-covalent interactions were found—perfluoroarene-arene (FIG. 5) and aryl C—F to aryl C—H (FIG. 4) interactions. Each nanohoop engages in a total of four perfluoroarene-arene interactions with the distance between each aryl ring being 3.78 Å, which aligns well with previously reported distances (3.4-3.8 Å) for perfluoroarene-arene interactions. Additionally, multiple short contacts between the aryl C—F and aryl C—H atoms of neighboring nanohoops were observed to be between 2.53 and 2.85 Å, which likely directs the formation into nanotube-like columns. Interestingly, similar packing has been observed in [6]CPP, however the reasoning behind this arrangement is less clear as there are no observable able π-π type interactions suggesting that in the case of [6]CPP solvent may play a large role. Taken together, these data provide a rationale for the observed solid-state packing differences between fluorinated nanohoop 212 and [10]CPP, where the perfluoroarene-arene interactions likely enable the nanohoops to arrange in a face-to-face arrangement and the aryl C—F/C—H interactions direct the nanohoops into the observed columnar tubes.

Figure 30A:
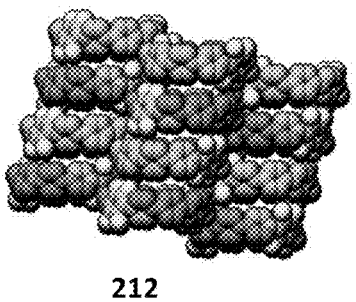
FIGS. 30A-30C are images showing columnar packing (right images of FIGS. 30A, 30B, and 30C), arene-perfluoroarene interactions (middle images of FIGS. 30A, 30B, and 30C) and C—H—F interactions (right images of FIGS. 30A, 30B, and 30C) observed in the crystal structures of three representative halogenated nanohoop embodiments.
Figure 30A:
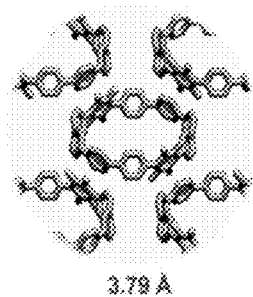
Figure 30A:
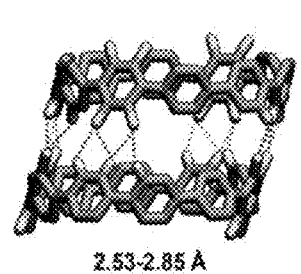
Figure 30B:
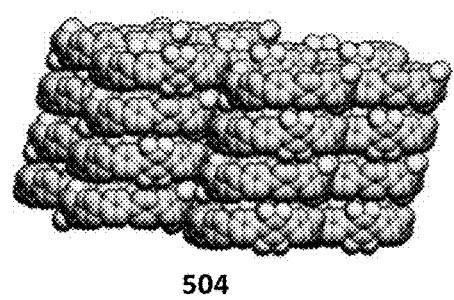
Figure 30B:
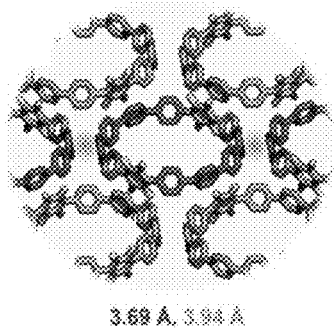
Figure 30B:
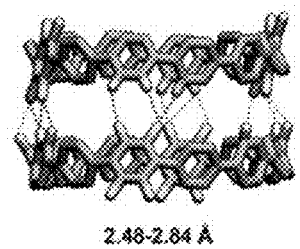
Figure 30C:
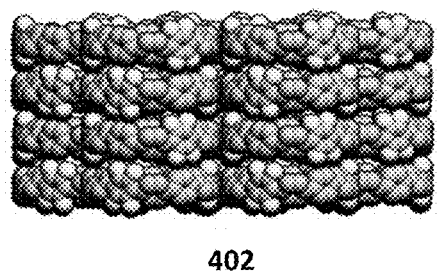
Figure 30C:
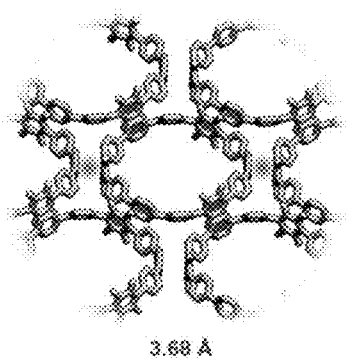
Figure 30C:
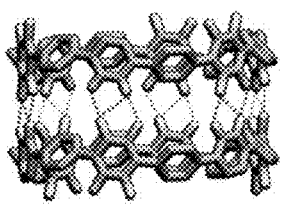

Additional x-ray crystal structure analysis results are shown by FIGS. 30A-30C. As shown by FIG. 30A, packing of nanohoop 212 (FIG. 30A, left image) is significantly different than that of [10]CPP (FIG. 2), where [10]CPP adopts a herringbone-type motif and 212 packs into nanotube-like columns. Further analysis of the solid-state data of 212 revealed two different short intermolecular contacts: perfluoroarene-arene interactions (FIG. 30A, middle image) and aryl C—F to aryl C—H interactions (FIG. 30A, right image). Each nanohoop engages in a total of four perfluoroarene-arene type interactions with the distance between each aryl ring being 3.78 Å.

In another embodiment, pseudo slow evaporation of 504 in dichloromethane (DCM), achieved via the reverse vapor diffusion of the DCM solvent into pentane, afforded needle-like crystals similar in appearance to those formed by 212. To our delight, single-crystal XRD analysis revealed that 504 also self-assembles into tubular arrays (FIG. 30B, left image), again in stark contrast to the herringbone-like packing of the all-hydrocarbon analog of [12]CPP. Upon closer inspection of the crystal structure of 504, it was found that organofluorene interactions are indeed at play, with aryl-perfluoroaryl distances measuring at 3.69 Å (FIG. 30B, middle image) and aryl C—H to aryl C—F interactions ranging between 2.48 and 2.84 Å (FIG. 30B, right image). The lateral molecular ordering of 504 was unique from that of 212 in that the hoops arranged in a hexagonal, rather than square, packing motif, resulting in what appear to be two additional arene-arene interactions with distances of 3.94 Å (CITE). Without being limited to a particular theory, it currently is believed that this hexagonal packing was a result of the symmetry of the [12]CPP backbone which allows for six total aryl-to-aryl interactions, the maximum amount possible with the generic [n]CPP scaffold.

In another embodiment, the x-ray crystal structure of synthesized nanohoop 402 was evaluated to determine if six arene-areneperfluoro arene interactions would be observed per hoop in addition to a greater number of aryl C—H to C—F interactions as a result of extended fluorination, thus affording an arrangement of nanohoops into cylindrical columns in the solid state. Slow evaporation from chloroform afforded X-ray quality crystals of 402, which, like those of 212 and 504, took the form of colorless needles, a good qualitative indicator that columnar ordering had been achieved. Single-crystal XRD analysis determined that each molecular unit of 402 appears to take part in a total of six arene-perfluoroarene interactions (FIG. 30C, left image) along with a multitude of aryl C—H to F interactions (FIG. 30C, middle image), the combination of which drives the nanohoop towards this columnar arrangement. Nanohoop 402 does indeed self-assemble into an optimal columnar arrangement, exhibiting both perfectly linear nanotube-like channels along the c-axis and complete symmetry of the "horizontal" a and b lattice parameters (FIG. 30C, right image), resulting in hexagonally-packed 2-D sheets of nanohoops akin to those observed in extended MOF and COF networks but rarely seen in fully non-covalent crystalline systems.

Example 16

Figure 18:
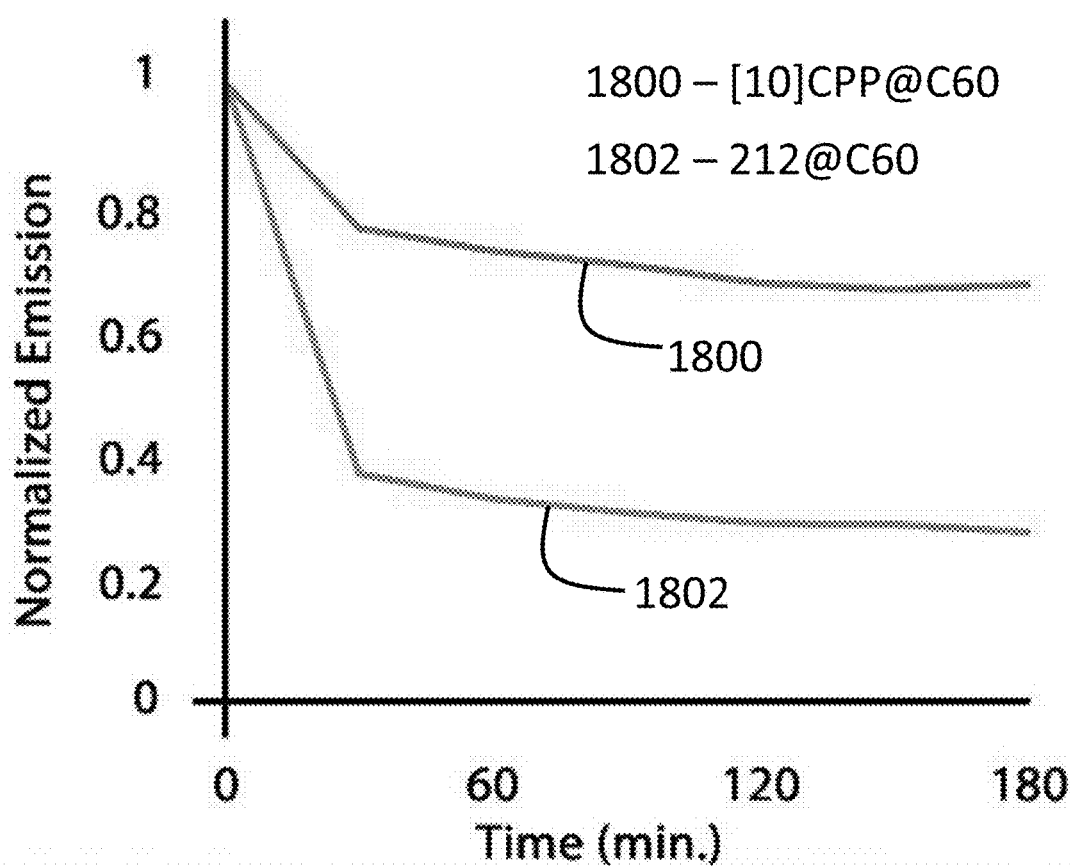
FIG. 18 is a graph of normalized emission as a function of time (minutes) illustrating the decrease in fluorescence over three hours for a thin-film comprising a representative halogenated nanohoop compound comprising C60 (1802) in comparison to that exhibited by a non-halogenated compound comprising C60 (1800).
Figure 19:
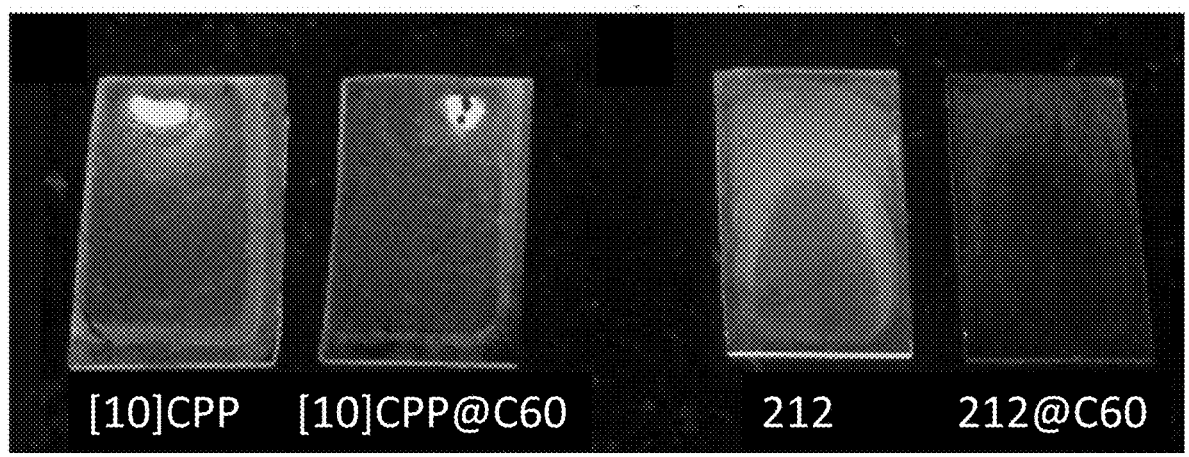
FIG. 19 includes photographic images of UV-light irradiated thin-films of a non-halogenated compound before and after ("[10]CPP" and "[10]CPP@C60," respectively) immersion in a C60-saturated hexane solution as well as an irradiated thin-film of a representative halogenated nanohoop compound before and after ("212" and "212@C60," respectively) immersion in a C60-saturated hexane solution.
Figure 20:
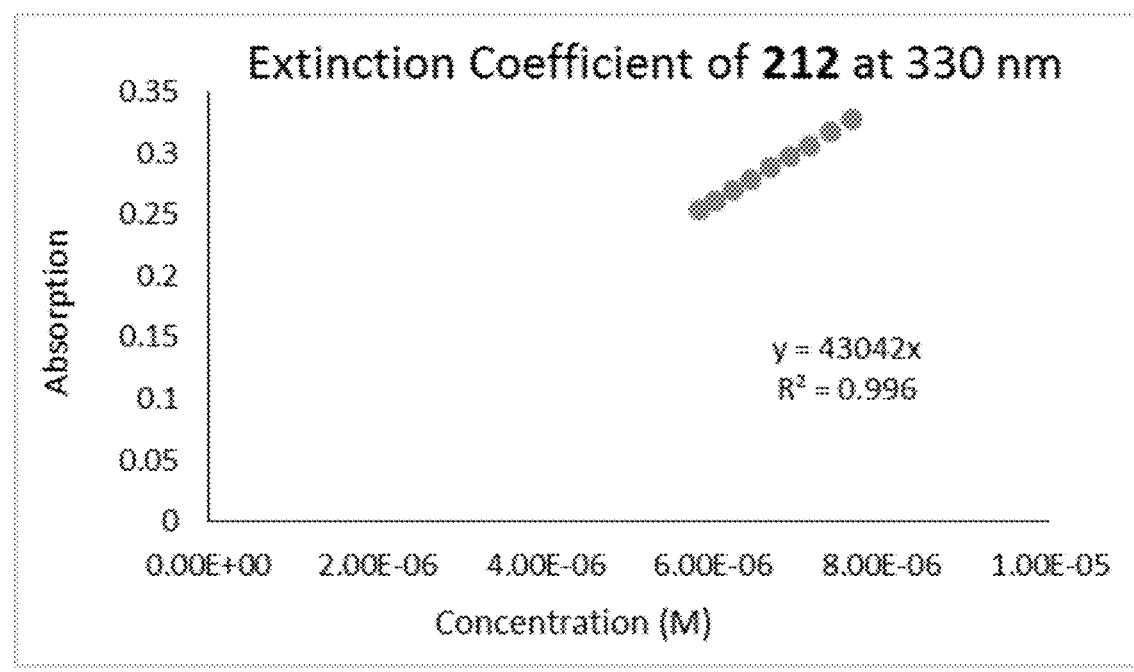
FIG. 20 is a plot of absorption as a function of concentration (M), which shows the extinction coefficient of a representative halogenated nanohoop compound at 330 nm.
Figure 21A:
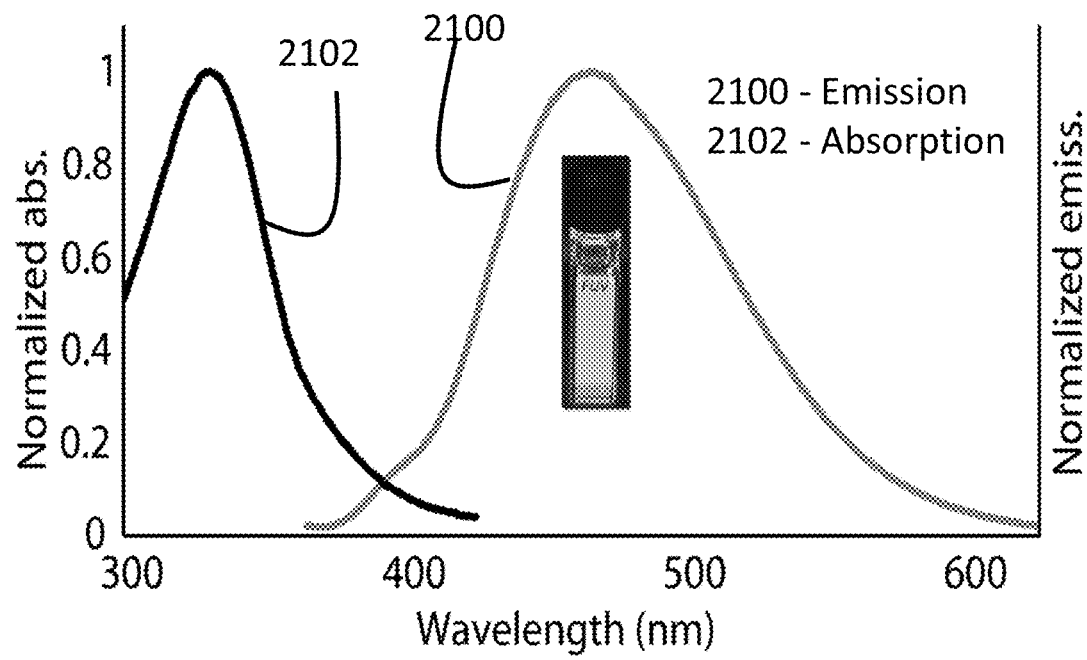
FIGS. 21A-21C are plots of normalized absorbance and normalized emission showing results obtained from analysis of representative halogenated nanohoop compounds.
Figure 21B:
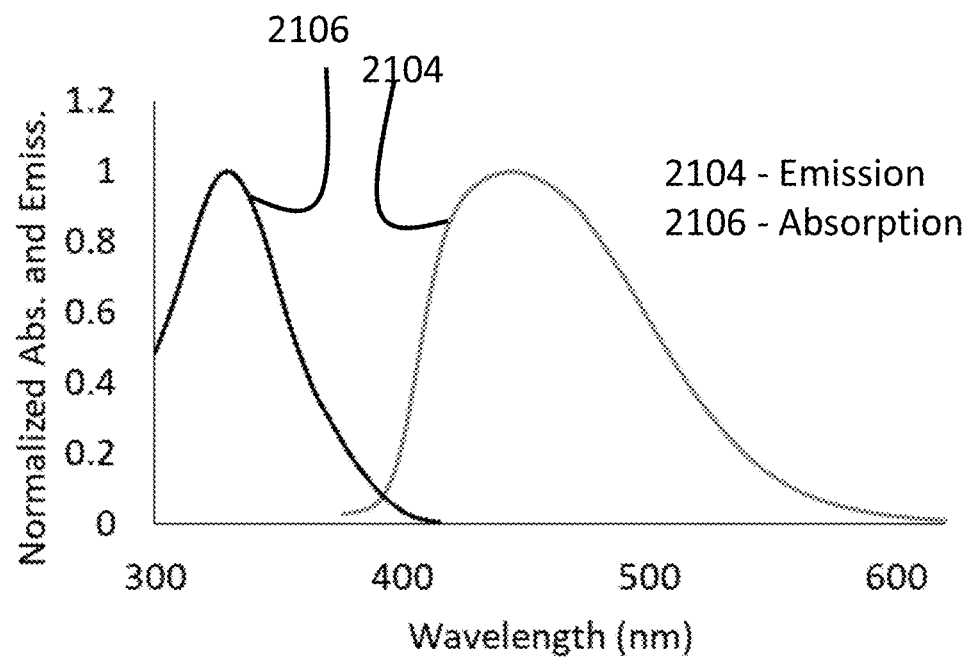
Figure 21C:
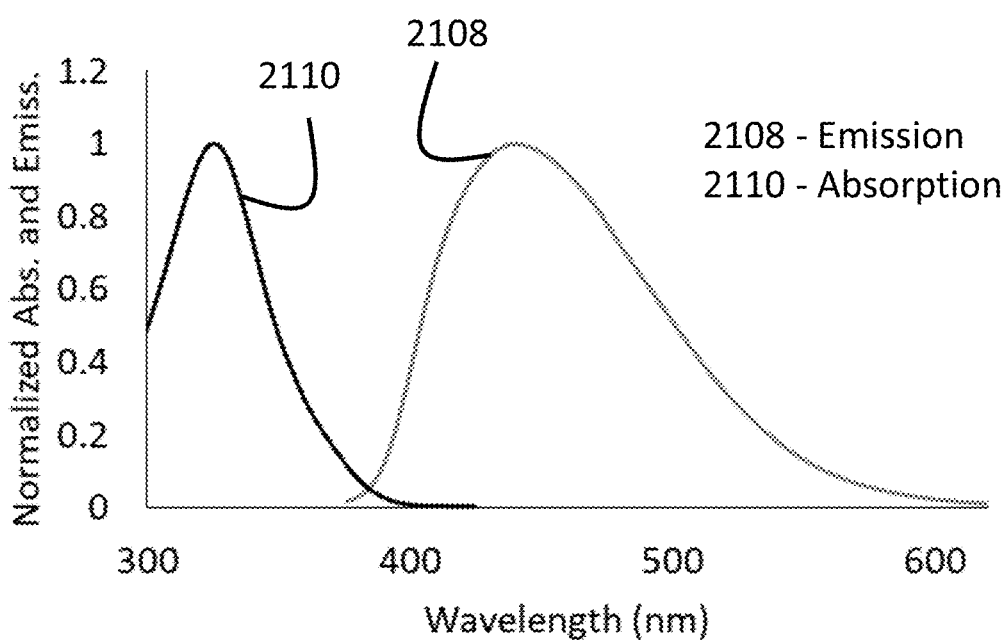

The feasibility of using 212 as new solid-state porous material for guest adsorption is examined in this example. As a first approach, the host-guest chemistry between [10] CPP and C60 was used to provide a proof of concept, where C60 would be used as a guest for the fluorinated nanohoop host. Shown in FIG. 18 is the observed decrease in fluorescence of thin-films of either 212 or [10]CPP in a C60-saturated hexanes solution over the course of 3 hours. Within the first 30 minutes of submersion, the fluorescence of the fluorinated nanohoop thin-films was reduced by nearly 40% relative to the [10]CPP films. Noteworthy is that this difference was observable to the naked eye by using a simple handheld UV-light (FIG. 19). This result corresponds to results typically observed in solution, where complexation of [10]CPP with C60 strongly quenches the fluorescence. These results thus indicate a clear difference in thin-film morphology, illustrating that that films of the fluorinated CPP 212 are capable of solid state host-guest chemistry, whereas the films of [10]CPP, likely due to different film morphology, are far less efficient at guest uptake in the solid state. To assess the thin-film morphology, thin-film X-ray diffraction was used. It was observed that thin-films of 212 and [10]CPP showed differing peak locations in their respective diffraction patterns, suggesting that the fluorinated nanohoop 212 does exhibit molecular ordering unique from that of the all-hydrocarbon-[10]CPP. This difference also was observed using standard optical microscopy, where even at the microscopic scale (e.g., 100× magnification), thin-films of 212 display unique features from [10]CPP. Taken together, these data suggest that when 212 is applied to a surface, the molecular orientation differs from that of [10]CPP and likely organizes similar to that of the channel-like packing observed in the single-crystals of 212. The extinction coefficient of compound 212 also was determined (see FIG. 20). Emission and absorbance spectra of compound 212, 504, and 402 are illustrated in FIG. 21A, FIG. 21B, and FIG. 21C, respectively.

From the above-mentioned fluorescne quenching data, a binding constant ($K_a$) of $(8.1\pm0.2)\times10^5$ $L^{-1}$ mol between fluorinated nanohoop 212 and $C_{60}$ was determined. This $K_a$ is reduced relative to the all hydrocarbon [10]CPP@$C_{60}$ complex (($2.71\pm0.03)\times10^6$ $L^{-1}$ mol) by nearly 30%.

Example 17

Figure 22:
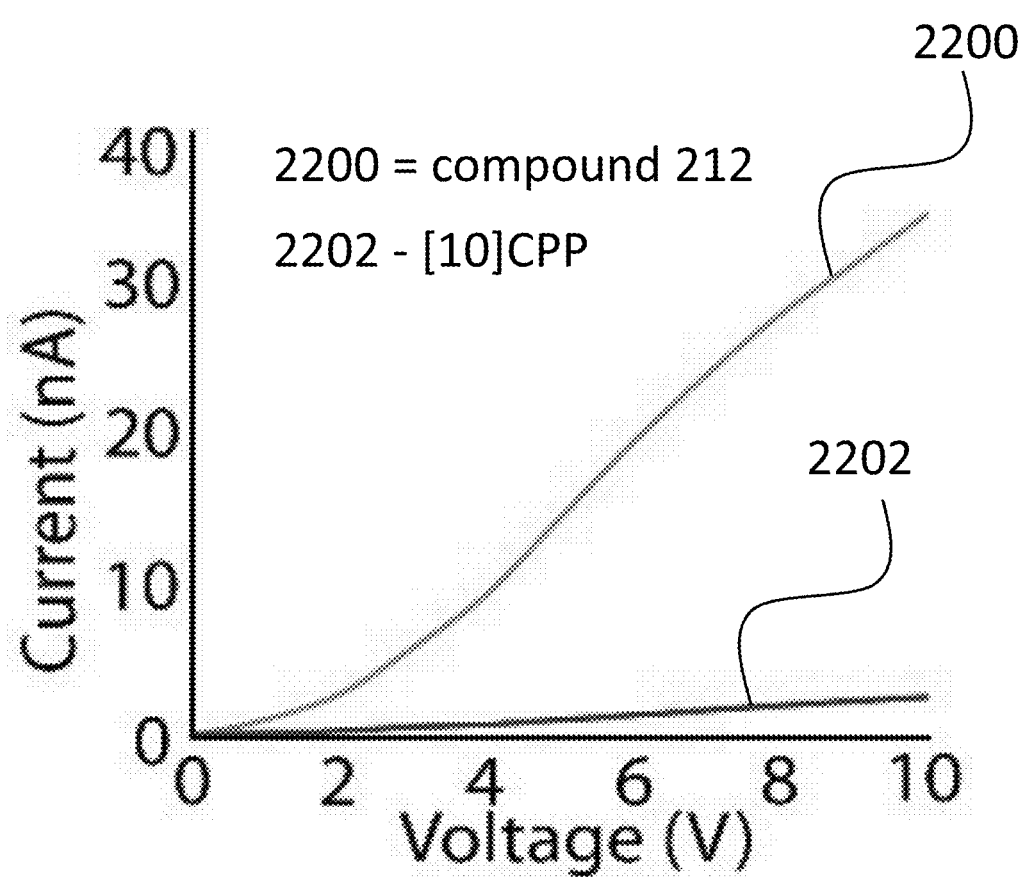
FIG. 22 is a graph of current (nA) as a function of voltage (V) showing results obtained from operation of electronic devices comprising a representative halogenated nanohoop compound ("212") and a non-halogenated nanohoop compound ("[10]CPP").

Noting the stark contrast between fluorinated nanohoop 212 and [10]CPP in the solid-state, the electrical conductivity of these organic materials was examined by constructing two-contact devices (FIG. 8) containing either fluorinated nanohoop 212 or [10]CPP. The devices were fabricated by spin-coating a tetrahydrofuran (THF) solution of either organic material onto pre-fabricated Si/SiO$_2$ chips with interdigitated gold electrodes. Current was then measured between 0 and 10 V under ambient conditions, resulting in linear I-V curves for both materials (FIG. 22). The results showed a dramatic difference between these two nanohoop compounds, where the calculated conductivity of the fluorinated nanohoop 212 was $(5.78\pm1.99)\times10^{-7}$ S cm$^{-1}$ more than an order of magnitude greater than that calculated for the all-carbon [10]CPP compound $(4.34\pm2.59)\times10^{-8}$ S cm$^{-1}$) and well within the range of conductivities reported for other analogous organic materials. Given that π-π interactions between adjacent molecules in the solid-state provides efficient electronic communication, the observed perfluoroarene-arene interactions (FIG. 6) in fluorinated nanohoop 212 are believed to play a strong role in this improved conductivity over [10]CPP as opposed to differences in frontier molecular orbital (FMO) energies. Additionally, it should be emphasized that these results represent the first example of the CPP-architecture being used as an organic electronic material.

Example 18

Figure 23:
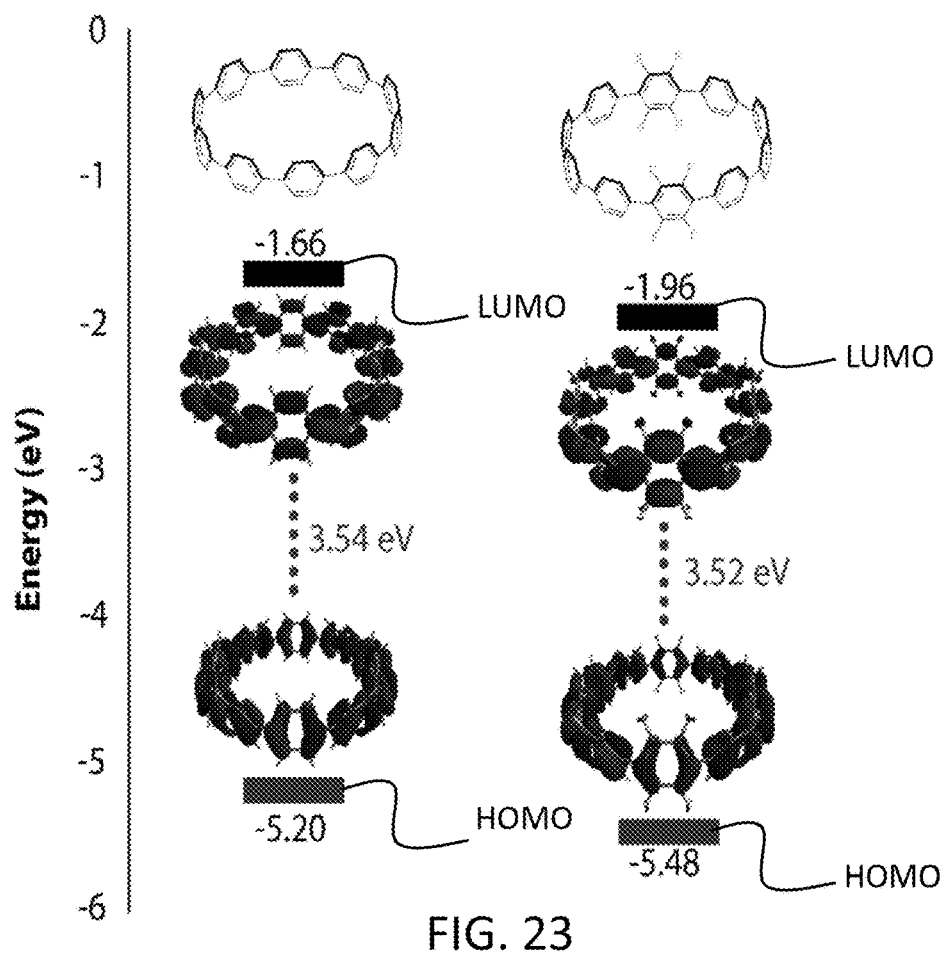
FIG. 23 illustrates DFT calculated frontier molecular orbitals and their respective energy levels for a representative halogenated nanohoop compound and a non-halogenated nanohoop compound.

To examine the effect of fluorination on the FMO energy levels, the electronic structure of 212 was examined through density functional theorem (DFT). See FIG. 23. It was found that the highest occupied molecular orbital (HOMO) and lowest unoccupied molecular orbital (LUMO) energy levels of fluorinated nanohoop 212 were comparable to those of [10]CPP, with calculated HOMO-LUMO energy gap levels being 3.53 and 3.54 eV for fluorinated nanohoop 212 and [10]CPP, respectively, suggesting similar electronic structure. This was corroborated through cyclic voltammetry, where the oxidation potential, relative to the ferrocene/ferrocenium redox couple, of fluorinated nanohoop 212 was found to be approximately 0.80 V, similar to that observed in [10]CPP (0.75 V). Additionally, the absorption and emission maxima ($\lambda_{abs}$ and $\lambda_{emi}$, respectively) of fluorinated nanohoop 212 ($\lambda_{abs}$=330 nm, $\lambda_{emi}$=467 nm) is similar to that of [10]CPP ($\lambda_{abs}$=338 nm, $\lambda_{emi}$=466 nm). Interestingly, similar nanohoop systems containing electron-deficient moieties have shown dramatic changes relative to the parent nanohoops, such as solvatofluorochromism and fluorescence quenching. The similarity between 212 and [10]CPP likely stems from a similar frontier molecular orbital (FMO)

distribution between 212 and [10]CPP. As a result, it this halogenation (e.g., fluorination) strategy can be leveraged to selectively modify the solid-state orientation of nanohoops as well as their derivatives, while advantageously leaving the electronic structure relatively unaltered.

Example 19

Device Fabrication and Conductivity Measurements:

The pre-fabricated substrates used for this study were purchased from Fraunhofer IPMS (4$^{th}$ generation "Position 2" OFET structures). These substrates consisted of a 150 mm n-doped silicon wafer layered with a 230±10 nm $SiO_2$ gate oxide and 30 nm interdigitated Au source/drain electrodes deposited onto a 10 nm ITO adhesion layer. Each substrate provided 16 transistor devices with variable gap spacings of 2.5, 5, 10, and 20 μm (4 of each per substrate), gap widths of 10 mm, and contact areas of 0.5×0.5 $mm^2$. Substrates were received from the manufacturer protected with AZ7217 resist. Prior to fabrication, substrates were cleaned by rinsing with acetone (necessary to remove the resist) followed by a methanol rinse, blow-drying the substrates with a stream of $N_2$ gas in between each rinse. Finally, substrates were plasma cleaned for 2 minutes directly before spin coating (it is important to prevent solvent from contacting substrate surfaces after plasma cleaning). Once the substrates were prepared, thin-film devices of fluorinated [10]CPP and [10]CPP for use in conductivity measurements were fabricated using the following procedure. A 2 mM concentrated solution of fluorinated [10]CPP in THF (10 mg/6 mL) was prepared for spin coating onto the substrates described above. Spin coating was carried out under ambient conditions by flooding substrates with the solution described above and spinning at 750 RPM for 60 seconds. These devices were then allowed to air-dry for at least 15 minutes before taking measurements. Devices of [10]CPP were fabricated by following this exact procedure with a 20 mg/7 mL solution of [10]CPP in THF.

Figure 24:
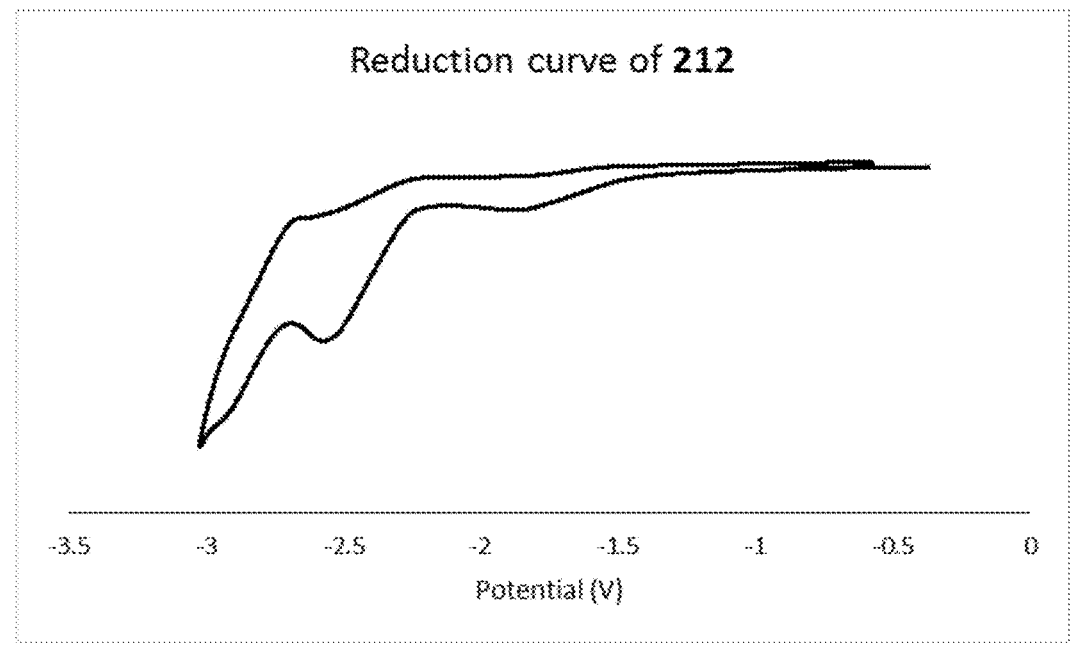
FIG. 24 is a reduction curve obtained from electrochemical analysis of a representative halogenated nanohoop compound.
Figure 25:
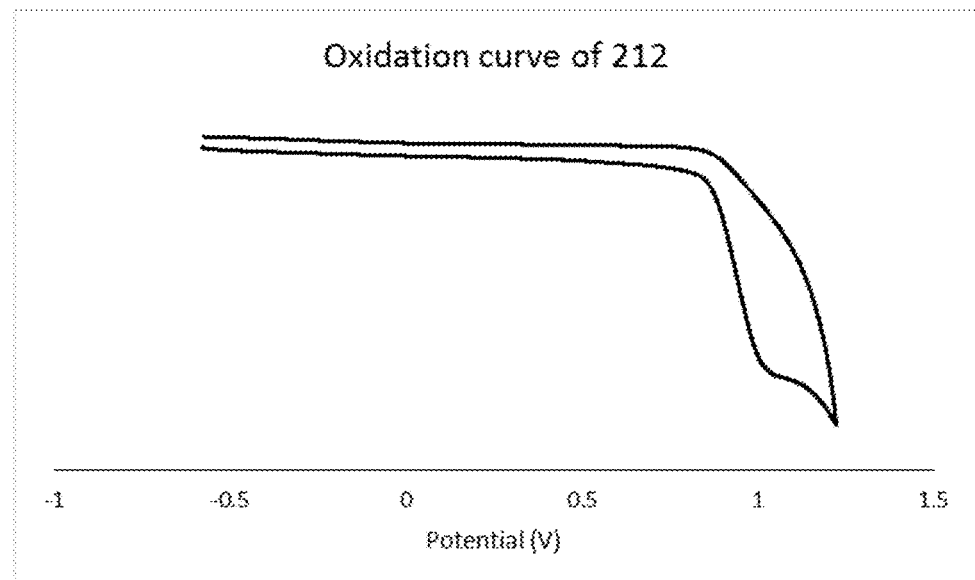
FIG. 25 is an oxidation curve obtained from electrochemical analysis of a representative halogenated nanohoop compound.

Conductivity was measured via two-contact measurements using a Sigmatone 1160 Series probe station and a Keithley 236 source-measure unit. All measurements were taken under ambient atmosphere and temperature. Current was measured as voltage was swept between 10 and −10 V, producing symmetric IV curves (only current from 0 to 10 V shown in text). Conductivity was calculated using the following equations:

$$G=I/V$$

$$\sigma=(G \cdot L)/(t \cdot w)$$

where G is electrical conductance, L is the gap spacing (variable between 2.5. 5. 10, and 20 μm in these studies), t is film thickness (25 nm on average for both materials, as measured by optical profilometry, and w is the gap width of the interdigitated electrodes (10 mm for all devices). Electrochemical results are illustrated in FIGS. 24 and 25, which illustrate the reduction curve and oxidation curve of compound 212, respectively.

Example 20

Thin-Film Characterization:
Optical Microscopy

Figure 26:
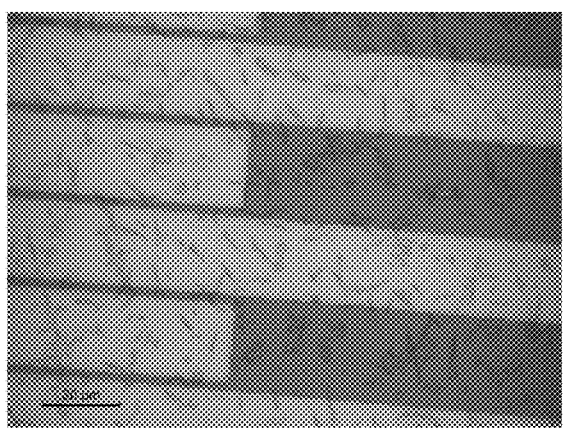
FIG. 26 is a magnified optical microscope image of a thin-film comprising a representative halogenated nanohoop compound.
Figure 27:
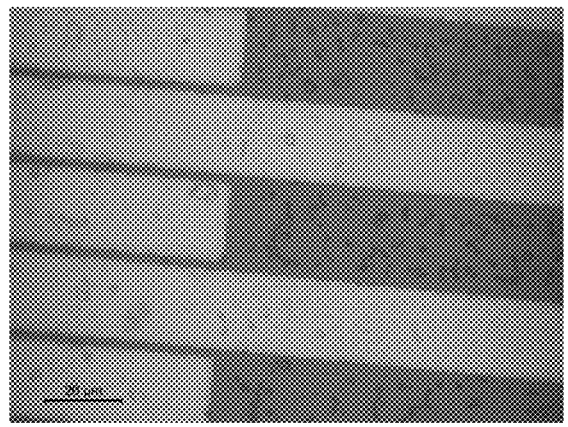
FIG. 27 is a magnified optical microscope image of a thin-film comprising a non-halogenated nanohoop compound.

The respective film morphologies of fluorinated [10]CPP and [10]CPP devices were analysed via optical microscopy using a Leica DM2500 M optical microscope at 100× magnification; results are shown by FIGS. 26 and 27.

Thin-Film X-Ray Diffraction

Figure 28:
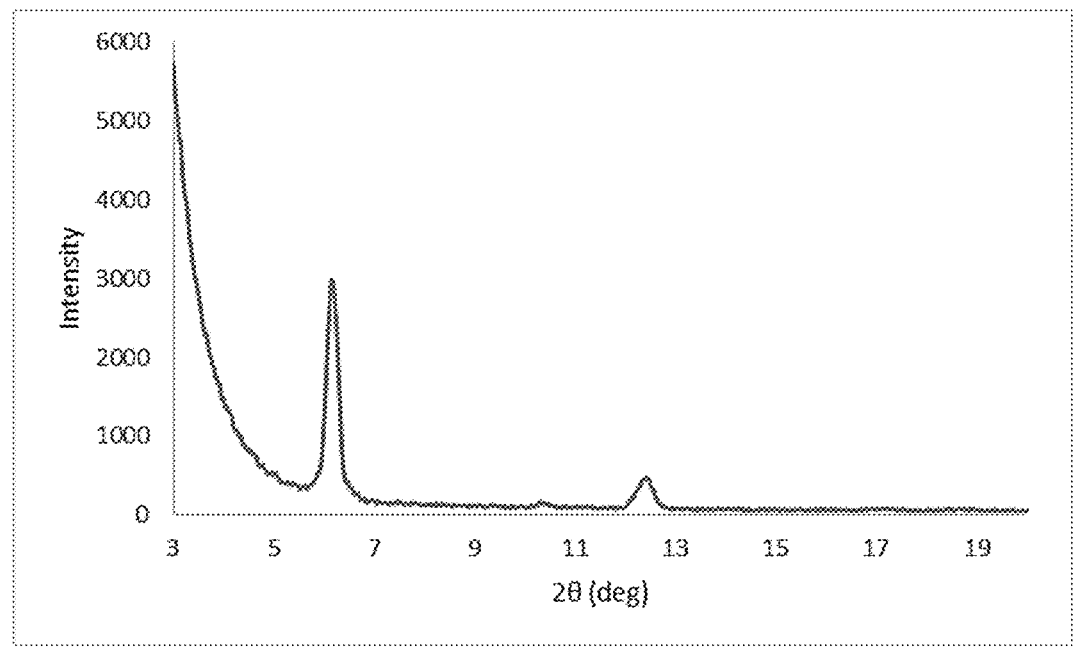
FIG. 28 is an XRD pattern for a representative halogenated nanohoop-containing thin-film.
Figure 29:
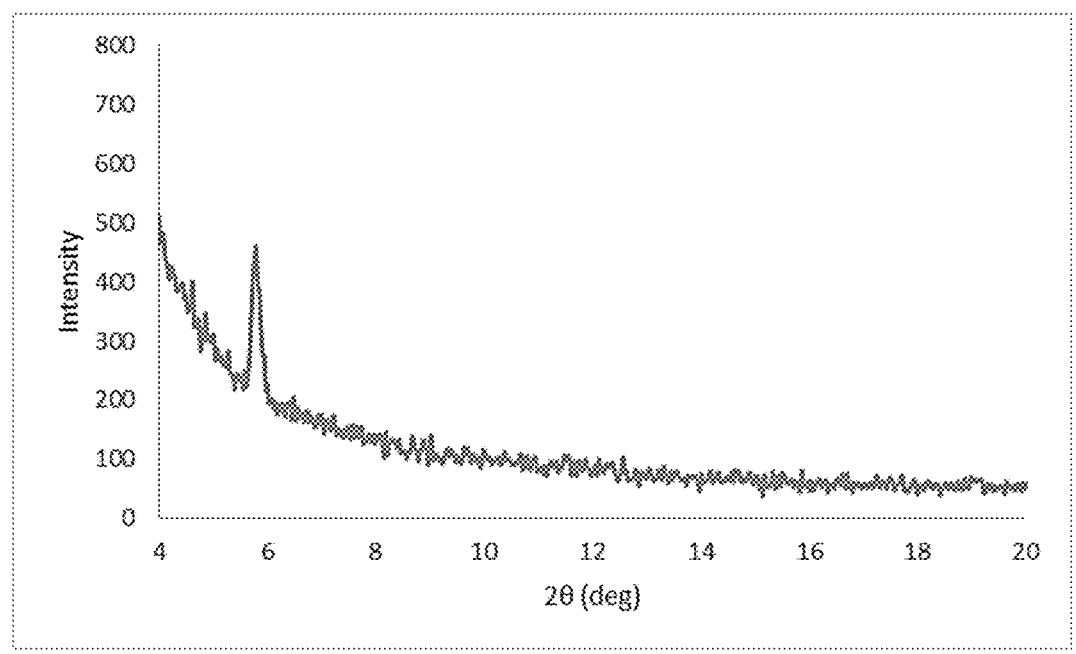
FIG. 29 is an XRD pattern for a non-halogenated nanohoop-containing thin-film.

Thin-Film XRD analysis was performed using a Rigaku SmartLab X-ray diffractometer using a Bragg-Brentano para-focusing configuration, with the instrument being operated at 40 kV and 30 mA. Thin-films were mounted on a horizontal sample stage on a 600 mm diameter goniometer equipped with a suitable detector. Data were collected using a step width of 0.013° and a speed of 0.4° per minute with a 2θ range of 3.0°-40.0°. The acquired XRD spectra are illustrated in FIGS. 28 and 29.

Example 21

Thin-Film Soaking:

Soaking experiments were carried out on drop-cast thin-films of Fluorinated [10]CPP and [10]CPP on glass slides. Gold Seal® Pre-Cleaned Micro Slides were cut into 2.0×1.5 cm segments using a diamond scribe. These glass substrates were cleaned with soap and DI water and blown dry with $N_2$ gas. This was followed by acetone and methanol rinses, with the substrates being blown dry with $N_2$ gas in between each rinse. The glass substrates were flooded with a 10 mg/6 mL solution of fluorinated [10]CPP in THF and allowed to dry in open air for at least 2 hours to afford drop-casted films of the fluorinated nanohoops. [10]CPP films were made using this exact procedure but with a solution of 20 mg/7 mL of the compound in THF. The air-dried films were then placed in scintillation vials containing either a saturated solution of $C_{60}$ in hexanes or just pure hexanes (as a control), after which the vials were capped and the films were allowed to soak for 3 hours. After soaking, the films were rinsed with hexanes and blown dry with $N_2$ gas before being qualitatively analyzed for fluorescence quenching using a standard UV lamp.

Example 22

Figure 31A:
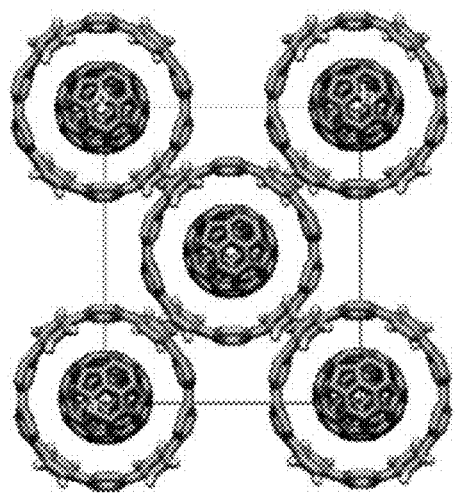
FIGS. 31A-31D show solid state interactions between a halogenated nanohoop embodiment and C60 (FIGS. 31A, 31C, and 31D), as well as solid state interactions between a non-halogenated nanohoop compound and C60 (FIG. 31B).
Figure 31B:
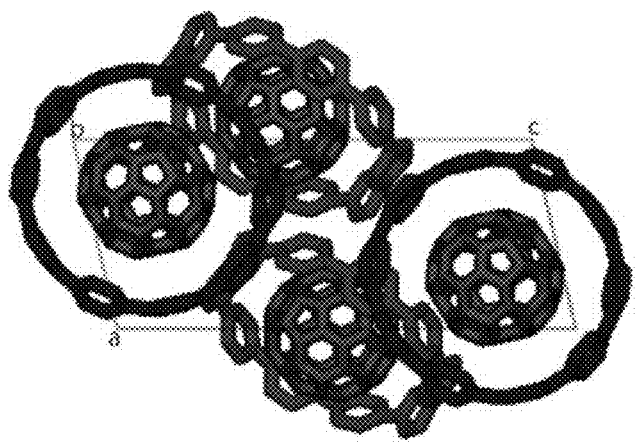
Figure 31C:
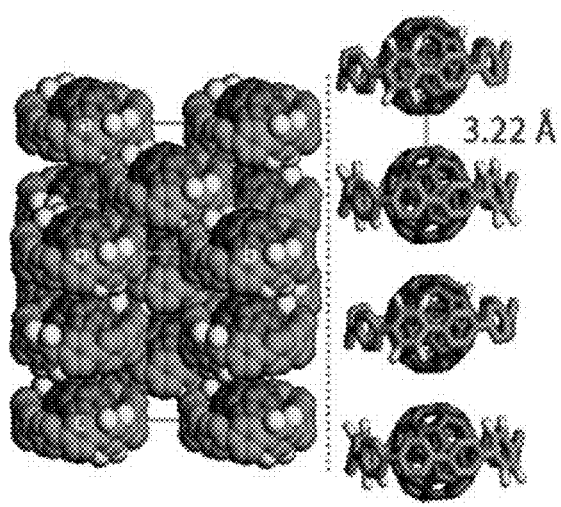
Figure 31D:
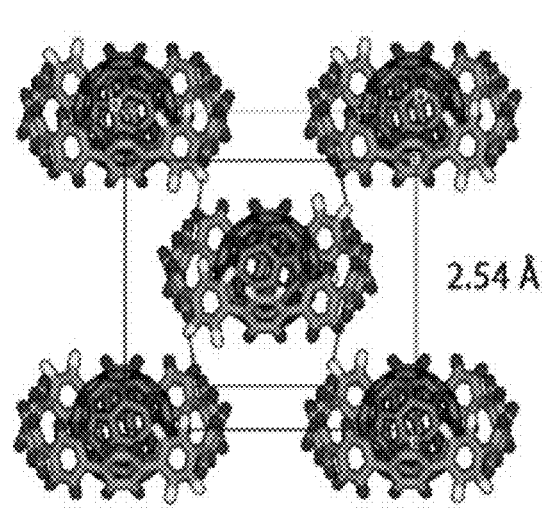

In this example, the solid state of a nanohoop-$C_{60}$ host-guest complex was analysed. Dark red single-crystals of the fluorinated nanohoop 212@$C_{60}$ complex suitable for X-ray crystallography were grown via vapor diffusion of diethyl ether into a dilute THF/1,2-dichlorobenzene/toluene (1:1:1) solution of fluorinated nanohoop 212 and $C_{60}$ (1:1) with the observed packing structure shown in FIG. 31A. For comparison, the previously reported packing structure observed in the [10]CPP@$C_{60}$ host-guest complex is shown in FIG. 31B. In the case of 212@$C_{60}$, the observed packing is very similar to that observed in CNTs, where the columnar channels pre-organize the $C_{60}$ guests into 1D columnar arrays (FIG. 31C). Further analysis revealed the absence of perfluoroarene-arene interactions; however, short intermolecular aryl C—F/aryl C—H and $C_{60}$ ... $C_{60}$ distances were observed (FIG. 31D). This suggests fluorinated nanohoops can direct and likely pre-organize other guest molecules into columnar 1D arrays.

Example 23

In this example, computation analysis of nanohoop compound embodiments was carried out. The structures of all unique yet repeating dimers are extracted from the corresponding crystal structures, which are used rigidly in this example. Solvent molecules are removed in the case of compound 212 to exclusively address the interaction energies between pairs of non-covalently interacting molecules, and to compare with previous theoretical estimates for pristine [10]CPP. The intermolecular interaction energy of every pair, $\Delta E_{interaction}$ or simply $\Delta E$, is calculated by subtracting the monomer energies (at the dimer geometry) from that of the dimer, with a negative value thus implying a weakly bound dimer. The effect of both intra- and intermolecular non-covalent interactions is incorporated by resorting to the D3(BJ) method for dispersion-corrected DFT, employing the B3LYP functional and the large cc-pVTZ basis set to avoid basis set superposition errors. The dimers were extracted and further manipulated with the use of the Mercury and Avogadro visualizers. Calculations were carried out using the Gaussian 09 (D.01) package.

The most effective molecular packing is determined by the size and shape of the individual molecules together with the operating intermolecular forces. In the case of having polar substituents without a significant permanent dipole moment, higher-order inductive effects (e.g. quadrupole-quadrupole) might become competitive with dispersion forces, with the former showing a distance dependence between interacting units of $R^{-5}$ instead of the typical $R^{-6}$ of the latter. Then, the quadrupole-quadrupole interactions, or in general the distributed multipoles, need to be maximized while keeping the densest possible packing. In other words, both electrostatic and dispersion contributions to the packing must be handled in a balanced way.

The molecular cohesive or lattice energy can be estimated from the individual interaction energies of the dimers through the expression:

$$U = \Sigma_i^{dimers} m_i \Delta E_{interaction}^{(i)}.$$

with $m_i$ being the number of symmetry-unique pairs taking one central molecule as reference, and $\Delta E^{(i)}_{interaction}$ being each of the interaction energies calculated before. The result must be half-divided to avoid a double counting of interactions, and it leads to a value of 54.3 kcal/mol, comprised between those calculated by the same methodology for [6]CPP (51.6 kcal/mol) and [12]CPP (57.6 kcal/mol). However, changing the crystallization conditions can yield two different polymorphs of [6]CPP only differing by roughly few kcal/mol.

Given that the inclusion of electron-deficient tetrafluorophenylene units was suspected to induce the striking differences in crystal morphology between the fluorinated nanohoops described herein and their all-hydrocarbon counterparts, these phenomena were rationalized with an analysis of the aromatic quadrupole moments ($Q_{zz}$) of these compounds. The amplitude of the traceless molecular quadrupole moment of compound 212 amounts to $1.21 \times 10^{-38}$ C·m$^2$, being thus considerably high among organic compounds. Analysis of model systems benzene, 1,2,3,4-tetrafluorobenzene, 1,2,3,5-tetrafluorobenzene, and 1,2,4,5-tetrafluorobenzene, taken from the literature and calculated at the sufficiently accurate MP2/cc-pVTZ level, reveal that, with varying fluorination patterns, the $Q_{zz}$ of benzene evolves from $-29.2 \times 10^{-40}$ C·m$^2$ to $8.4 \times 10^{-40}$ C·m$^2$, $11.4 \times 10^{-40}$ C·m$^2$, and $13.6 \times 10^{-40}$ C·m$^2$, respectively. Thus, two conclusions can be drawn from these data: (i) a sign change is confirmed going from the unsubstituted to the substituted compounds due to the presence of the electronegative fluorine atoms; and (ii) the substitution pattern of fluorine atoms found in compound 1 (i.e. on the 1, 2, 4, and 5 positions) is, in principle, the most favorable for maximizing the molecular quadrupole moment among the set of tetrafluorosubstituted aromatic compounds explored.

A 1:1 mixture of molecules with opposite electric quadrupole moments, exemplified in literature by benzene ($Q_{zz} = -29.0 \times 10^{-40}$ C·m$^2$) and hexafluorobenzene ($Q_{zz} = 31.7 \times 10^{-40}$ C·m$^2$), is known to form a slightly shifted ($\pi$-stacked) sandwich-like structure with alternating molecular positive and negative quadrupole moments. For compound 212, molecules belonging to the same layer are precisely arranged to maximize these face-to-face interactions between unsubstituted and tetrafluorosubstituted units, helped by the large stabilization energy of $-11.3$ kcal/mol calculated for this configuration, and thus driving the self-assembly of the whole morphology. This design principle leaves enough space for solvent molecules to appear in those faces (i.e. nanopores) missing that particular orientation between the unsubstituted and tetrafluorosubstituted units. This situation also occurs for the corresponding [12]CPP case. The crystal packing of [12]CPP with three tetrafluorinated units also occurs, where the mutual orientation between units prevails.

Figure 32:
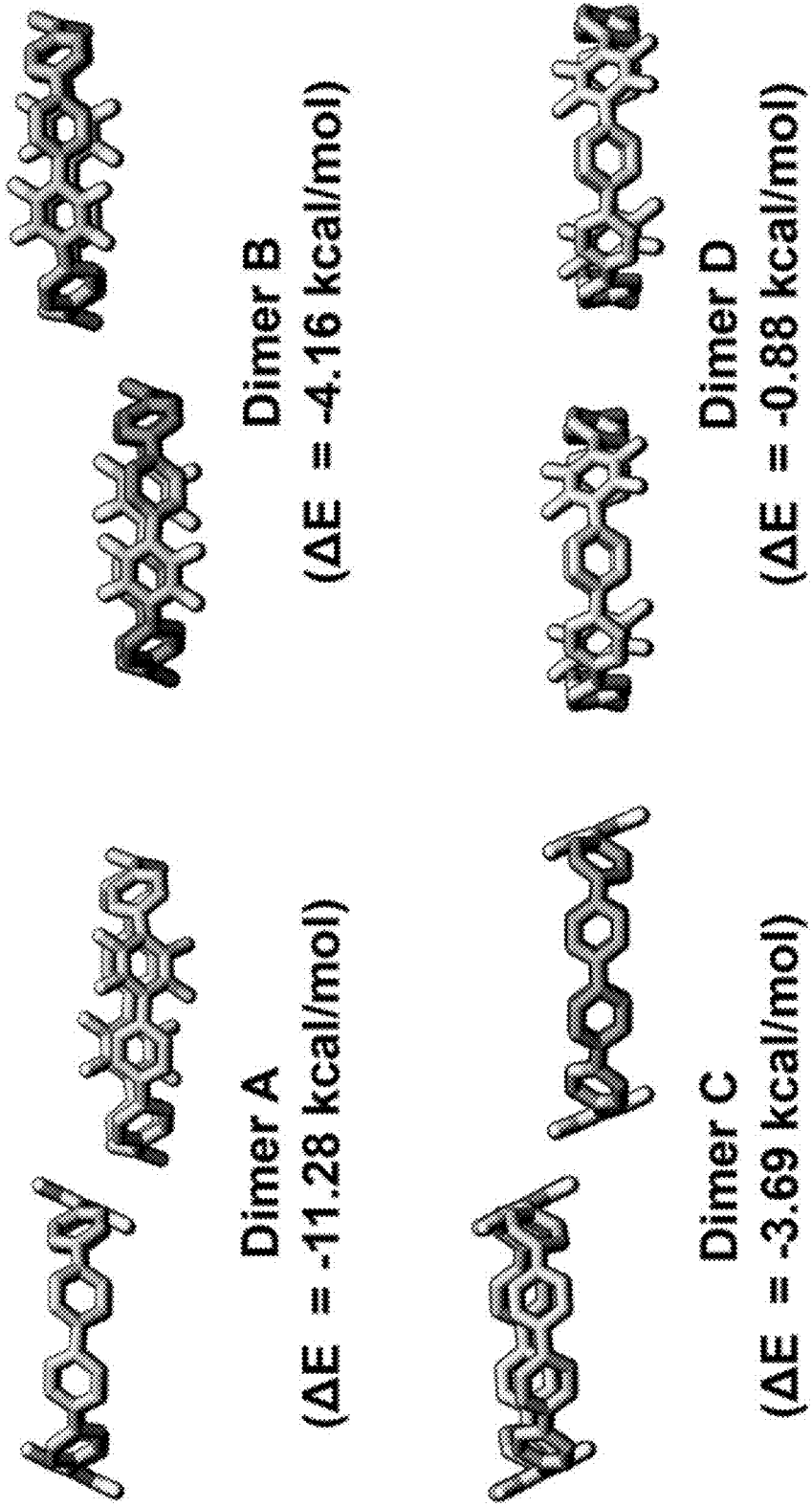
FIG. 32 shows complementary dimers extracted from the crystalline structure of a representative halogenated nanohoop compound 212 and the respective interaction energies of the dimers.

Given that interactions between fluorinated and non-fluorinated aryl rings were hypothesized to play a major role in the self-assembly of 212 into tubular arrays. To shed light of the energetic contributions of these arene-perfluoroarene interactions, the various lateral interactions observed in the crystal structure of 1 were explored, represented by the dimers in FIG. 32. Interestingly, Dimer A, representative of the arene-perfluoroarene interaction observed in the crystal structure of 212, was found to have a markedly high interaction energy compared to the other three dimers studied, implying that arene-perfluoroarene interactions are indeed dominant in the lateral stabilization of the tubular system afforded by 212.

Analysis of the vertical, tubular alignment of 212 was carried out on the repeating vertical dimer (FIG. 33A) found in the crystal structure of 212. As discussed above, this assembly is attributed to multiple C—H—F interactions, or hydrogen bonds. Interestingly, the hydrogen bond R—X.Y, where X is a halogen atom covalently bound to the R group and Y is some $\pi$-system, is highly directional (more directional, in fact, than the more common hydrogen bond) and promotes a quasi-linear R—X.Y geometry. The aryl C—H—F bonds are here comprised between 2.53 and 2.85 Å, depending on the relative orientations between interacting rings, and are thus found below or close to the sum of the van der Waals radii of H (120 μm) and F (147 μm). This dimer displays a remarkably large interaction energy of $-23.2$ kcal/mol, substantially higher than the value of $-17.3$ ($-14.4$) kcal/mol found before for the corresponding tubular-like (herringbone) dimer of the pristine [10]CPP. Overall, analyzing in detail the packing of nanohoop 212, the number and position of the fluorine-substituted units determine the crystalline structure based mostly on two energetically stable interactions: tubular-like (Dimer A, see FIG. 32) and intralayer (Dimer C, see FIG. 32). While the tubular-like is kept by favorable hydrogen bonding, the intralayer is promoted by maximizing interactions between molecular quadrupole moments.

Figure 33A:
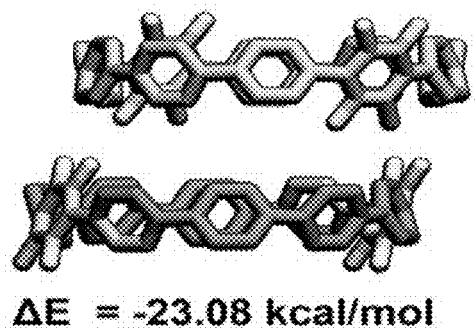
FIGS. 33A-33E show interaction energies of the tubular-like dimer of halogenated nanohoop 212 (FIG. 33A) and halogenated nanohoop 212 following the removal of fluorine atoms on one phenylene unit (FIG. 33B), two phenylene units (FIG. 33C), three phenylene units (FIG. 33D), and four phenylene units (FIG. 33E).
Figure 33B:
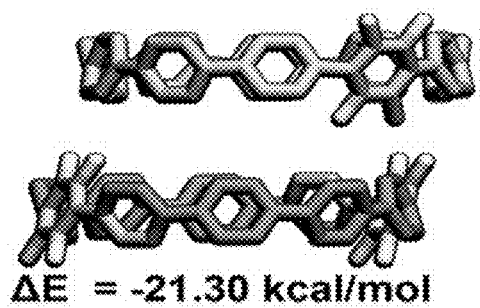
Figure 33C:
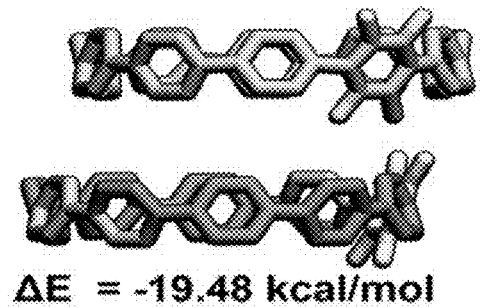
Figure 33D:
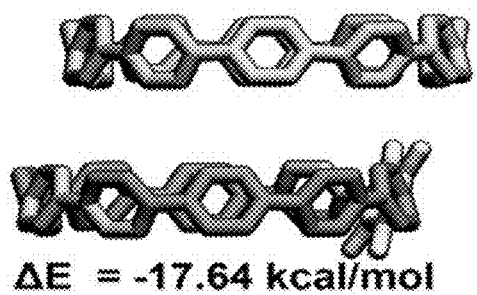
Figure 33E:
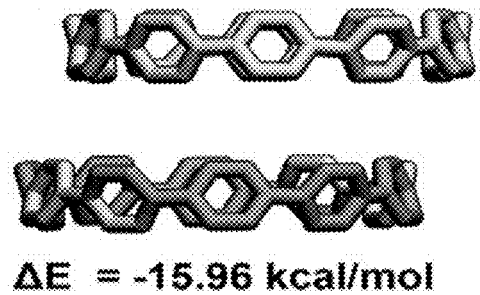

As another example, the dimer displayed in FIG. 33A is systematically deprived of tetrafluorinated rings, to infer concomitantly the effect on interaction energies of these groups, with the corresponding results shown in FIG. 33B-33D. The marked decrease of interaction energies would also reduce the whole cohesive energy, thus largely affecting the preferred mode of packing. As a matter of example, keeping only one tetrafluorinated ring on each monomer at the optimal crystallographic positions for compound 212, the newly estimated cohesive energy reduces to 37.9 kcal/mol; thus judged too low to become competitive with other supramolecular structures.

Furthermore, the evolution of these values as a function of the number of tetrafluorinated interacting units per dimer is presented in FIG. 34, for which a linear decrease of the interaction energy as a function, in other words, of the number of aryl C—H—F bonds is obtained. When considering the value of −15.96 kcal/mol when compound 212 is completely de-fluorinated, as compared to the case of pristine [10]CPP (see FIGS. 35A and 35B), it was observed that: (i) the interaction energy of the tubular-like dimer (−17.32 kcal/mol, FIG. 35A) of pristine [10]CPP is slightly lower due to structural relaxation effects; and (ii) the herringbone pattern of [10]CPP (−14.38 kcal/mol, FIG. 35B) becomes close in energy, actually within the threshold of 1-2 kcal/mol for which polymorphism can be predicted in real samples.

These computational analyses reveal that solid-state orientations that allow for arene-perfluoroarene interactions and C—H—F interactions are indeed energetically favorable and presumably result in the nanotube-like architectures observed. This unique nanotube-like packing enables new pathways for studying mass and energy transport through surface-bound π-rich membranes as well provide access template driven sytheses of 1D materials.

VIII. Overview of Several Embodiments

In some embodiments, the halogenated nanohoop compounds described herein can have structures satisfying Formula I

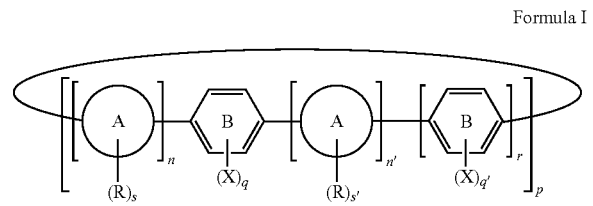

Formula I wherein each A ring independently is an aromatic ring that does not require a halogen atom;

each X independently is chloro, fluoro, bromo, or iodo;

each R independently is an electron-donating group or an electron-accepting group;

each n, n', and r independently is an integer selected from 0 to 24;

p is an integer selected from 1-12, provided that when each of n, n', and r is 0, then p is at least 6, and provided that when p is 1, then at least one of n, n', or r is 5;

each s and s' independently is an integer selected from 0 to 4; and each q and q' independently is an integer selected from 1 to 4.

In such embodiments, each A ring independently is phenyl optionally substituted with one or more electron-donating substituents; benzo[1,2-b:4,5-b']dithiophenyl optionally substituted with one or more electron-donating substituents; benzo[1,2-b:4,5-b']difuranyl optionally substituted with one or more electron-donating substituents; 1,5-dihydropyrrolo[2,3-f]indolyl optionally substituted with one or more electron-donating substituents; phenyl substituted with one or more electron-accepting substituents; pyridinyl substituted with an aliphatic or aryl group; benzo[c][1,2,5]thiadiazolyl; benzo[c][1,2,5]oxadiazolyl; or 2H-benzo[d][1,2,3]triazolyl.

In any or all of the above embodiments, the one or more electron-donating substituents is alkoxy, thioether, amide, amine, hydroxyl, thiol, acyloxy, aliphatic, aryl, or combinations thereof.

In any or all of the above embodiments, the electron-accepting substituents is aldehyde, ketone, ester, carboxylic acid, acyl, acyl halide, cyano, sulfonate, nitro, nitroso, quaternary amine, alkyl halide, or combinations thereof.

In any or all of the above embodiments, the A ring independently is 4,4-dimethyl-4H-cyclopenta[2,1-b:3,4-b']dithiophene, phenyl, or combinations thereof.

In any or all of the above embodiments, each X is fluoro.

In any or all of the above embodiments, q and q' independently are 1, 2, 3, or 4.

In any or all of the above embodiments, n' and r each are 1 and p is 6.

In any or all of the above embodiments, the nanohoop compound has a structure satisfying any one or more of Formulas IIA-IIL as described herein.

In any or all of the above embodiments, the compound has a structure satisfying any one or more of Formulas IIIA-IIIC Formula IIIA

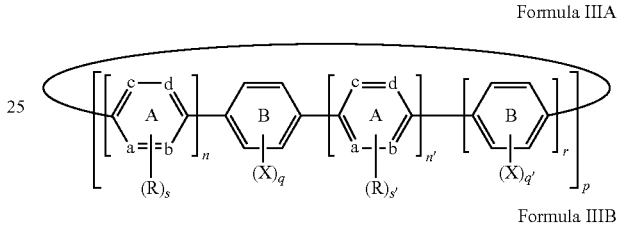

Formula IIIB

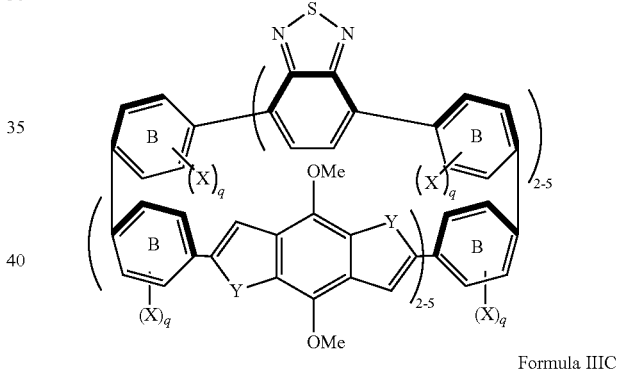

Formula IIIC

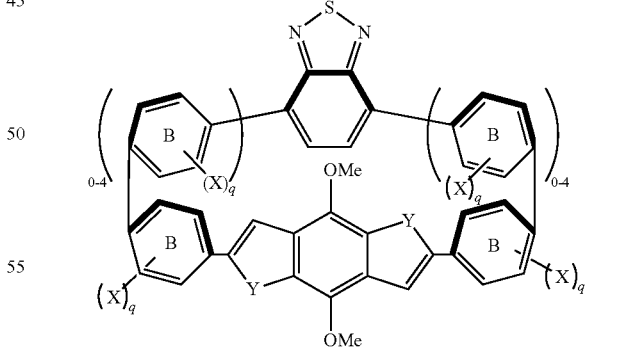

wherein each a, b, c, and d can be selected from carbon or nitrogen and each Y independently can be selected from O, S, or NH.

In any or all of the above embodiments, the compound can be selected from the compounds described in Table 2.

In any or all of the above embodiments, the compound is selected from the compounds described in Table 3.

Also disclosed herein are embodiments of an assembly, comprising a plurality of nanohoop compounds that are arranged, through one or more C—H/C—X interactions, in a column-like configuration, wherein at least one of the nanohoop compounds is a compound according to any or all of the above embodiments.

Also disclosed herein are embodiments of a device, comprising a halogenated nanohoop compound as disclosed in any or all of the above embodiments, or an assembly thereof, wherein the device is an energy storage device, a nanoreactor, an electronic device, a biological transport device, or a chemical device.

In some embodiments, the energy storage device is a capacitor, an electrode, a solar cell, a fuel cell, or a battery.

In some embodiments, the electronic device is a two-contact electronic device.

In some embodiments, an assembly according to any or all of the above assembly embodiments forms the nanoreactor.

In any or all of the above embodiments, the nanoreactor further comprises one or more guest species.

Also disclosed herein are embodiments of methods for making a halogenated nanohoop compound. In some embodiments, the method comprises cross-coupling a compound having a structure satisfying Formula A and a compound having a structure satisfying a Formula B to form a nanohoop precursor having a structure satisfying Formula C; and deprotecting the nanohoop precursor in the presence of acetic acid to form the halogenated nanohoop compound; wherein Formula A is

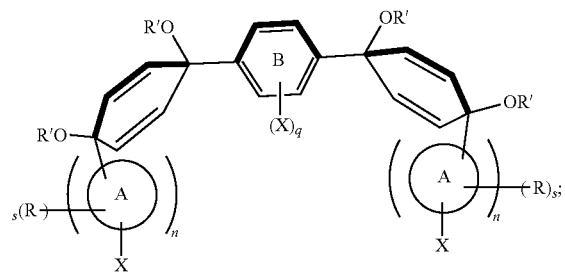

Formula B is

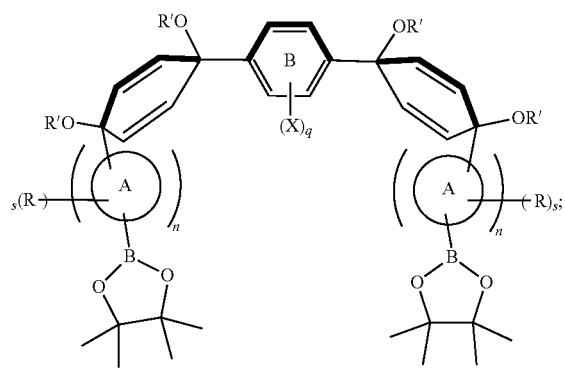

and

Formula C is

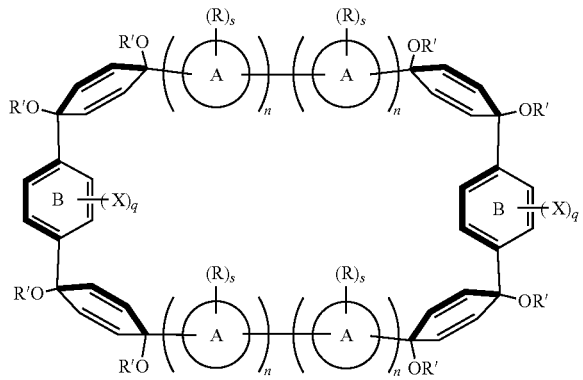

and wherein each R' independently is a silyl protecting group, each A ring independently is aromatic ring that does not require a halogen atom; each R independently is an electron-donating group or an electron-accepting group; each X independently is chloro, fluoro, bromo, or iodo; each s independently is an integer selected from 0 to 4; each q independently is an integer selected from 1 to 4; and each n independently is an integer selected from 0 to 24.

In some embodiments, the cross-coupling is performed using a transition metal-based catalyst and a base.

In any or all of the above embodiments, the transition metal-based catalyst is a palladium catalyst.

In view of the many possible embodiments to which the principles of the present disclosure may be applied, it should be recognized that the illustrated embodiments are only preferred examples of the present disclosure and should not be taken as limiting the scope of the disclosure. Rather, the scope is defined by the following claims. We therefore claim as our invention all that comes within the scope and spirit of these claims.

We claim:

1. A compound selected from

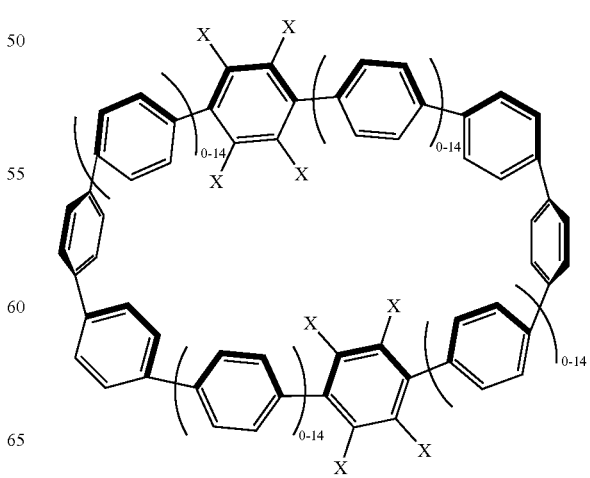

93
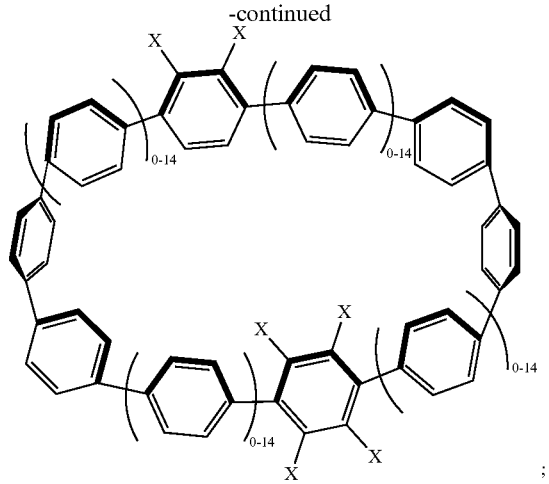
;
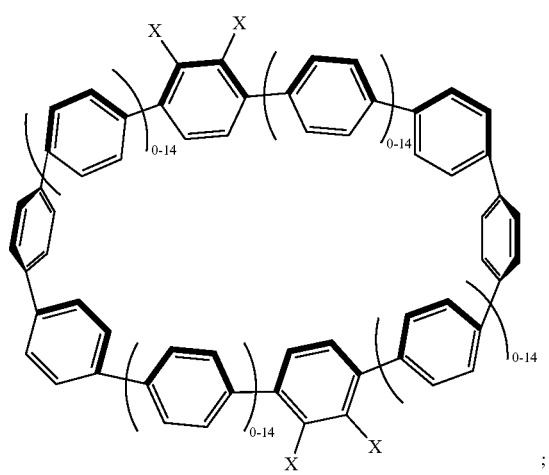
;
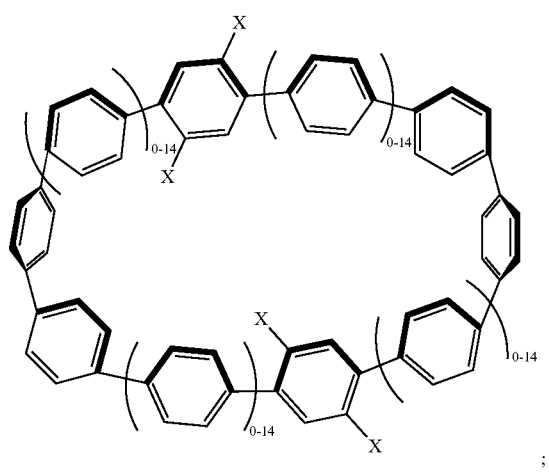
;
94
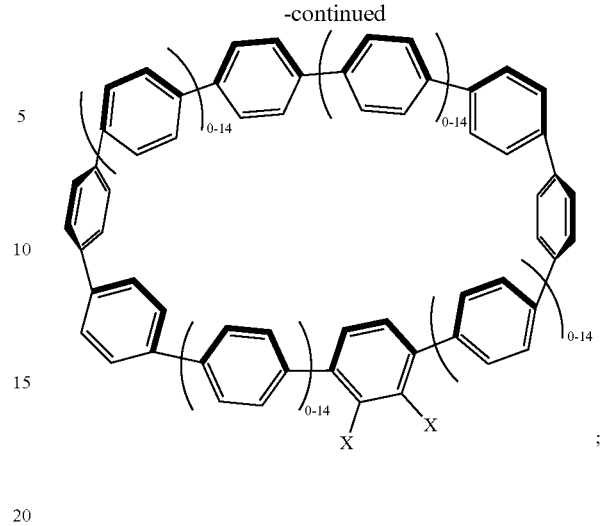
;
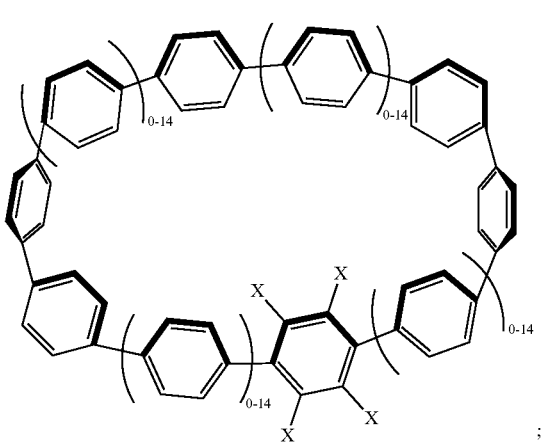
;
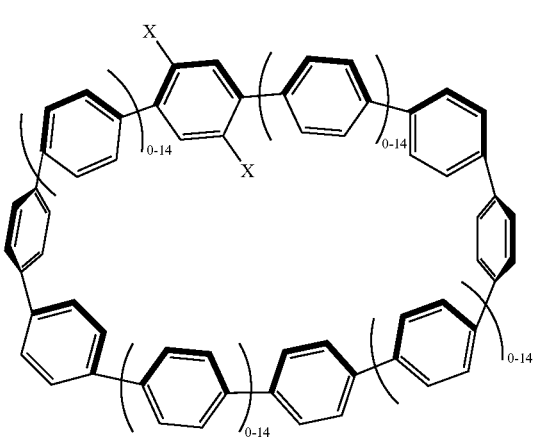
;

-continued
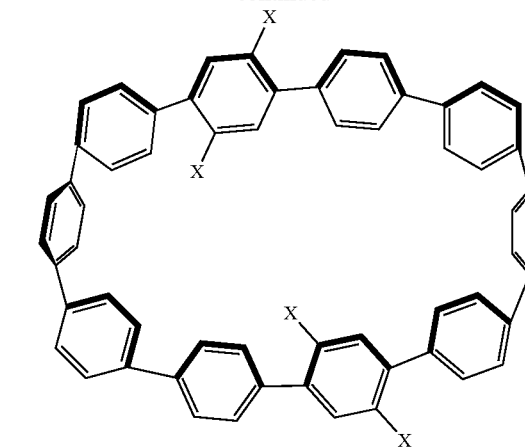
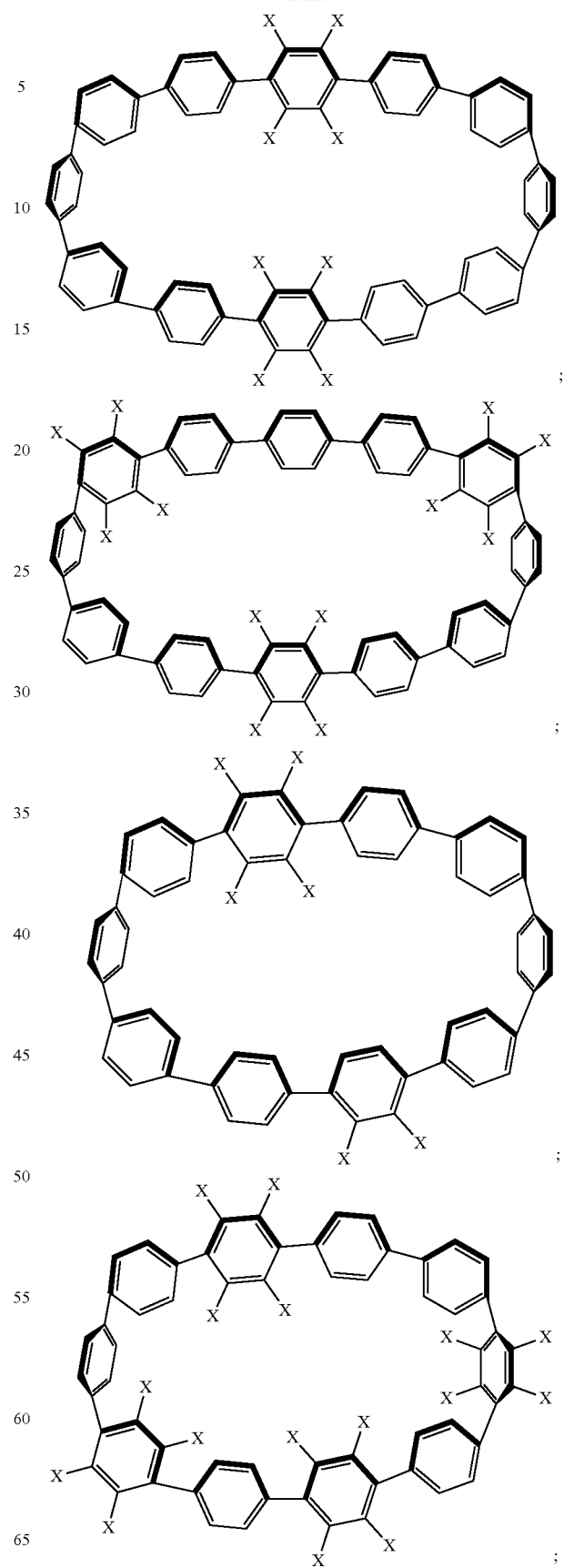

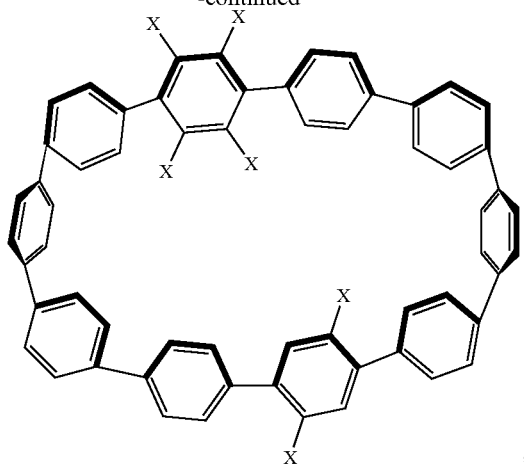
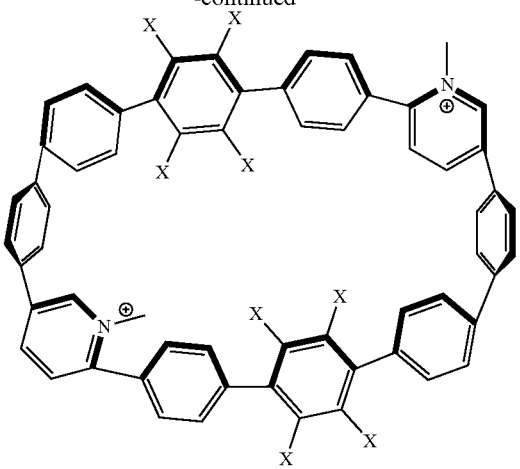
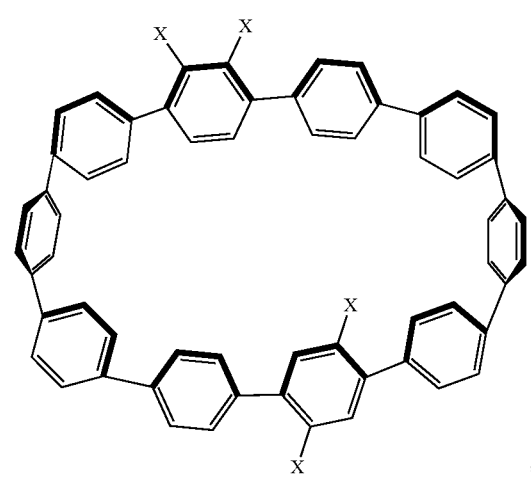
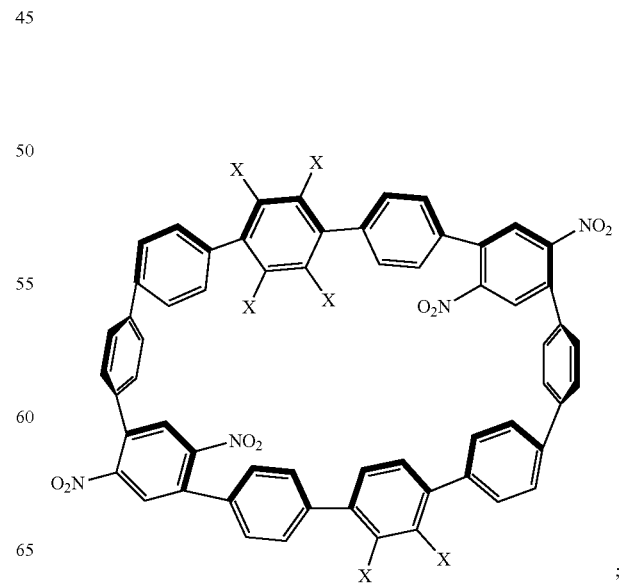

99
-continued
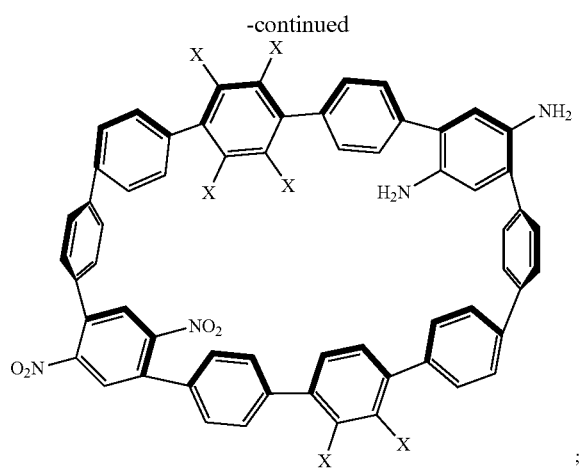
;
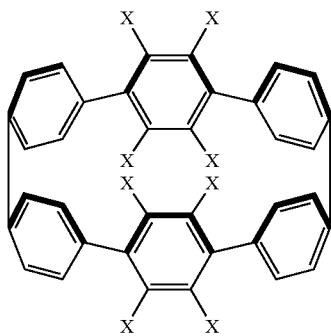
;
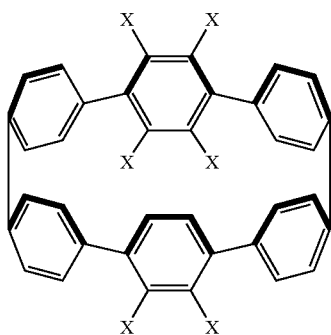
;
100
-continued
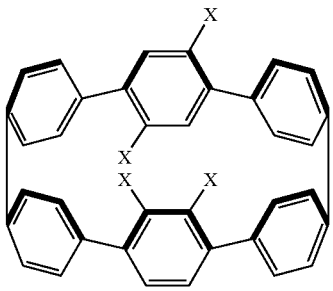
;
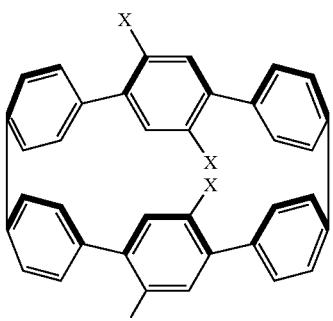
;
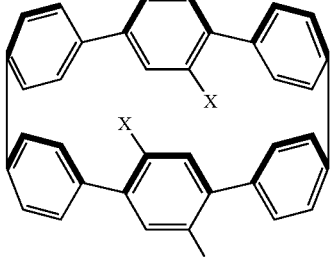
;
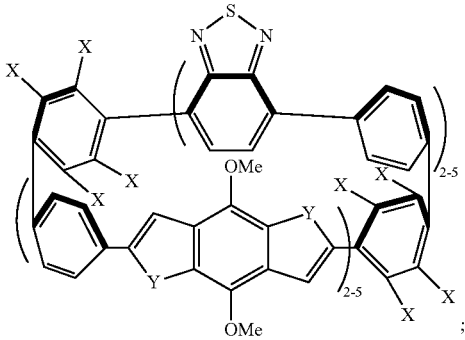
;
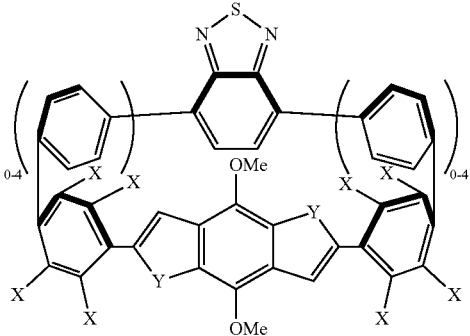
; or -continued
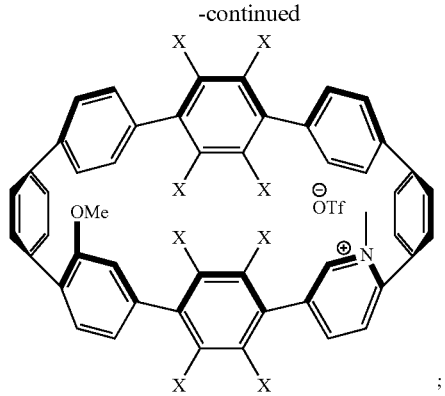
wherein each X independently is chloro, fluoro, bromo, or iodo; and each Y independently is O, S, or NH.
2. The compound of claim 1, wherein the compound is selected from
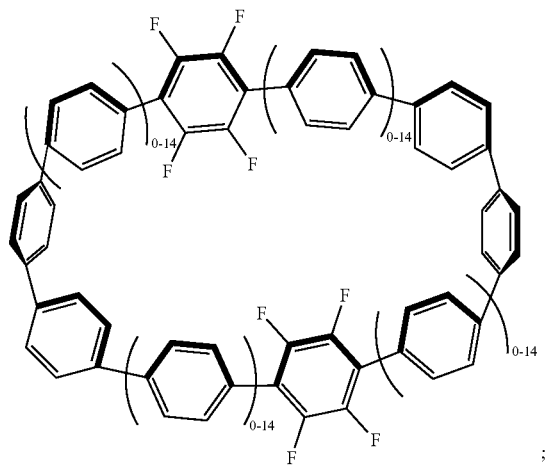
;
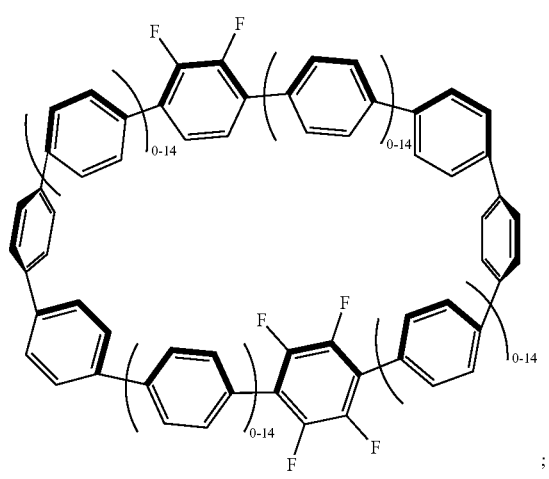
;
-continued
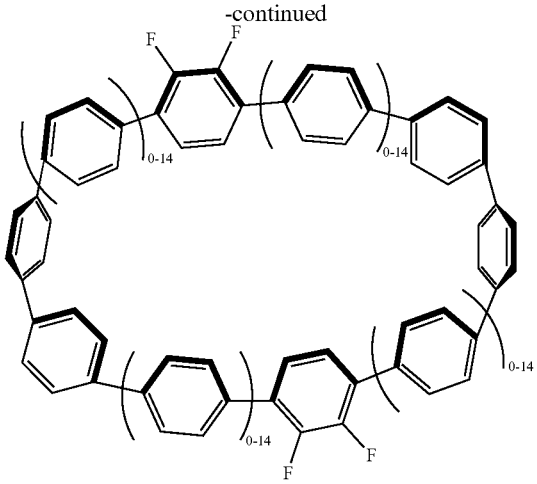
;
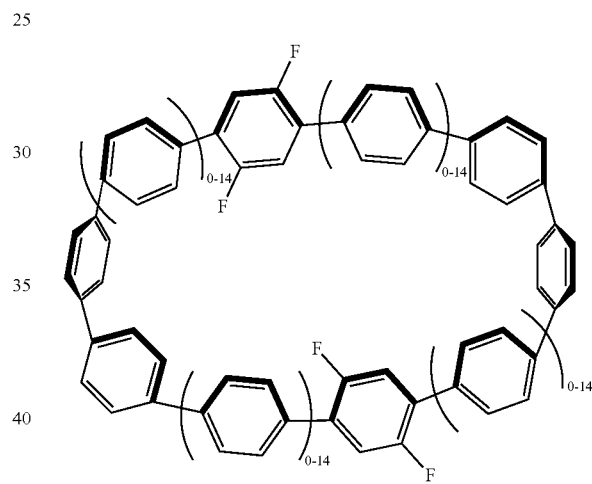
;
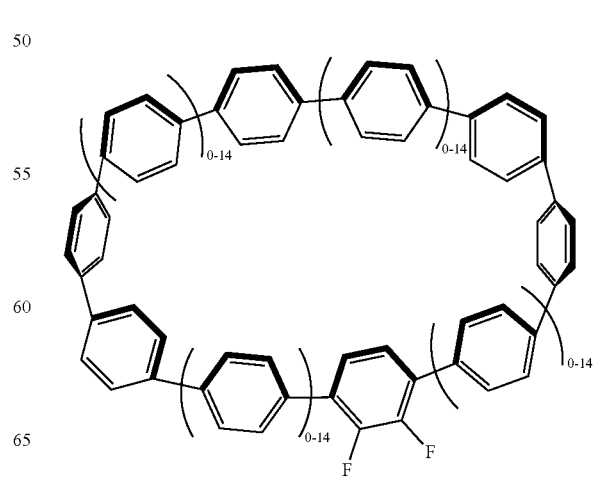
;

103
-continued
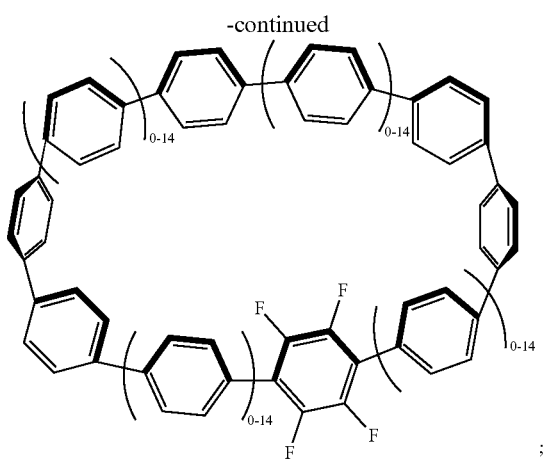
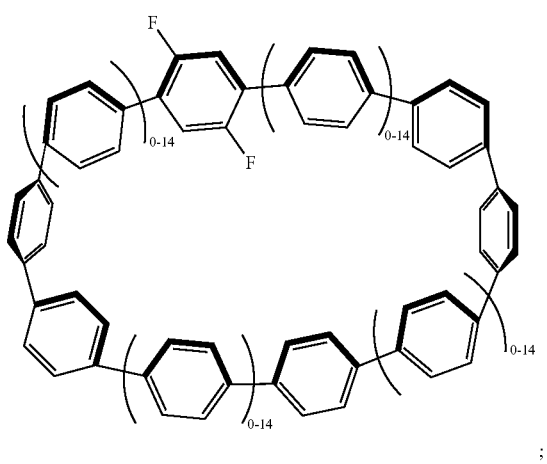
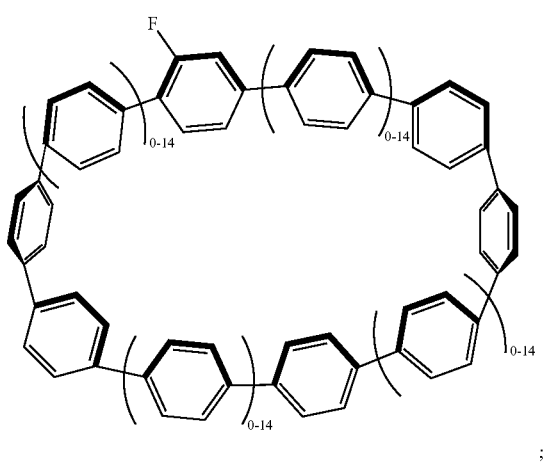
104
-continued
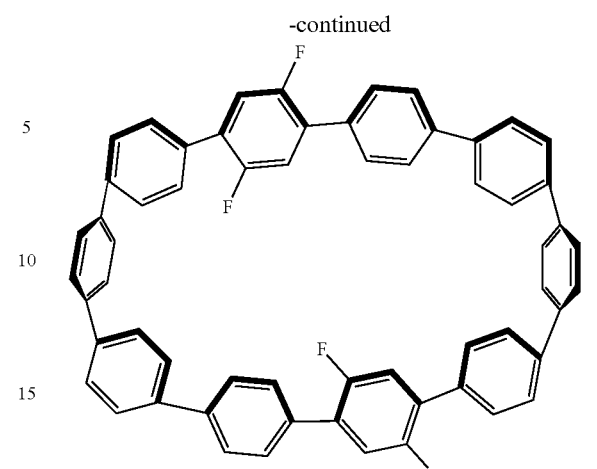
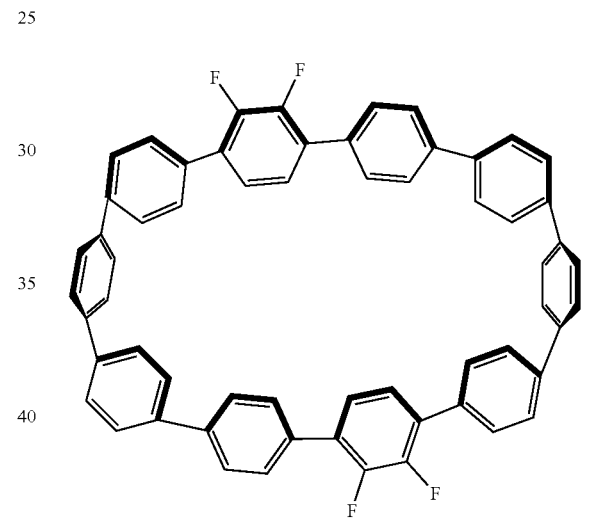
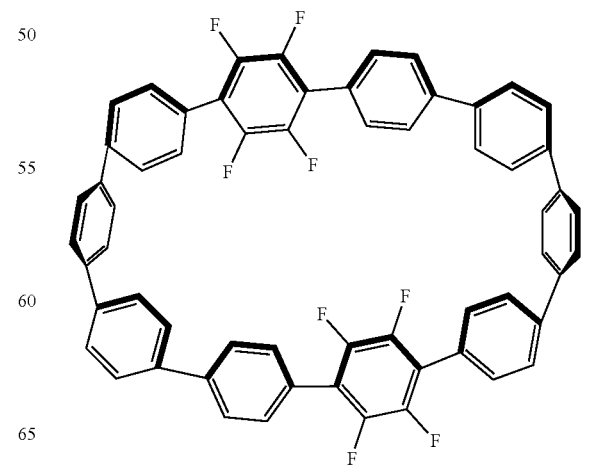

105
-continued
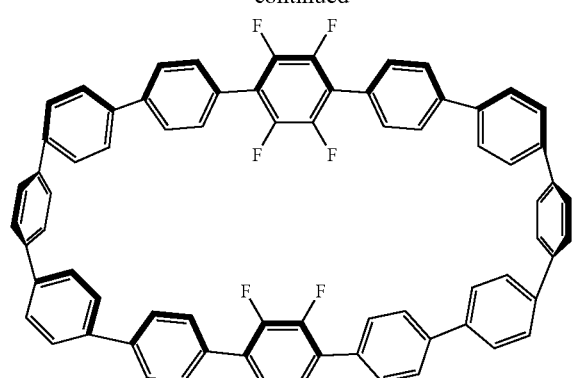
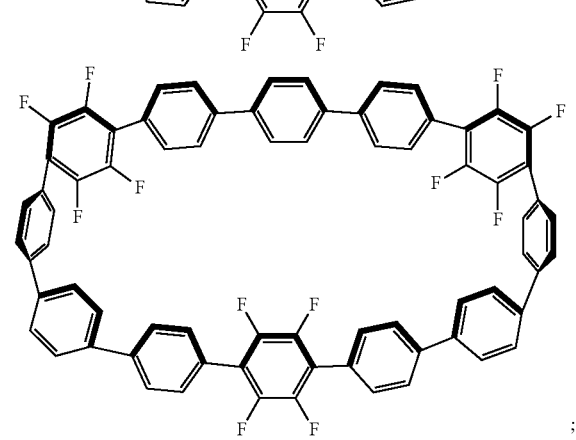
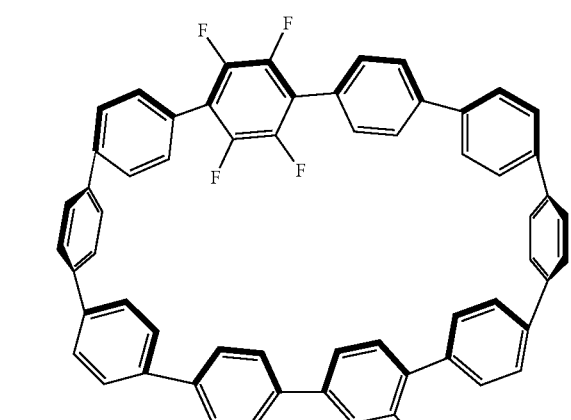
106
-continued
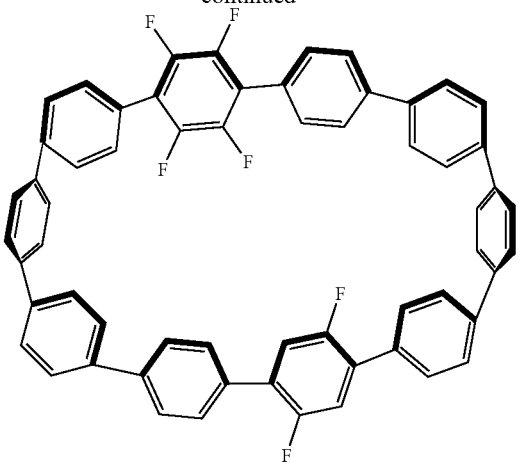
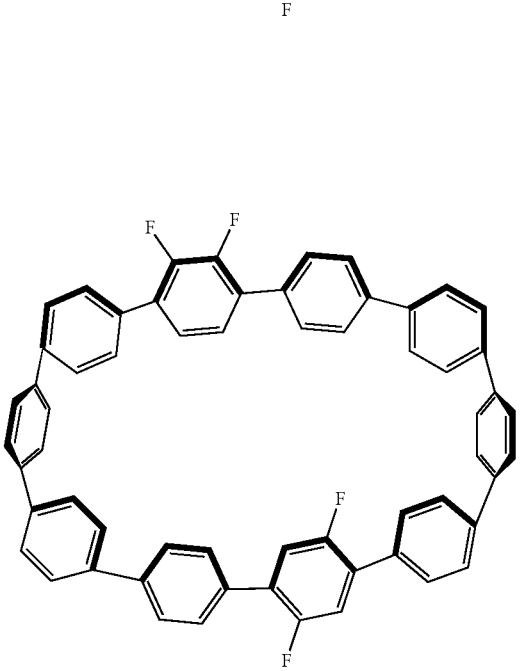
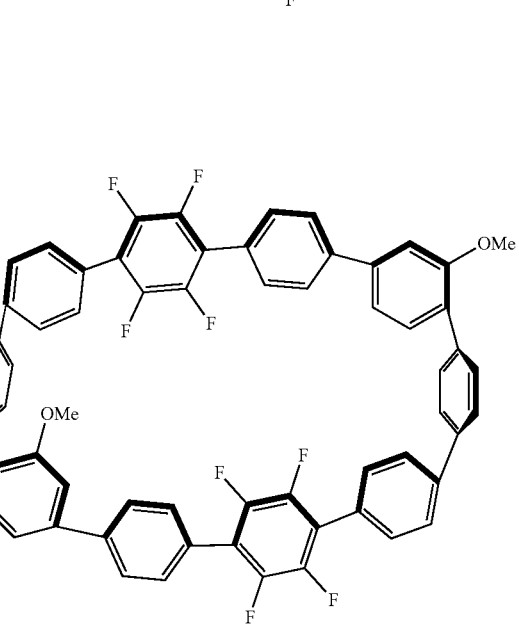

107
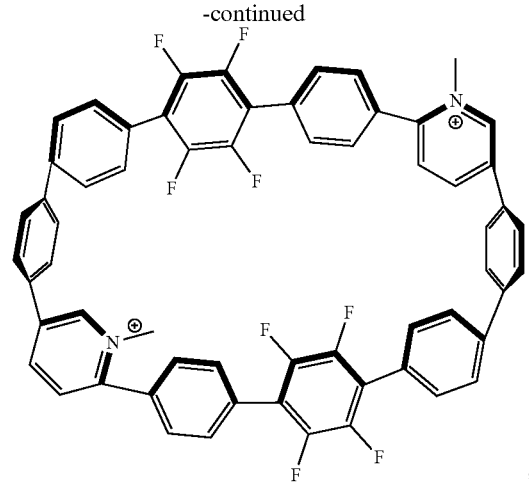
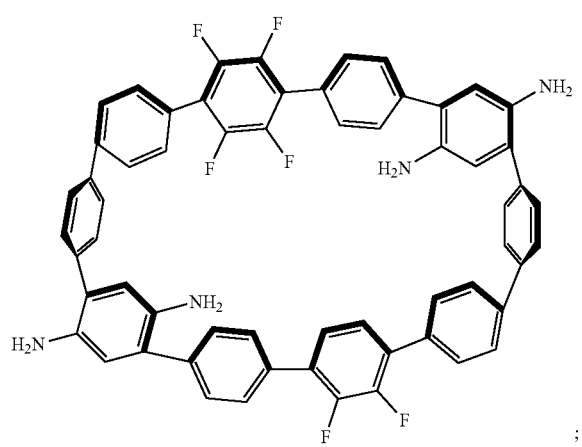
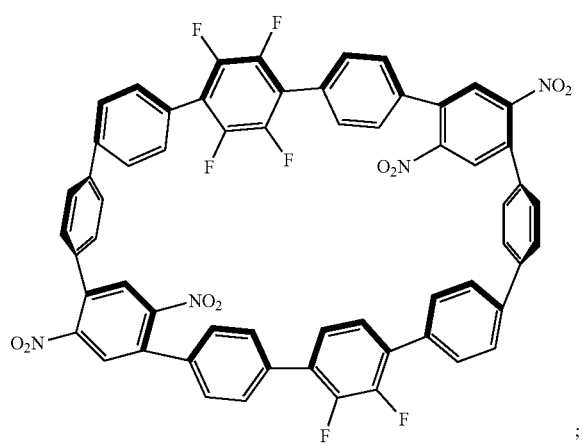
108
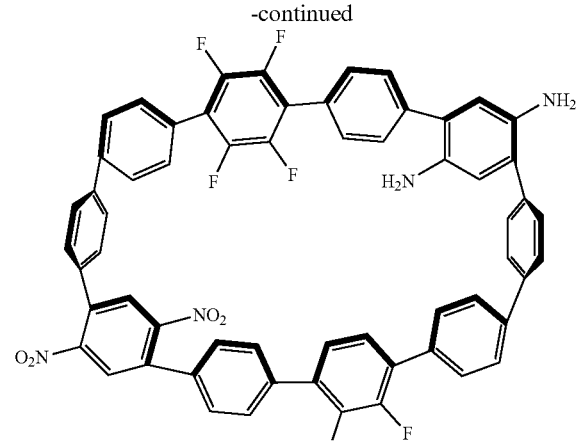
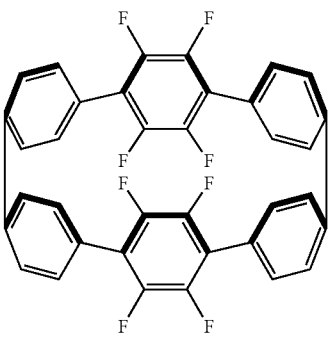
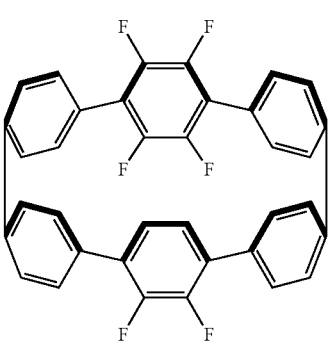
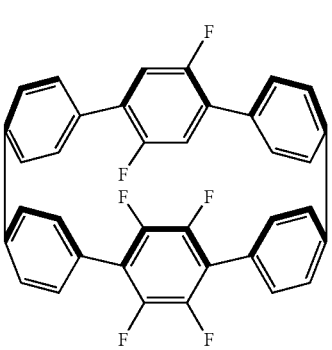

-continued
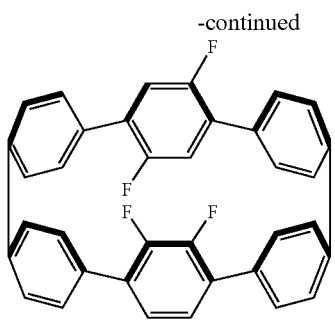
;
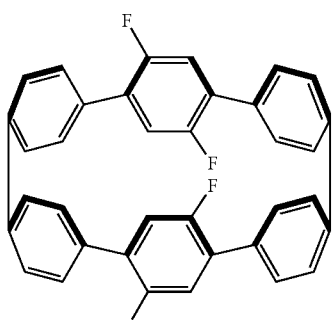
;
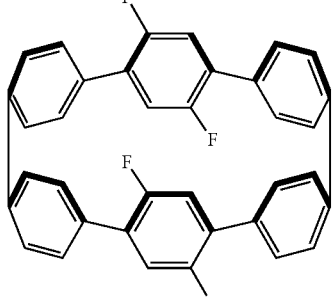
;
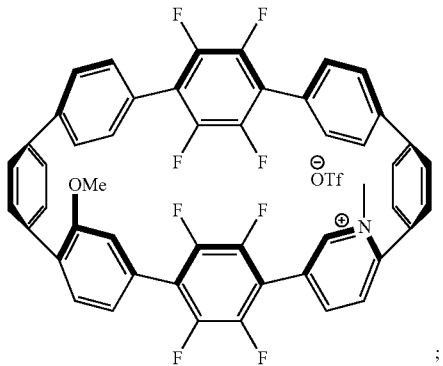
;
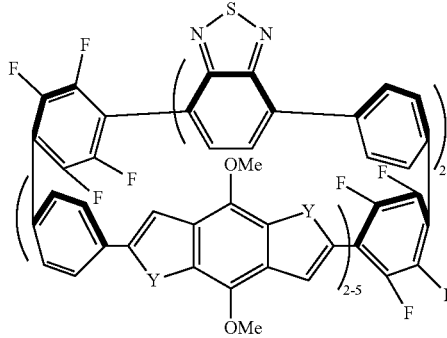
; or
-continued
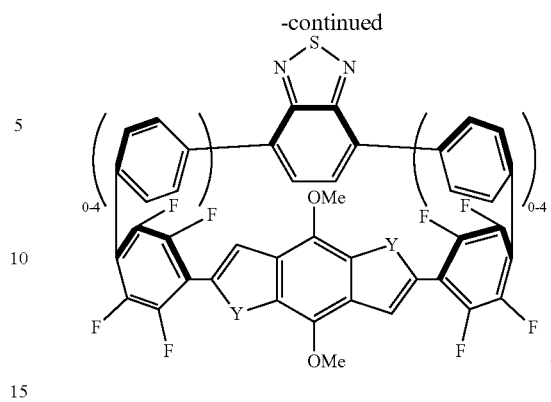
.
3. The compound of claim 1, wherein the compound is
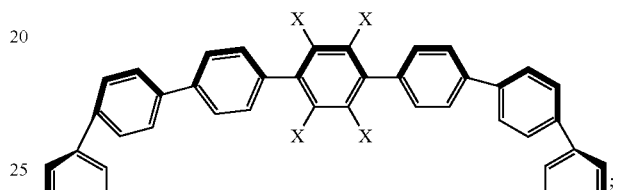
;
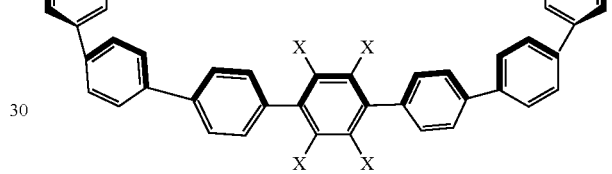
; or
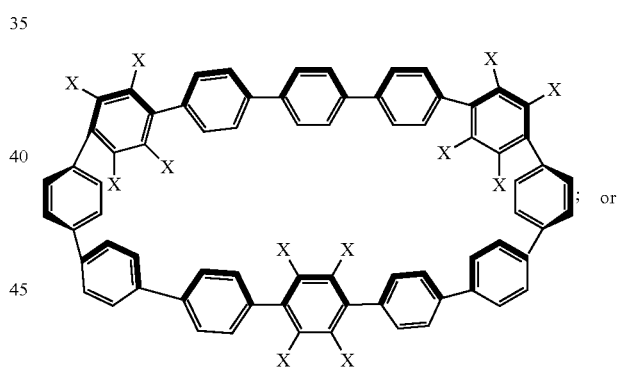
.
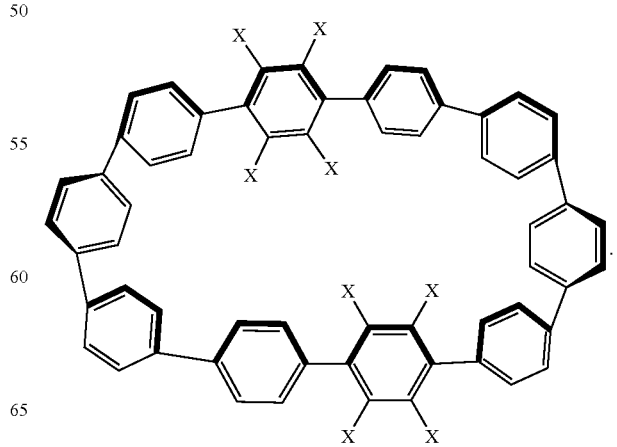

4. The compound of claim 1, wherein the compound is

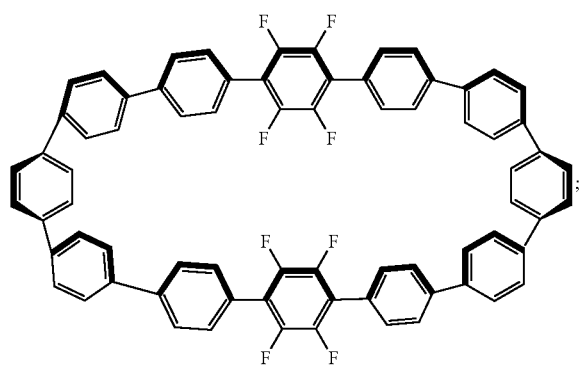

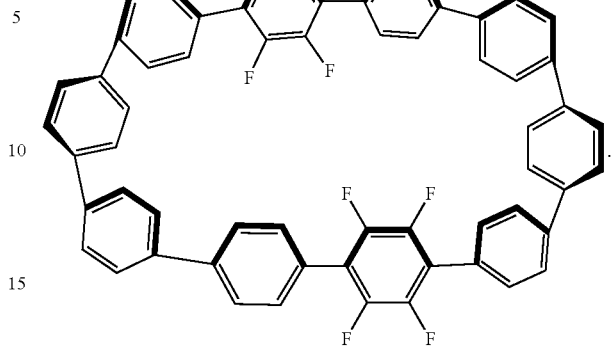

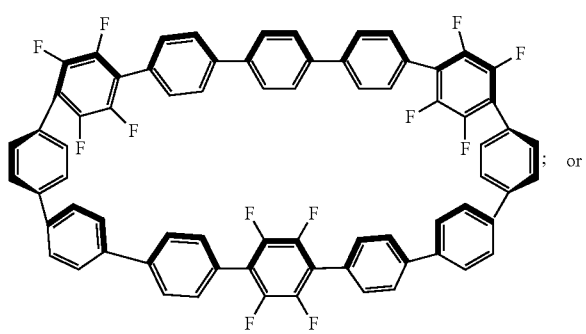

or

5. An assembly, comprising a plurality of nanohoop compounds that are arranged, through one or more C—H/C—X interactions, in a column-like configuration, wherein at least one of the nanohoop compounds is a compound according to claim 1.

6. A device, comprising a halogenated nanohoop compound according to claim 1, wherein the device is an energy storage device, a nanoreactor, an electronic device, a biological transport device, or a chemical device.

7. The device of claim 6, wherein the energy storage device is a capacitor, an electrode, a solar cell, a fuel cell, or a battery.

8. The device of claim 6, wherein the electronic device is a two-contact electronic device.

9. The device of claim 6, wherein the nanoreactor further comprises one or more guest species.

* * * * *